US011306105B2

(12) United States Patent
Bradner et al.

(10) Patent No.: US 11,306,105 B2
(45) Date of Patent: Apr. 19, 2022

(54) CYANO THIENOTRIAZOLODIAZEPINES AND USES THEREOF

(71) Applicant: Dana-Farber Cancer Institute, Inc., Boston, MA (US)

(72) Inventors: James E. Bradner, Weston, MA (US); Jun Qi, Sharon, MA (US); Minoru Tanaka, Boston, MA (US); Dennis Buckley, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 528 days.

(21) Appl. No.: 15/758,822

(22) PCT Filed: Sep. 9, 2016

(86) PCT No.: PCT/US2016/051107
§ 371 (c)(1),
(2) Date: Mar. 9, 2018

(87) PCT Pub. No.: WO2017/044849
PCT Pub. Date: Mar. 16, 2017

(65) Prior Publication Data
US 2020/0199150 A1    Jun. 25, 2020
US 2021/0206779 A9    Jul. 8, 2021

Related U.S. Application Data

(60) Provisional application No. 62/217,521, filed on Sep. 11, 2015.

(51) Int. Cl.
*A61K 31/551*     (2006.01)
*A61P 15/16*      (2006.01)
*C07D 495/14*     (2006.01)

(52) U.S. Cl.
CPC .................. *C07D 495/14* (2013.01)

(58) Field of Classification Search
CPC ...... A61K 31/551; A61P 15/16; C07D 495/14
See application file for complete search history.

(56) References Cited

U.S. PATENT DOCUMENTS

| | | |
|---|---|---|
| 3,681,343 A | 8/1972 | Hester, Jr. |
| 3,709,898 A | 1/1973 | Hester, Jr. |
| 3,812,259 A | 5/1974 | Collins |
| 4,621,083 A | 11/1986 | Casals-Stenzel et al. |
| 4,900,729 A | 2/1990 | Stransky et al. |
| 5,104,543 A | 4/1992 | Brandt et al. |
| 5,593,988 A | 1/1997 | Tahara et al. |
| 5,712,274 A | 1/1998 | Sueoka et al. |
| 5,721,231 A | 2/1998 | Moriwaki et al. |
| 5,753,647 A | 5/1998 | Weber et al. |
| 5,753,649 A | 5/1998 | Tahara et al. |
| 5,760,032 A | 6/1998 | Kitajima et al. |
| 5,846,972 A | 12/1998 | Buckman et al. |
| 5,854,238 A | 12/1998 | Kempen |
| 5,893,397 A | 4/1999 | Peterson et al. |
| 5,993,412 A | 11/1999 | Deily et al. |
| 6,444,664 B1 | 9/2002 | Princen et al. |
| 6,806,272 B2 | 10/2004 | Bauer et al. |
| 6,861,422 B2 | 3/2005 | Hoffmann et al. |
| 7,015,213 B1 | 3/2006 | Bigg et al. |
| 7,371,753 B2 | 5/2008 | Stadtmueller et al. |
| 7,528,143 B2 | 5/2009 | Noronha et al. |
| 7,528,153 B2 | 5/2009 | Noronha et al. |
| 7,589,167 B2 | 9/2009 | Zhou et al. |
| 7,750,152 B2 | 7/2010 | Hoffman et al. |
| 7,786,299 B2 | 8/2010 | Hoffman et al. |
| 7,816,530 B2 | 10/2010 | Grauert |
| 7,825,246 B2 | 11/2010 | Noronha et al. |
| 8,003,786 B2 | 8/2011 | Hoffman et al. |
| 8,044,042 B2 | 10/2011 | Adachi et al. |
| 8,133,900 B2 | 3/2012 | Hood et al. |
| 8,138,199 B2 | 3/2012 | Noronha et al. |
| 8,338,464 B2 | 12/2012 | Melnick et al. |
| 8,476,260 B2 | 7/2013 | Miyoshi et al. |
| 8,604,042 B2 | 12/2013 | Noronha et al. |

(Continued)

FOREIGN PATENT DOCUMENTS

| | | |
|---|---|---|
| CA | 2020806 A1 | 1/1991 |
| CA | 2710740 A1 | 7/2009 |

(Continued)

OTHER PUBLICATIONS

U.S. Appl. No. 14/774,958, filed Sep. 11, 2015, Bradner et al.
U.S. Appl. No. 14/907,339, filed Jan. 25, 2016, Marineau et al.
U.S. Appl. No. 15/114,895, filed Jul. 28, 2016, Bradner et al.
U.S. Appl. No. 15/114,989, filed Jul. 28, 2016, Bradner et al.
U.S. Appl. No. 15/115,038, filed Jul. 28, 2016, Bradner et al.
U.S. Appl. No. 15/115,085, filed Jul. 28, 2016, Bradner et al.
U.S. Appl. No. 15/426,708, filed Feb. 7, 2017, Bradner et al.
U.S. Appl. No. 15/426,660, filed Feb. 7, 2017, Bradner et al.
U.S. Appl. No. 15/758,787, filed Mar. 9, 2018, Bradner et al.
U.S. Appl. No. 13/698,006, filed Apr. 26, 2013, Bradner et al.
U.S. Appl. No. 14/977,343, filed Dec. 21, 2015, Bradner et al.

(Continued)

*Primary Examiner* — Brenda L Coleman
(74) *Attorney, Agent, or Firm* — Wolf, Greenfield & Sacks, P.C.

(57) ABSTRACT

The present invention provides compounds and pharmaceutically compositions thereof. The compounds and compositions are binders of bromodomains and/or bromodomain-containing proteins (e.g., bromo and extra terminal (BET) proteins). Also provided are methods, uses, and kits using the compounds and pharmaceutical compositions for inhibiting the activity (e.g., increased activity) of bromodomains and/or bromodomain-containing proteins and for treating and/or preventing in a subject diseases associated with bromodomains or bromodomain-containing proteins (e.g., proliferative diseases, cardiovascular diseases, viral infections, fibrotic diseases, metabolic diseases, endocrine diseases, and radiation poisoning). The compounds, pharmaceutical compositions, and kits are also useful for male contraception.

28 Claims, 1 Drawing Sheet

(56) References Cited

U.S. PATENT DOCUMENTS

| | | |
|---|---|---|
| 8,981,083 B2 | 3/2015 | Bradner et al. |
| 9,249,161 B2 | 2/2016 | Albrecht et al. |
| 9,301,962 B2 | 4/2016 | Bradner et al. |
| 9,320,741 B2 | 4/2016 | Bradner et al. |
| 9,695,172 B2 | 7/2017 | Bradner et al. |
| 9,714,946 B2 | 7/2017 | Bradner et al. |
| 9,789,120 B2 | 10/2017 | Bradner et al. |
| 9,815,849 B2 | 11/2017 | Bradner et al. |
| 9,938,302 B2 | 4/2018 | Chan et al. |
| 9,951,074 B2 | 4/2018 | Bradner et al. |
| 9,975,896 B2 | 5/2018 | Marineau et al. |
| 10,144,745 B2 | 12/2018 | Chan et al. |
| 10,150,756 B2 | 12/2018 | Bradner et al. |
| 10,308,653 B2 | 6/2019 | Bradner et al. |
| 10,407,441 B2 | 9/2019 | Bradner et al. |
| 10,464,925 B2 | 11/2019 | Bradner et al. |
| 10,793,571 B2 | 10/2020 | Bradner et al. |
| 10,881,668 B2 | 1/2021 | Bradner et al. |
| 2002/0032200 A1 | 3/2002 | Cai et al. |
| 2002/0169158 A1 | 11/2002 | Hunt, III et al. |
| 2003/0130268 A1 | 7/2003 | Sagara et al. |
| 2003/0216758 A1 | 11/2003 | Signore |
| 2004/0176380 A1 | 9/2004 | Hoffmann et al. |
| 2006/0035902 A1 | 2/2006 | Linz et al. |
| 2006/0074088 A1 | 4/2006 | Munzert et al. |
| 2006/0142257 A1 | 6/2006 | Nieschlag et al. |
| 2006/0223055 A1 | 10/2006 | Howley et al. |
| 2007/0105839 A1 | 5/2007 | Imbach et al. |
| 2007/0179178 A1 | 8/2007 | Buettelmann et al. |
| 2007/0218135 A1 | 9/2007 | Mukharya et al. |
| 2008/0004308 A1 | 1/2008 | Dhanak et al. |
| 2008/0081781 A1 | 4/2008 | Lippa et al. |
| 2008/0305113 A1 | 12/2008 | Kwon et al. |
| 2009/0012064 A1 | 1/2009 | Sagara et al. |
| 2009/0238828 A1 | 9/2009 | Munzert et al. |
| 2009/0280115 A1 | 11/2009 | Maier et al. |
| 2009/0281191 A1 | 11/2009 | Rangwala et al. |
| 2009/0312336 A1 | 12/2009 | Simpson et al. |
| 2009/0318408 A1 | 12/2009 | Cai et al. |
| 2010/0041643 A1 | 2/2010 | Adachi et al. |
| 2010/0216802 A1 | 8/2010 | Moffat et al. |
| 2010/0249412 A1 | 9/2010 | Linz et al. |
| 2010/0286127 A1 | 11/2010 | Miyoshi et al. |
| 2011/0028405 A1 | 2/2011 | Harrison et al. |
| 2011/0098288 A1 | 4/2011 | Major et al. |
| 2011/0172231 A1 | 7/2011 | Baenteli et al. |
| 2011/0201606 A1 | 8/2011 | Garcia-Cheverria et al. |
| 2011/0212077 A1 | 9/2011 | Noronha et al. |
| 2011/0230460 A1 | 9/2011 | Kempen et al. |
| 2011/0245245 A1 | 10/2011 | Mortensen et al. |
| 2012/0014979 A1 | 1/2012 | Dent |
| 2012/0040961 A1 | 2/2012 | Gray et al. |
| 2012/0202798 A1 | 8/2012 | Sagara |
| 2012/0329803 A1 | 12/2012 | Guenter et al. |
| 2013/0184264 A1 | 7/2013 | Bradner et al. |
| 2013/0210813 A1 | 8/2013 | Bradner et al. |
| 2013/0245013 A1 | 9/2013 | Gangloff et al. |
| 2013/0252331 A1 | 9/2013 | Bradner et al. |
| 2013/0274239 A1 | 10/2013 | Arnold et al. |
| 2013/0280332 A1 | 10/2013 | Moss et al. |
| 2014/0005169 A1 | 1/2014 | Albrecht et al. |
| 2014/0011862 A1 | 1/2014 | Bradner et al. |
| 2014/0213575 A1 | 7/2014 | Schmees et al. |
| 2014/0243286 A1 | 8/2014 | Arnold et al. |
| 2014/0243322 A1 | 8/2014 | Arnold et al. |
| 2014/0256710 A1 | 9/2014 | Liu et al. |
| 2016/0033519 A1 | 2/2016 | Bradner et al. |
| 2016/0168154 A1 | 6/2016 | Bradner et al. |
| 2016/0176916 A1 | 6/2016 | Bradner et al. |
| 2016/0231314 A1 | 8/2016 | Bradner et al. |
| 2016/0317547 A1 | 11/2016 | Bradner et al. |
| 2016/0332993 A1 | 11/2016 | Bradner et al. |
| 2016/0347749 A1 | 12/2016 | Bradner et al. |
| 2016/0347750 A1 | 12/2016 | Bradner et al. |
| 2017/0008888 A1 | 1/2017 | Hu et al. |
| 2017/0008895 A1 | 1/2017 | Bradner et al. |
| 2017/0065719 A1 | 3/2017 | Qian et al. |
| 2017/0145013 A1 | 5/2017 | Bradner et al. |
| 2017/0145023 A1 | 5/2017 | Bradner et al. |
| 2017/0145026 A1 | 5/2017 | Ernst et al. |
| 2017/0145086 A1 | 5/2017 | Myeette et al. |
| 2017/0209461 A1 | 7/2017 | Landau et al. |
| 2017/0333443 A1 | 11/2017 | Chan et al. |
| 2017/0334932 A1 | 11/2017 | Chan et al. |
| 2017/0360801 A1 | 12/2017 | Sotomayor et al. |
| 2018/0085465 A1 | 3/2018 | Bradner et al. |
| 2018/0134684 A1 | 5/2018 | Bradner et al. |
| 2018/0169109 A1 | 6/2018 | Bradner et al. |
| 2018/0179522 A1 | 6/2018 | Buckley et al. |
| 2018/0228907 A1 | 8/2018 | Crew et al. |
| 2018/0230167 A1 | 8/2018 | Chan et al. |
| 2018/0237453 A1 | 8/2018 | Vadivelu et al. |
| 2018/0327419 A1 | 11/2018 | Bradner et al. |
| 2018/0354973 A1 | 12/2018 | Bradner et al. |
| 2019/0015411 A9 | 1/2019 | Hammerman et al. |
| 2019/0046541 A1 | 2/2019 | Bradner et al. |
| 2019/0076539 A1 | 3/2019 | Phillips et al. |
| 2019/0076542 A1 | 3/2019 | Phillips et al. |
| 2019/0135790 A1 | 5/2019 | Bradner et al. |

FOREIGN PATENT DOCUMENTS

| | | |
|---|---|---|
| CH | 622019 A5 | 3/1981 |
| CN | 1227555 A | 9/1999 |
| CN | 1745081 A | 3/2006 |
| CN | 101022809 A | 8/2007 |
| CN | 101023070 A | 8/2007 |
| CN | 101420955 A | 4/2009 |
| CN | 102341394 A | 2/2012 |
| CN | 103037865 A | 4/2013 |
| DE | 3724164 A1 | 2/1988 |
| EA | 201070395 A1 | 10/2010 |
| EP | 0 087 850 A1 | 9/1983 |
| EP | 0 368 175 A1 | 5/1990 |
| EP | 0 387 613 A1 | 9/1990 |
| EP | 407955 A1 | 1/1991 |
| EP | 0 934 940 A1 | 8/1999 |
| EP | 0 989 131 B1 | 11/2002 |
| EP | 1 297 836 A1 | 4/2003 |
| EP | 1887008 A1 | 2/2008 |
| EP | 2 112 152 A1 | 10/2009 |
| EP | 2 239 264 A1 | 10/2010 |
| EP | 2 481 739 A1 | 8/2012 |
| ES | 2 351 367 T3 | 2/2011 |
| FR | 2329668 A1 | 5/1977 |
| JP | 61-87684 A | 5/1986 |
| JP | 1-299231 | 12/1989 |
| JP | 6-157316 A | 6/1994 |
| JP | H10500998 A | 1/1998 |
| JP | 11-228576 | 8/1999 |
| JP | 11-512107 A | 10/1999 |
| JP | 3001979 | 11/1999 |
| JP | 3096299 | 8/2000 |
| JP | 2005-527529 | 9/2005 |
| JP | 2006-520354 | 9/2006 |
| JP | 2008-509948 A | 4/2008 |
| JP | 2008-509953 A | 4/2008 |
| JP | 2008-510763 | 4/2008 |
| JP | 2008-510771 A | 4/2008 |
| JP | 2008-156311 A | 7/2008 |
| JP | 2008-543778 | 12/2008 |
| JP | 2009-526849 A | 7/2009 |
| JP | 2011-513457 A | 4/2011 |
| JP | 2011-515383 A | 5/2011 |
| JP | 2012-514601 A | 6/2012 |
| JP | 2013-543879 A | 12/2013 |
| JP | 2016-504990 A | 2/2016 |
| JP | 5913292 B2 | 4/2016 |
| MX | 2017011919 A1 | 5/2018 |
| PT | 2 139 892 E | 11/2011 |
| RU | 2229299 C2 | 5/2004 |
| RU | 2475488 C2 | 3/2010 |
| RU | 2514429 C2 | 4/2014 |
| WO | WO 1994/006802 A1 | 3/1994 |

(56) References Cited

FOREIGN PATENT DOCUMENTS

| | | |
|---|---|---|
| WO | WO 97/47622 A1 | 12/1997 |
| WO | WO 98/11111 A1 | 3/1998 |
| WO | WO 01/95912 A1 | 12/2001 |
| WO | WO 2003/020722 A1 | 3/2003 |
| WO | WO 2006/018185 A2 | 2/2006 |
| WO | WO 2006/133426 A2 | 12/2006 |
| WO | WO 2007/053452 | 5/2007 |
| WO | WO 2007/095188 A2 | 8/2007 |
| WO | WO 2008/009909 A1 | 1/2008 |
| WO | WO 2008/079907 A1 | 7/2008 |
| WO | WO 2008/083056 A2 | 7/2008 |
| WO | WO 2008/113711 A1 | 9/2008 |
| WO | WO 2008/137081 A1 | 11/2008 |
| WO | WO 2009/023269 A3 | 2/2009 |
| WO | WO 2009/040556 A1 | 4/2009 |
| WO | WO 2009/067547 A1 | 5/2009 |
| WO | WO 2009/084693 A1 | 7/2009 |
| WO | WO 2009/153197 A1 | 12/2009 |
| WO | WO 2010/015387 A1 | 2/2010 |
| WO | WO 2010/032195 A1 | 3/2010 |
| WO | WO 2010/049466 A1 | 5/2010 |
| WO | WO 2010/080712 A1 | 7/2010 |
| WO | WO 2011/036566 A1 | 3/2011 |
| WO | WO 2011/054553 A1 | 5/2011 |
| WO | WO 2011/054841 A1 | 5/2011 |
| WO | WO 2011/054843 A1 | 5/2011 |
| WO | WO 2011/054844 A1 | 5/2011 |
| WO | WO 2011/054845 A1 | 5/2011 |
| WO | WO 2011/054846 A1 | 5/2011 |
| WO | WO 2011/054848 A1 | 5/2011 |
| WO | WO 2011/101369 A1 | 8/2011 |
| WO | WO 2011/143651 A1 | 11/2011 |
| WO | WO 2011/143657 A1 | 11/2011 |
| WO | WO 2011/143660 A2 | 11/2011 |
| WO | WO 2011/143669 A2 | 11/2011 |
| WO | WO 2011/161031 A1 | 12/2011 |
| WO | WO 2012/072505 A1 | 6/2012 |
| WO | WO 2012/075383 A2 | 6/2012 |
| WO | WO 2012/075456 A1 | 6/2012 |
| WO | WO 2012/116170 A1 | 8/2012 |
| WO | WO 2012/118812 A2 | 9/2012 |
| WO | WO 2012/120048 A1 | 9/2012 |
| WO | WO 2012/143416 A2 | 10/2012 |
| WO | WO 2013/033268 A2 | 3/2013 |
| WO | WO 2013/033269 A1 | 3/2013 |
| WO | WO 2013/033270 A2 | 3/2013 |
| WO | WO 2013/097601 A1 | 7/2013 |
| WO | WO 2013/148197 A1 | 10/2013 |
| WO | WO 2014/023696 A1 | 2/2014 |
| WO | WO 2014/068402 A2 | 5/2014 |
| WO | WO 2014/071247 A1 | 5/2014 |
| WO | WO 2014/095774 A1 | 6/2014 |
| WO | WO 2014/139324 A1 | 9/2014 |
| WO | WO 2014/139394 A1 | 9/2014 |
| WO | WO 2014/159392 A1 | 10/2014 |
| WO | WO 2015/013635 A2 | 1/2015 |
| WO | WO 2015/081280 A1 | 6/2015 |
| WO | WO 2015/081284 A1 | 6/2015 |
| WO | WO 2015/085925 A1 | 6/2015 |
| WO | WO 2015/117053 A1 | 8/2015 |
| WO | WO 2015/117055 A1 | 8/2015 |
| WO | WO 2015/117083 A1 | 8/2015 |
| WO | WO 2015/117087 A1 | 8/2015 |
| WO | WO 2016/022902 A1 | 2/2016 |
| WO | WO 2016/105518 A1 | 6/2016 |
| WO | WO 2016/149668 A1 | 9/2016 |
| WO | WO 2017/030814 | 2/2017 |
| WO | WO 2017/037146 A1 | 3/2017 |
| WO | WO 2017/042100 A1 | 3/2017 |
| WO | WO 2017/044792 A1 | 3/2017 |
| WO | WO 2017/044849 A1 | 3/2017 |
| WO | WO 2017/091585 A1 | 6/2017 |
| WO | WO 2017/091600 A1 | 6/2017 |
| WO | WO 2017/091602 A1 | 6/2017 |
| WO | WO 2017/091617 A1 | 6/2017 |
| WO | WO 2017/091627 A1 | 6/2017 |
| WO | WO 2017/091673 A2 | 6/2017 |
| WO | WO 2017/091683 A1 | 6/2017 |
| WO | WO 2017/094750 A1 | 6/2017 |
| WO | WO 2017/198590 A1 | 11/2017 |

OTHER PUBLICATIONS

U.S. Appl. No. 13/697,963, filed Jun. 3, 2013, Bradner et al.
International Search Report and Written Opinion for PCT/US2014/023386, dated Jul. 9, 2014.
International Preliminary Report on Patentability for PCT/US2014/023386, dated Sep. 24, 2015.
Extended European Search Report for EP 14828728, dated Jan. 31, 2017.
Invitation to Pay Additional Fees for PCT/US2014/48230, dated Nov. 17, 2014.
International Search Report and Written Opinion for PCT/US2014/48230, dated Jan. 30, 2015.
International Preliminary Report on Patentability for PCT/US2014/48230, dated Feb. 4, 2016.
Extended European Search Report for EP 15744026.4, dated Jun. 7, 2017.
Invitation to Pay Additional Fees for PCT/US2015/14109, dated Apr. 20, 2015.
International Search Report and Written Opinion for PCT/US2015/14109, dated Jul. 6, 2015.
International Preliminary Report on Patentability for PCT/US2015/14109, dated Aug. 11, 2016.
Extended European Search Report for EP 15743171.9, dated Jul. 10, 2017.
International Search Report and Written Opinion for PCT/US2015/14044, dated Apr. 23, 2015.
International Preliminary Report on Patentability for PCT/US2015/14044, dated Aug. 11, 2016.
Extended European Search Report for EP 15742537, dated Jun. 22, 2017.
International Search Report and Written Opinion for PCT/US2015/14039, dated Apr. 23, 2015.
International Preliminary Report on Patentability for PCT/US2015/14039, dated Aug. 11, 2016.
Extended European Search Report for EP 15743564.5, dated Jul. 13, 2017.
International Search Report and Written Opinion for PCT/US2015/14120, dated Apr. 23, 2015.
International Preliminary Report on Patentability for PCT/US2015/14120, dated Aug. 11, 2016.
Extended European Search Report for EP 15830298.4, dated Nov. 24, 2017.
International Search Report and Written Opinion for PCT/US2015/044180, dated Nov. 5, 2015.
International Preliminary Report on Patentability for PCT/US2015/044180, dated Feb. 23, 2017.
Extended European Search Report for EP 15829064.3, dated Dec. 21, 2017.
Invitation to Pay Additional Fees for PCT/US2015/044303, dated Oct. 21, 2015.
International Search Report and Written Opinion for PCT/US2015/044303, dated Dec. 31, 2015.
International Preliminary Report on Patentability for PCT/US2015/044303, dated Feb. 23, 2017.
Invitation to Pay Additional Fees for PCT/US2016/051017, dated Oct. 31, 2016.
International Search Report and Written Opinion for PCT/US2016/051017, dated Jan. 10, 2017.
International Preliminary Report on Patentability for PCT/US2016/051017, dated Mar. 22, 2018.
International Search Report and Written Opinion for PCT/US2016051107, dated Nov. 22, 2016.
International Preliminary Report on Patentability for PCT/US2016051107, dated Mar. 22, 2018.
Invitation to Pay Additional Fees for PCT/US2016/63502, dated Feb. 9, 2017.

(56) References Cited

OTHER PUBLICATIONS

International Search Report and Written Opinion for PCT/US2016/63502, dated May 10, 2017.
International Search Report and Written Opinion for PCT/US2011/036667, dated Aug. 15, 2011.
International Preliminary Report on Patentability for PCT/US2011/036667, dated Nov. 29, 2012.
International Search Report and Written Opinion for PCT/US2011/036647, dated Aug. 17, 2011.
International Preliminary Report on Patentability for PCT/US2011/036647, dated Nov. 29, 2012.
International Search Report and Written Opinion for PCT/US2011/036672, dated Jan. 27, 2012.
International Preliminary Report on Patentability for PCT/US2011/036672, dated Nov. 29, 2012.
International Search Report and Written Opinion for PCT/US2011/036701, dated Feb. 1, 2012.
International Preliminary Report on Patentability for PCT/US2011/036701, dated Nov. 29, 2012.
CAPLUS Database Result for Hoffman et al., WO 2003/020722 A1 (Mar. 13, 2003). Caplus Accession No. 2003:202640.
CAPLUS Database Result for Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67. doi: 10.1016/j.ejmech.2013.10.052. Epub Oct. 29, 2013. Accession No. 2013:1979798. Abstract Only.
GENBANK Submission; NH/NCBI, Accession No. H86170. Hillier et al., Nov. 21, 1995. 2 pages.
GENBANK Submission; NH/NCBI, Accession No. NP_001003694. Lubula et al., Oct. 6, 2016. 4 pages.
GENBANK Submission; NH/NCBI, Accession No. NP_001420. Ledsaak et al., Sep. 15, 2016. 8 pages.
GENBANK Submission; NH/NCBI, Accession No. NP_001717. Barda et al., Feb. 2, 2014. 2 pages.
GENBANK Submission; NH/NCBI, Accession No. NP_003061. Agaimy et al., Dec. 10, 2016. 5 pages.
GENBANK Submission; NH/NCBI, Accession No. NP_003063. Liao et al., May 2, 2016. 5 pages.
GENBANK Submission; NH/NCBI, Accession No. NP_003875. Li et al., Oct. 7, 2016. 3 pages.
GENBANK Submission; NH/NCBI, Accession No. NP_004371. Liu et al., Dec. 10, 2006. 3 pages.
GENBANK Submission; NH/NCBI, Accession No. NP_004597. Herzfeld et al., Aug. 26, 2016. 5 pages.
GENBANK Submission; NH/NCBI, Accession No. NP_005095. Xiao et al., Oct. 6, 2016. 4 pages.
GENBANK Submission; NH/NCBI, Accession No. NP_005753. Dalgaard et al., Oct. 6, 2016. 6 pages.
GENBANK Submission; NH/NCBI, Accession No. NP_009168. DiBernardo et al., Sep. 28, 2008. 2 pages.
GENBANK Submission; NH/NCBI, Accession No. NP_031397. Shao et al., Jan. 4, 2017. 4 pages.
GENBANK Submission; NH/NCBI, Accession No. NP_038478. Jones et al., Sep. 23, 2005. 2 pages.
GENBANK Submission; NH/NCBI, Accession No. NP_054828. Hou et al., Sep. 15, 2016. 5 pages.
GENBANK Submission; NH/NCBI, Accession No. NP_055392. Aberg et al., Mar. 22, 2014. 3 pages.
GENBANK Submission; NH/NCBI, Accession No. NP_060404. Bezrookove et al., Oct. 7, 2016. 5 pages.
GENBANK Submission; NH/NCBI, Accession No. NP_060635. Varela et al., Dec. 18, 2011. 3 pages.
GENBANK Submission; NH/NCBI, Accession No. NP_060959. Kuryshev et al., Mar. 26, 2006. 2 pages.
GENBANK Submission; NH/NCBI, Accession No. NP_061836. Perry et al., Feb. 21, 2016. 7 pages.
GENBANK Submission; NH/NCBI, Accession No. NP_066564. Wiper-Bergeron et al., Jun. 3, 2007. 3 pages.
GENBANK Submission; NH/NCBI, Accession No. NP_076413. Clark et al., Jun. 27, 2007. 2 pages.
GENBANK Submission; NH/NCBI, Accession No. NP_113601. Knijnenburg et al., Jan. 17, 2014. 3 pages.
GENBANK Submission; NH/NCBI, Accession No. NP_490597. Duan et al., Oct. 6, 2016. 5 pages.
GENBANK Submission; NH/NCBI, Accession No. NP_612411. Saare et al., Aug. 25, 2016. 2 pages.
GENBANK Submission; NH/NCBI, Accession No. NP_722516. Xia et al., Nov. 22, 2015. 3 pages.
GENBANK Submission; NH/NCBI, Accession No. NP_872579. Lee et al., Oct. 6, 2016. 4 pages.
GENBANK Submission; NH/NCBI, Accession No. XP_039676. [No Author Listed], Aug. 19, 2004. 3 pages.
[No Author Listed], Methanesulfonyl chloride: Difference between revisions. Wikipedia entry. http://en.wikipedia.org/w/index.phptitle=Methanesulfonyl_chloride&diff=602110747&oldid=601684911. Last accessed Feb. 23, 2016. 2 pages.
[No Author Listed], PubChem CID 5325760. Published Jan. 25, 2006. pubchem.ncbi.nlm.nih/gov//compound/5325760?from=summary#section=Top. Last accessed Oct. 20, 2014.
[No Author Listed], PubChem CID-55504609. Create date Jan. 25, 2012. https://pubchem.ncbi.nlm.nih.gov/compound/55504609. Last accessed Feb. 23, 2016.
[No Author Listed], PubChem CID-56267130. Create date Jan. 25, 2012. https://pubchem.ncbi.nlm.nih.gov/compound/56267130. Last accessed Feb. 23, 2016.
[No Author Listed], PubChem SID 225027960. Available date/deposit date: Feb. 2, 2015. pubchem.ncbi.nlm.nih.gov/substance/225027960. Last accessed Nov. 28, 2016.
[No Author Listed], PubChem SID 235048169. Feb. 13, 2015. Retrieved on Oct. 24, 2016. Available at https://pubchem.ncbi.nlm.nih.gov/substance/235048169.
[No Author Listed], PubChem SID 235671906. Feb. 13, 2015. Retrieved on Oct. 24, 2016. Available at https://pubchem.ncbi.nlm.nih.gov/substance/235671906#section=Top>.
Abbate et al., Structure of the papillomavirus DNA-tethering complex E2:Brd4 and a peptide that ablates HPV chromosomal association. Mol Cell. Dec. 28, 2006;24(6):877-89.
Anders et al., Genome-wide localization of small molecules. Nat Biotechnol. Jan. 2014;32(1):92-6. doi: 10.1038/nbt.2776. Epub Dec. 15, 2013.
Arango et al., Reversible azoospermia in a patient treated with triazolam. Eur J Contracept Reprod Health Care. Sep. 1996;1(3):293-4.
Bartholomeeusen et al., Bromodomain and extra-terminal (BET) bromodomain inhibition activate transcription via transient release of positive transcription elongation factor b (P-TEFb) from 7SK small nuclear ribonucleoprotein. J Biol Chem. Oct. 19, 2012;287(43):36609-16. doi: 10.1074/jbc.M112.410746. Epub Sep. 5, 2012.
Baud et al., Chemical biology. A bump-and-hole approach to engineer controlled selectivity of BET bromodomain chemical probes. Science. Oct. 31, 2014;346(6209):638-41. doi: 10.1126/science.1249830. Epub Oct. 16, 2014.
Berge et al., Pharmaceutical salts. J Pharm Sci. Jan. 1977;66(1):1-19.
Berkovits et al., "The Role of the Double Bromodomain-Containing BET Genes During Mammalian Spermatogenesis," Current Topics in Developmental Biology, 102: 293-326 (2013).
Berkovits et al., The first bromodomain of the testis-specific double bromodomain protein Brdt is required for chromocenter organization that is modulated by genetic background. Dev Biol. Dec. 15, 2011;360(2):358-68. doi: 10.1016/j.ydbio.2011.10.005. Epub Oct. 12, 2011.
Buchdunger et al., Selective inhibition of the platelet-derived growth factor signal transduction pathway by a protein-tyrosine kinase inhibitor of the 2-phenylaminopyrimidine class. Proc Natl Acad Sci U S A. Mar. 28, 1995;92(7):2558-62.
Buchdunger et al.,"Inhibition of the Abl Protein-Tyrosine Kinase In Vitro And In Vivo By A 2-Phenylaminopyrimidine Derivative," Cancer Res, 56:100-104 (1996).
Bullock et al., Structural basis of inhibitor specificity of the human protooncogene proviral insertion site in moloney murine leukemia virus (PIM-1) kinase. J Med Chem. Dec. 1, 2005;48(24):7604-14.

(56) References Cited

OTHER PUBLICATIONS

Cellai et al., Mechanistic Insight Into WEB-2170-induced Apoptosis in Human Acute Myelogenous Leukemia Cells: the Crucial Role of PTEN, Exp Hematol, 37(10):1176-1185 (2009).
Cellai et al., Specific PAF Antagonist WEB-2086 Induces Terminal Differentiation Of Murine and Human Leukemia Cells. FASEB, 16:733-735 (2002).
Chaidos et al., Potent antimyeloma activity of the novel bromodomain inhibitors I-BET151 and I-BET762. Blood. Jan. 30, 2014;123(5):697-705. doi: 10.1182/blood-2013-01-478420. Epub Dec. 13, 2013.
Cheng et al., Adjudin disrupts spermatogenesis via the action of some unlikely partners: Eps8, Arp2/3 complex, drebrin E, PAR6 and 14-3-3. Spermatogenesis. Oct. 2011;1(4):291-297. Epub Oct. 1, 2011.
Cho et al., An unnatural biopolymer. Science. Sep. 3, 1993;261(5126):1303-5.
Choi et al., Brain Penetrant LRRK2 Inhibitor. ACS Med Chem Lett. Aug. 9, 2012;3(8):658-662.
Cole, "Chemical probes for histone-modifying enzymes," Nat Chem Biol 4, 590-597 (2008).
Congiu et al., Synthesis and biological evaluation of novel acylhydrazone derivatives as potential antitumor agents. Bioorganic & Medicinal Chemistry Aug. 22, 2013;21(21):6592-9. DOI: 10.1016/j.bmc.2013.08.026.
Crawford et al., "Bromodomain 4 activation predicts breast cancer survival," Proc Natl Acad Sci, 105, 6380-6385, (2008).
Dawson et al., Inhibition of BET recruitment to chromatin as an effective treatment for MLL-fusion leukaemia. Nature. Oct. 2, 2011;478(7370):529-33. doi: 10.1038/nature10509.
Delbroek et al., Development of an enzyme-linked immunosorbent assay for detection of cellular and in vivo LRRK2 S935 phosphorylation. J Pharm Biomed Anal. Mar. 25, 2013;76:49-58.
Delmore et al., BET bromodomain inhibition as a therapeutic strategy to target c-Myc. Cell. Sep. 16, 2011;146(6):904-17. doi: 10.1016/j.cell.2011.08.017. Epub Sep. 1, 2011.
Deng et al., Characterization of a selective inhibitor of the Parkinson's disease kinase LRRK2. Nat Chem Biol. Apr. 2011;7(4):203-5.
Deng et al., Discovery of a benzo[e]pyrimido-[5,4-b][1,4]diazepin-6(11H)-one as a Potent and Selective Inhibitor of Big MAP Kinase 1. ACS Med Chem Lett. Mar. 10, 2011;2(3):195-200.
Deng et al., Structural determinants for ERK5 (MAPK7) and leucine rich repeat kinase 2 activities of benzo[e]pyrimido-[5,4-b]diazepine-6(11H)-ones. Eur J Med Chem. 2013;70:758-67.
Denis et al., "An Emerging Role for Bromodomain-Containing Proteins in Chromatin Regulation and Transcriptional Control of Adipogenesis," FEBS Lett., 584(15):3260-3268 (2010).
Dey et al., "Brd4 Marks Select Genes of Mitotic Chromatin and Directs Postmitotic Transcription," Molecular Biology of the Cell, 20:4899-4909 (2009).
Druker et al., "Effects of a selective inhibitor of the Abl Tyrosine kinase on the Growth of Bcr-Abl positive cells," Nat Med, 2:561-566 (1996).
Druker et al., "Efficacy and safety of a specific inhibitor of the BCR-ABL tyrosine kinase in chronic myeloid leukemia," N Engl J Med 344, 1031-1037 (2001).
Elkins et al., X-ray crystal structure of ERK5 (MAPK7) in complex with a specific inhibitor. J Med Chem. Jun. 13, 2013;56(11):4413-21.
Ember et al., Acetyl-lysine binding site of bromodomain-containing protein 4 (BRD4) interacts with diverse kinase inhibitors. ACS Chem Biol. May 16, 2014;9(5):1160-71. doi: 10.1021/cb500072z. Epub Mar. 13, 2014.
Fedorov et al., "A Systematic Interaction Map of Validated Kinase Inhibitors with Ser/Thr kinases," Proc Natl Acad Sci., 104(51):20523-20528 (2007).
Filippakopoulos et al., Targeting bromodomains: epigenetic readers of lysine acetylation. Nat Rev Drug Discov. May 2014;13(5):337-56. doi: 10.1038/nrd4286. Epub Apr. 22, 2014.

French et al., "BRD4 Bromodomain Gene Reanangement in Aggressive Carcinoma with Translocation t(15;19)," Aτ J Pathol, 159(6):1987-1992 (2001).
French et al., BRD4-NUT fusion oncogene: a novel mechanism in aggressive carcinoma. Cancer Res. Jan. 15, 2003;63(2):304-7.
French et al., BRD-NUT oncoproteins: a family of closely related nuclear proteins that block epithelial differentiation and maintain the growth of carcinoma cells. Oncogene. Apr. 3, 2008;27(15):2237-42. Epub Oct. 15, 2007.
French, "Demystified Molecular pathology of NUT Midline Carcinomas," J Clin Pathol, 63:492-496 (2010).
Gallenkamp et al., Bromodomains and their pharmacological inhibitors. ChemMedChem. Mar. 2014;9(3):438-64. doi: 10.1002/cmdc.201300434. Epub Feb. 4, 2014.
Greenwald et al., "E.u-BRD2 Transgenic Mice Develop B-Cell Lymphoma and Leukemia," Blood, 103(4):1475-1484 (2004).
Haack et al., "Diagnosis of NUT Midline Carcinoma Using a NUT-specific Monoclonal Antibody," Aτ J Surg Pathol, 33:984-991 (2009).
He et al., The histone methyltransferase Ezh2 is a crucial epigenetic regulator of allogeneic T-cell responses mediating graft-versus-host disease. Blood. Dec. 12, 2013;122(25):4119-28. Doi: 10.1182/blood-2013-05-505180. Epub Oct. 18, 2013.
Houzelstein et al., Growth and early postimplantation defects in mice deficient for the bromodomain-containing protein Brd4. Mol Cell Biol. Jun. 2002;22(11):3794-802.
Hu et al., Adjudin targeting rabbit germ cell adhesion as a male contraceptive: a pharmacokinetics study. J Androl. Jan.-Feb. 2009;30(1):87-93. doi: 10.2164/jandrol.108.004994. Epub Sep. 18, 2008.
Huang et al., "Brd4 Coactivates Transcriptional Activation of NF-kB via Specific Binding to Acetylated RelA," Mol Cell Biol, 29(5):1375-1387 (2009).
Kadota et al., "Identification Of Novel Gene Amplifications In Breast Cancer And Coexistence Of Gene Amplification With An Activating Mutation Of PIK3CA," Cancer Res, 69: 7357-7365 (2009).
Kavanagh et al., The development of CNS-active LRRK2 inhibitors using property-directed optimisation.Bioorg Med Chem Lett. Jul. 1, 2013;23(13):3690-6.
Kim et al., "Berberine Improves Lipid Dysregulation in Obesity by Controlling Central and Peripheral AMPK Activity," Aτ. J. Physiol. Endocrinol. Metab., 296: E812-E819 (2009).
Knapp et al., Selective Targeting of Protein Interactions. Mediated by Epigenetic Effector Domains. SGC Sep. 5, 2013;1-35.
Konze et al., An orally bioavailable chemical probe of the Lysine Methyltransferases EZH2 and EZH1. ACS Chem Biol. 2013;8(6):1324-34. Doi: 10.1021/cb400133j. Epub Apr. 24, 2013.
Krueger et al., The mechanism of release of P-TEFb and HEXIM1 from the 7SK snRNP by viral and cellular activators includes a conformational change in 7SK. PLoS One. Aug. 23, 2010;5(8):e12335. doi: 10.1371/journal.pone.0012335.
Lawless et al., Histone Deacetylase Inhibitors Target Diabetes Via Chromatin Remodeling or as Chemical Chaperones? Curr Diabetes Rev, 5(3):201-209 (2009).
Le Coutre et al., In vivo eradication of human BCR/ABL-positive leukemia cells with an ABL kinase inhibitor. J Natl Cancer Inst, 91:163-168 (1999).
Lee et al., "Berberine, a Natural Plant Product, Activates AMP-Activated Protein Kinase with Beneficial Metabolic Effects in Diabetic and Insulin-Resistant States," Diabetes, 55: 2256-2264 (2006).
Lotti et al., Ultrasound of the male genital tract in relation to male reproductive health. Hum Reprod Update. Jan.-Feb. 2015;21(1):56-83. doi: 10.1093/humupd/dmu042. Epub Jul. 19, 2014.
Marushige, Activation of Chromatin by Acetylation of Histone Side Chains, Proc. Nat'l. Acad. Sci., 73(11): 3937-3941 (1976).
Matzuk, "Small-Molecule Inhibition of BRDT for Male Contraception," Cell: 150:673-684 (2012).
McKeown et al., Biased multicomponent reactions to develop novel bromodomain inhibitors. J Med Chem. Nov. 13, 2014;57(21):9019-27. doi: 10.1021/jm501120z. Epub Oct. 31, 2014.

(56) References Cited

OTHER PUBLICATIONS

Meguro et al., "Heterocycles. VI. Synthesis of 4H-s-Triazolo[4,3-a][1,4]benzodiazepines, Novel Tricyclic Psychosedatives," Chem. Pharm. Bull.,21(11):2382-2390 (1973).

Meng-Er et al., "Use of All-Trans Retinoic Acid in the Treatment of Acute Promyelocytic Leukemia," Blood, 72(2): 567-572 (1988).

Mochizuki et al., "The Bromodomain Protein Brd4 Stimulates G1 Gene Transcription And Promotes Progression To S Phase," J Biol Chem, 283(14):9040-9048 (2008).

Niesen et al., "The use of Differential Scanning Fluorimetry to Detect Ligand Interactions that Promote Protein Stability," Nat Protoc, 2(9):2212-2221 (2007).

Nishimura et al., Fertility and Reproduction Studies of Apafant (WEB 2086 BS) in Rats Dosed Orally. Oyo Yakuri/Pharmacometrics. Oct. 1, 1996. 52(3/4):185-200.

Owen et al., "The Structural Basis for the Recognition of Acetylated Histone R4 by the Bromodomain of Histone Acetyltransferase Gcn5p," The EMBO Journal, 19(22):6141-6149 (2000).

Patani et al., "Bioisosterism: A Rational Approach in Drug Design," Chem. Rev., 96:3147-3176 (1996).

Phelps et al., "Clinical Response and Pharmacokinetics :from a Phase 1 Study of an Active Dosing Schedule ofFlavopiridol in Relapsed Chronic Lymphocytic Leukemia," Blood, 113(12):2637-2645 (2009).

Presiler et al., "Assessment of c-myc Expression in Individual Leukemic Cells," Leuk Res, 12(6): 507-516 (1988).

Ptashne, "Binding Reactions: Epigenetic Switches, Signal Transduction And Cancer," Current Biology, 19(6):R234-R241 (2009).

Quinn et al., "A homogeneous method for investigation of methylation-dependent protein-protein interactions in epigenetics," Nucleic Acids Res, 38(2):el 1(1-10) (2010).

Rahl et al., "c-Myc Regulates Transcriptional Pause Release," Cell, 141 :432-445 (2010).

Roberts et al., A Bead-Based Proximity Assay for BRD4 Ligand Discovery. Curr Protoc Chem Biol. Dec. 2, 2015;7(4):263-78. doi: 10.1002/9780470559277.ch150024.

Santillan et al., "Bromodomain and Histone Acetyltransferase Domain Specificities Control Mixed Lineage Leukemia Phenotype," Cancer Res, 66(20):10032-10039 (2006).

Schindler et al., "Structural mechanism for STI-571 Inhibition of Abelson Tyrosine kinase. Science," 289:1938-1942 (2000).

Schreiber et al., "Signaling Network Model of Chromatin," Cell, 111:771-778 (2002).

Schroder et al., Two-pronged binding with bromodomain-containing protein 4 liberates positive transcription elongation factor b from inactive ribonucleoprotein complexes. J Biol Chem. Jan. 6, 2012;287(2):1090-9. doi: 10.1074/jbc.M111.282855. Epub Nov. 14, 2011.

Seyrig et al., "Effects of a Chronic Administration of Two Benzodiazepines on Food Intake in Rats Given a Highly Palatable Diet," Pharmacology Biochemistly & Behavior, 25:913-918 (1986).

Shang et al., "The First Bromodomain of Brdt, a Testis-Specific Member of the BET Sub-Family of Double-Bromodomain-Containing Proteins, is Essential for Male Germ Cell Differentiation," Development, 134: 3507-3515 (2007).

Smith et al., The Bromodomain: A New Target in Emerging Epigenetic Medicine. ACS Chem Biol. Mar. 18, 2016;11(3):598-608. doi: 10.1021/acschembio.5b00831. Epub Dec. 3, 2015.

Tanaka et al., Inhibitors of emerging epigenetic targets for cancer therapy: a patent review (2010-2014). Pharm Pat Anal. 2015;4(4):261-84. doi: 10.4155/ppa.15.16.

Taskinen et al., "A High Tumor-Associated Macrophage Content Predicts Favorable Outcome in Follicular Lymphoma Patients Treated with Rituximab and Cyclophosphamide-Doxorubicin-Vincristine-Prednisone," Clin Cancer Res, 13(19): 5784-5785 (2007).

Verma et al., Identification of Potent, Selective, Cell-Active Inhibitors of the Histone Lysine Methyltransferase EZH2. ACS Med Chem Lett. Oct. 19, 2012;3(12):1091-6. Doi: 10.1021/ml3003346. eCollection 2012.

Vollmuth et al., "Structures of the dual bromodomains of the P-TEFb-activating protein Brd4 at atomic resolution," J Biol Chem, 284:36547-36556 (2009).

Von Voigtlander et al., "Alprazolam: Review of Pharmacological, Pharmacokinetic and Clinical Data," Drug Development Research, 6:1-12 (1985).

Wang et al., "Brd2 Disruption in Mice Causes Severe Obesity Without Type 2 Diabetes," Biochem. J., 425:71-83 (2010).

Wang et al., A seamless trespass: germ cell migration across the seminiferous epithelium during spermatogenesis. J Cell Biol. Aug. 13, 2007;178(4):549-56.

Wehner et al., Effects of natalizumab, an alpha4 integrin inhibitor, on fertility in male and female guinea pigs. Birth Defects Res B Dev Reprod Toxicol. Apr. 2009;86(2):108-16. doi: 10.1002/bdrb.20191.

Yang et al., "Brd4 recruits P-TEFb to chromosomes at late mitosis to promote G1 gene expression and cell cycle progression," Mol Cell Biol, 28(3):967-976 (2008).

Yang et al., "Multisite Protein Modification and Intramolecular Signaling," Oncogene, 24:1653-1662 (2005).

Yang et al., Recruitment of P-TEFb for stimulation of transcriptional elongation by the bromodomain protein Brd4. Mol Cell. Aug. 19, 2005;19(4):535-45.

You et al., "Kaposi's sarcoma-associated herpesvirus latency-associated nuclear antigen interacts with bromodomain protein Brd4 on host mitotic chromosomes," J Virol 80, 8909- 8919, (2006).

You et al., "Regulation of Aurora B Expression by the Bromodomain Protein Brd4," Mol Cell Biol, 29:5094-5103 (2009).

Zeng et al., Bromodomain: an acetyl-lysine binding domain. FEBS Lett. Feb. 20, 2002;513(1):124-8.

Zhang et al., "Down-Regulation of NF-κB Transcriptional Activity in HIV-Associated Kidney Disease by BRD4 Inhibition," J. Biol Chem, 287(34):28840-28851 (2012).

Zhang et al., "Down-Regulation of NF-κB Transcriptional Activity in HIV-Associated Kidney Disease by BRD4 Inhibition," J. Biol Chem, 287(46):38956 (2012).

Zhao et al., "Research Development on Fusion Protein Transcription Factor siRNA Specifically Targeting Leukemia," Sciencepaper• Online: 1-6 and J. J Med Res., 39(2):6-9 (Feb. 2010) (English-language translation entitled "Progiess of Research on siRNA that Targets Leukemia Specific Transcription Regulation Factor Fusion Proteins," pp. 1-10).

Zuber et al., "RNAi Screen Identifies Brd4 as a Therapeutic Target in Acute Myeloid Leukaemia," Nature: 478: 524-528 (2011), with "Supplementary Information" from www.nature.com/nature, pp. 1-33.

Zuercher et al., Identification and structure-activity relationship of phenolic acyl hydrazones as selective agonists for the estrogen-related orphan nuclear receptors ERRbeta and ERRgamma.. J Med Chem. May 5, 2005;48(9):3107-9.

International Preliminary Report on Patentability for PCT/US2016/63502, dated Jun. 7, 2018.

Extended European Search Report for EP 16845187.0, dated Jun. 25, 2019.

Extended European Search Report for EP 16845148.2, dated Jul. 16, 2019.

Extended European Search Report for EP16839229.1, dated Aug. 30, 2019.

Partial Supplementary European Search Report for EP 16845148.2, dated Mar. 14, 2019.

Partial Supplementary European Search Report for EP 16845187.0, dated Mar. 18, 2019.

Partial Supplementary European Search Report for EP 16839229.1 dated May 22, 2019.

[No Author Listed] CAS Registry STN No. 1241725-90-5; Sep. 16, 2010.

[No Author Listed] CAS Abstract and Indexed Compounds U.S. Pat. No. 5,712,274; 1998. 19 pages.

[No Author Listed] STN Database Registry No. 1245644-45-4; Oct. 6, 2010.

[No Author Listed] STN Database Registry No. 1245645-74-2; Oct. 6, 2010.

[No Author Listed] STN Database Registry No. 1245645-85-5; Oct. 6, 2010.

(56) References Cited

OTHER PUBLICATIONS

[No Author Listed] CAS Abstract and Indexed Compound EP 368175; 1990. Accession No. 1990:591406. Weber et al.

[No Author Listed] CAS Abstract and Indexed Compound WO 2017/030814; 2017. Accession No. 2017:310173. Qian et al.

Chung et al., Small molecule bromodomain inhibitors: extending the druggable genome. Prog Med Chem. 2012;51(Chapter 1):1-21, 48-55. doi: 10.1016/B978-0-12-396493-9.00001-7.

Communication to CAS RN 130066-84-1 in EP 368175. 2019. Weber et al.

Eikel et al., Liquid extraction surface analysis mass spectrometry (LESA-MS) as a novel profiling tool for drug distribution and metabolism analysis: the terfenadine example. Rapid Commun. Mass Spectrom. 2011, 25, 3587-3596.

Hsu et al., Effects of flavonoids and phenolic acids on the inhibition of adipogenesis in 3T3-L1 adipocytes. J Agric Food Chem. Oct. 17, 2007;55(21):8404-10. Epub Sep. 20, 2007.

Illendula et al., Chemical biology. A small-molecule inhibitor of the aberrant transcription factor CBFβ-SMMHC delays leukemia in mice. Science. Feb. 13, 2015;347(6223):779-84. doi: 10.1126/science.aaa0314.

Kim et al., Substrate and functional diversity of lysine acetylation revealed by a proteomics survey. Mol Cell. Aug. 2006;23(4):607-18.

Picaud et al., RVX-208, an inhibitor of BET transcriptional regulators with selectivity for the second bromodomain. Proc Natl Acad Sci U S A. Dec. 3, 2013;110(49):19754-9. doi: 10.1073/pnas.1310658110. Epub Nov. 18, 2013.

Shaikh, The changing face of antihistamines and cardiac adverse drug reactions: a clinical perspective. J Indian Med Assoc. Jul. 2000;98(7):397-9.

Sterner et al., Acetylation of histones and transcription-related factors. Microbiol Mol Biol Rev. Jun. 2000;64(2):435-59.

Winter et al., Phthalimide conjugation as a strategy for in vivo target protein degradation. Science. Jun. 19, 2015;348(6241):1376-1381.

Zhang et al., Preparation of Small-Molecule Microarrays by trans-Cyclooctene Tetrazine Ligation and Their Application in the High-Throughput Screening of Protein-Protein Interaction Inhibitors of Bromodomains. Angewandte Chemie International Edition. Nov. 4, 2013;52(52):14060-14064.

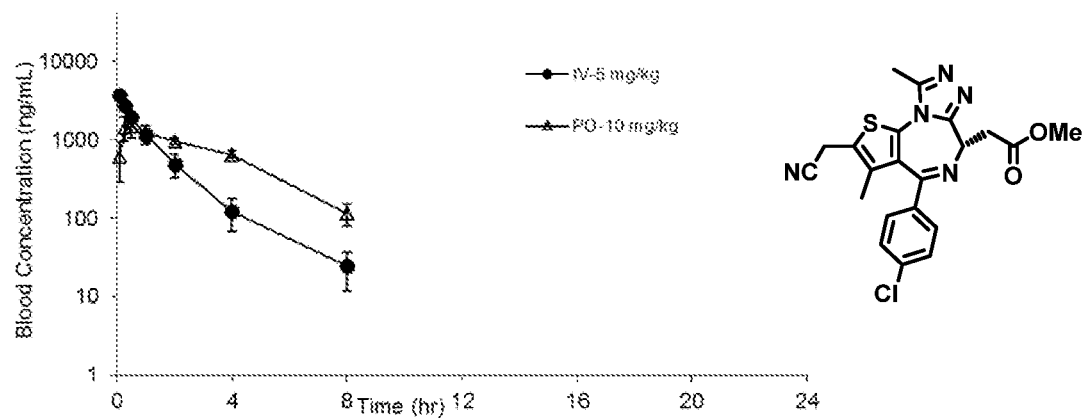
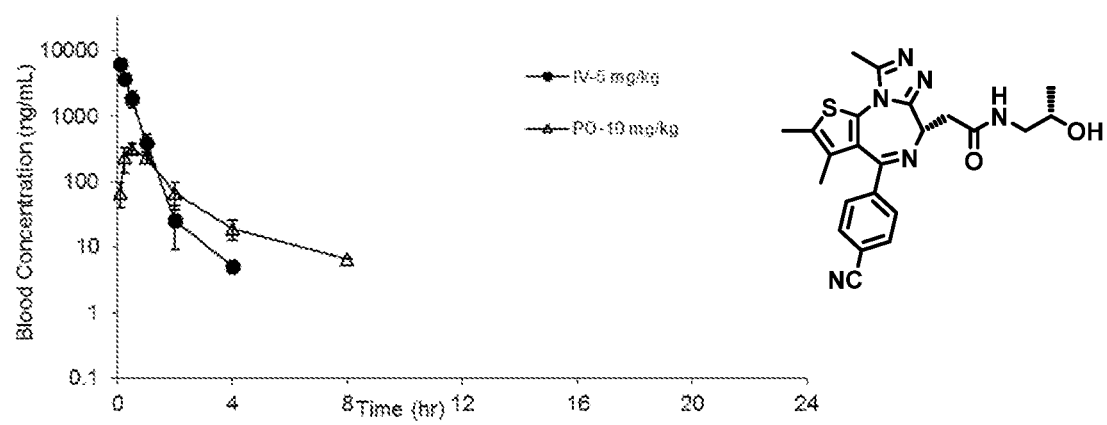
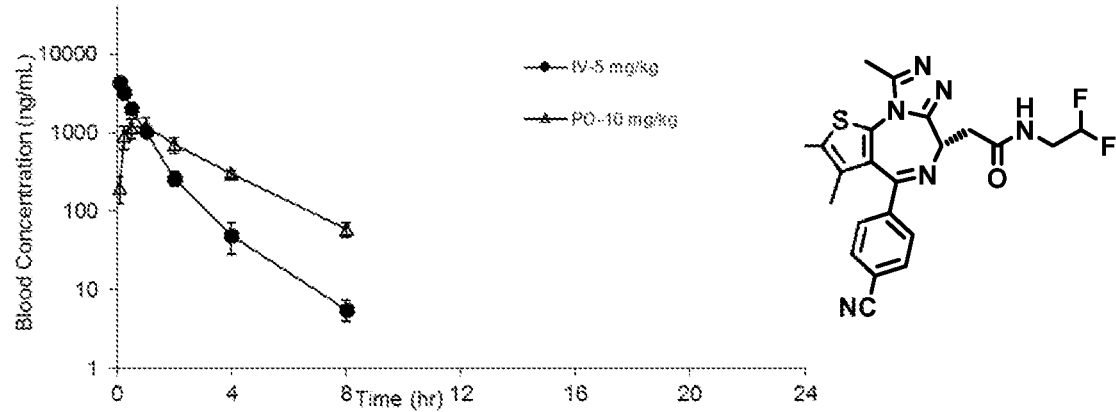

CYANO THIENOTRIAZOLODIAZEPINES AND USES THEREOF

RELATED APPLICATIONS

This application is a national stage filing under 35 U.S.C. § 371 of international PCT application, PCT/US2016/051107, filed Sep. 9, 2016, which claims priority under 35 U.S.C. § 119(e) to U.S. Provisional Application, U.S. Ser. No. 62/217,521, filed Sep. 11, 2015, each of which is incorporated herein by reference.

BACKGROUND

Bromodomain-containing proteins are of substantial biological interest, as components of transcription factor complexes and determinants of epigenetic memory. For example, the bromo and extra terminal (BET) protein family (e.g., bromodomain-containing protein 2 (BRD2), bromodomain-containing protein 3 (BRD3), bromodomain-containing protein 4 (BRD4), and bromodomain testis-specific protein (BRDT)) shares a common domain architecture featuring two amino-terminal bromodomains that exhibit high levels of sequence conservation, and a more divergent carboxy-terminal recruitment domain (Filippakopoulos et al., Nature 2010, 468, 1067-1073). BRD2 and BRD3 are reported to associate with histones along actively transcribed genes and may be involved in facilitating transcriptional elongation (Leroy et al., Mol. Cell. 2008, 30, 51-60). It has also been reported that BRD4 or BRD3 may fuse with nuclear protein in testis (NUT), forming novel fusion oncogenes BRD4-NUT or BRD3-NUT, in a highly malignant form of epithelial neoplasia (French et al., Cancer Res., 2003, 63, 304-307; French et al., J. Clin. Oncol. 2004, 22, 4135-4139). Data suggests that BRD-NUT fusion proteins contribute to carcinogenesis (French et al., Oncogene 2008, 27, 2237-2242). BRDT is uniquely expressed in the testes and ovary. All family members of BET have been reported to have some function in controlling or executing aspects of the cell cycle and have been shown to remain in complex with chromosomes during cell division, suggesting a role in the maintenance of epigenetic memory. In addition, some viruses make use of BET proteins to tether their genomes to the host cell chromatin, as part of the process of viral replication (You et al., Cell 2004, 117, 349-360). BRD4 appears to be involved in the recruitment of the pTEF-b complex to inducible genes, resulting in phosphorylation of RNA polymerase and increased transcriptional output (Hargreaves et al., Cell 2009, 138, 129-145). In humans, BRD2, BRD3, BRD4, and BRDT exhibit similar gene arrangements, domain organizations, and some functional properties (Wu et al., J. Biol. Chem. 2007, 282, 13141-13145).

SUMMARY OF THE INVENTION

Recently, compounds have been reported to be bromodomain binding agents, e.g., international PCT publications WO 2012/075383, WO 2011/054553, WO 2011/054841, WO 2011/054844, WO 2011/054845, WO 2011/054846, WO 2011/054848, WO 2011/143669, and WO 2011/161031. Moreover, Japanese patent application publication JP 2008/156311 discloses a benzimidazole derivative that is a BRD2 bromodomain binding agent and has been found useful in treating viral infections and inhibiting viral replication. International PCT publication WO 2009/084693 discloses a series of thienotriazolodiazepine derivatives that inhibit the binding between an acetylated histone and a bromodomain-containing protein which are useful as anti-cancer agents. International PCT publication WO 2011/054843 suggests compounds which inhibit the binding of a bromodomain with its cognate acetylated proteins may be useful in the treatment of autoimmune and inflammatory diseases. However, there remains a need for additional potent and safe bromodomain binders.

The present invention provides compounds of Formulae (I) and (II). In certain embodiments, a compound of Formula (I) or (II) comprise a cyano group (i.e., —C≡N). The compounds described herein may to be binders of transcription factors, such as bromodomain-containing proteins (e.g., BET proteins) and may be useful in male contraception and in treating and/or preventing a wide range of diseases (e.g., diseases associated with bromodomains, diseases associated with the activity (e.g., aberrant activity) of bromodomains, diseases associated with bromodomain-containing proteins, and disease associated with the activity (e.g., aberrant activity) of bromodomain-containing proteins). Diseases that may be treated and/or prevented by the methods of the disclosure include, but are not limited to, proliferative diseases (e.g., cancers, benign neoplasms, pathological angiogenesis, inflammatory diseases, and autoimmune diseases), cardiovascular diseases, viral infections, fibrotic diseases, neurological diseases, metabolic diseases, endocrine diseases, and radiation poisoning. Also provided in the present disclosure are pharmaceutical compositions, kits, methods, and uses including or using a compound described herein.

In one aspect, the present invention provides compounds of Formula (I):

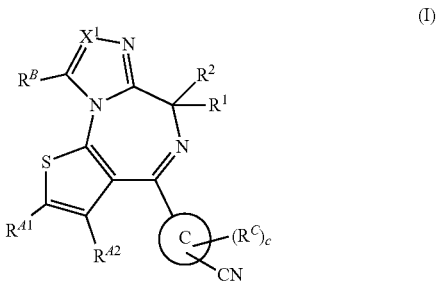

(I)

and pharmaceutically acceptable salts, solvates, hydrates, polymorphs, co-crystals, tautomers, stereoisomers, isotopically labeled derivatives, and prodrugs thereof.

In one aspect, the present invention provides compounds of Formula (II):

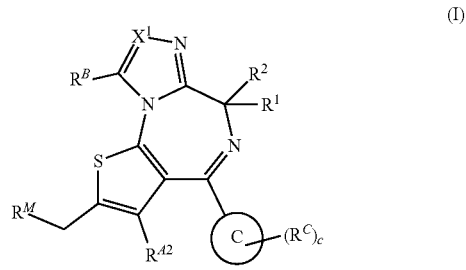

(I)

and pharmaceutically acceptable salts, solvates, hydrates, polymorphs, co-crystals, tautomers, stereoisomers, isotopically labeled derivatives, and prodrugs thereof.

In still another aspect, the present disclosure provides pharmaceutical compositions including a compound described herein (e.g., a compound of Formula (I) or (II)), and optionally a pharmaceutically acceptable excipient. In certain embodiments, the pharmaceutical compositions described herein include a therapeutically or prophylactically effective amount of a compound described herein. The pharmaceutical composition may be useful for treating and/or preventing a disease in a subject in need thereof. The pharmaceutical composition may also be useful in inhibiting the replication of a virus, in killing a virus, in inhibiting the activity of a bromodomain-containing protein, in inhibiting the activity of a bromodomain, in inhibiting the binding of a bromodomain of a bromodomain-containing protein to an acetylated lysine residue of a histone or other protein, in modulating (e.g., inhibiting) transcriptional elongation, in modulating (e.g., down-regulating or inhibiting) the expression (e.g., transcription) of a gene that is regulated by a bromodomain-containing protein, in inducing apoptosis, and/or inducing G1 arrest, in a subject or cell.

In certain embodiments, the disease described herein is associated with the activity (e.g., aberrant activity, increased activity) of a bromodomain-containing protein. In certain embodiments, the disease is associated with the function (e.g., dysfunction) of a bromodomain-containing protein. In certain embodiments, the disease is associated with the activity (e.g., aberrant activity, increased activity) of a bromodomain. In certain embodiments, the disease is associated with the function (e.g., dysfunction) of a bromodomain.

In certain embodiments, the disease is a proliferative disease (e.g., cancer, benign neoplasm, pathological angiogenesis, an inflammatory disease, or an autoimmune disease), cardiovascular disease, viral infection, fibrotic disease, neurological disease, metabolic disease, endocrine disease, or radiation poisoning.

Another aspect of the present disclosure relates to methods of treating a disease in a subject in need thereof.

In another aspect, the present disclosure provides methods of preventing a disease in a subject in need thereof.

Another aspect of the present disclosure relates to methods of reducing the risk of developing a disease in a subject in need thereof.

Another aspect of the present disclosure relates to methods of inhibiting the replication of a virus (e.g., human immunodeficiency virus (HIV), human papillomavirus (HPV), hepatitis C virus (HCV), herpes simplex virus (HSV), Ebola virus, and influenza virus).

Another aspect of the present disclosure relates to methods of killing a virus (e.g., human immunodeficiency virus (HIV), human papillomavirus (HPV), hepatitis C virus (HCV), herpes simplex virus (HSV), Ebola virus, and influenza virus).

In another aspect, the present disclosure provides methods of inhibiting the activity of a bromodomain-containing protein in a subject or cell. In certain embodiments, the activity of a bromodomain-containing protein is aberrant or unwanted activity (e.g., an increased activity) of the bromodomain-containing protein. In certain embodiments, the activity of the bromodomain-containing protein is selectively inhibited (e.g., when compared to the activity of a kinase that is different from the bromodomain-containing protein) by the methods.

In yet another aspect, the present disclosure provides methods of inhibiting the activity of a bromodomain in a subject or a biological sample. In certain embodiments, the activity of a bromodomain being inhibited is aberrant or unwanted activity (e.g., an increased activity) of the bromodomain.

In yet another aspect, the present disclosure provides methods of inhibiting the binding of a bromodomain to an acetylated lysine residue of a second protein (e.g., histone) in a subject or biological sample. In certain embodiments, the second protein is a protein that includes at least one acetylated lysine residue.

In still another aspect, the present disclosure provides methods of modulating the expression (e.g., transcription) of a gene that is regulated by a bromodomain-containing protein in a subject or biological sample. In certain embodiments, the methods of modulating the expression (e.g., transcription) of a gene are methods of down-regulating or inhibiting the expression (e.g., transcription) of the gene. The method may result in decreased levels of a gene product (e.g., RNA, protein) in a cell.

In still another aspect, the present disclosure provides methods of modulating (e.g., inhibiting) transcriptional elongation in a cell of a subject or biological sample.

Another aspect of the disclosure relates to methods of inducing apoptosis (e.g., apoptosis of a cancer cell) in a cell of a subject or biological sample.

Another aspect of the disclosure relates to methods of method for inducing G1 arrest in a cell of a subject or biological sample.

The methods of the present disclosure include administering to the subject an effective amount of a compound or pharmaceutical composition described herein. The methods of the present disclosure include contacting a biological sample (e.g., a cell) with an effective amount of a compound or pharmaceutical composition described herein. The methods of the present disclosure include contacting a virus with an effective amount of a compound or pharmaceutical composition described herein. In certain embodiments, the effective amount is a therapeutically effective amount. In certain embodiments, the effective amount is a prophylactically effective amount. In certain embodiments, the methods of the present disclosure further include administering to the subject an additional pharmaceutical agent in combination with a compound or pharmaceutical composition described herein. In certain embodiments, the methods of the present disclosure further include contacting a biological sample (e.g., a cell) with an additional pharmaceutical agent in combination with a compound or pharmaceutical composition described herein. In certain embodiments, the methods of the present disclosure further include contacting a virus with an additional pharmaceutical agent in combination with a compound or pharmaceutical composition described herein. In certain embodiments, the combination of the pharmaceutical agent and the compound or pharmaceutical composition described herein is synergistic.

Another aspect of the disclosure relates to methods of screening a library of compounds to identify a compound that is useful in a method of the disclosure.

Another aspect of the present disclosure relates to kits comprising a container with a compound or pharmaceutical composition described herein. The kits described herein may include a single dose or multiple doses of the compound or pharmaceutical composition described herein. The provided kits may be useful in a method of the disclosure. In certain embodiments, the kit further includes instructions for using the kit.

In yet another aspect, the present disclosure provides compounds and pharmaceutical compositions described herein for use in a method of the disclosure.

The present application refers to various issued patents, published patent applications, journal articles, and other publications, all of which are incorporated herein by reference. The details of one or more embodiments of the disclosure are set forth herein. Other features, objects, and advantages of the disclosure will be apparent from the Detailed Description, the Figures, the Examples, and the Claims.

Definitions

Chemical Terms

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The disclosure additionally encompasses compounds as individual isomers substantially free of other isomers, and alternatively, as mixtures of various isomers.

In a formula, ⁓ is a single bond where the stereochemistry of the moieties immediately attached thereto is not specified, - - - is absent or a single bond, and ═ or ≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7, carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CHF_2$, —$CH_2F$, —$CF_3$, —$CH_2CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-7}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$ or

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 0.1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{7-10}$ alkynyl. In certain embodiments, the heteroalkynyl group is a substituted hetero$C_{1-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur. Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl, groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g.; 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+X^-$, —N($R^{ee}$)$R^{ff}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2R^{ee}$, —SO$_2$N($R^{ff}$)$_2$, —SO$_2R^{ee}$, —SO$_2$O$R^{ee}$, —OSO$_2R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —NH$_2$($C_{1-6}$ alkyl)$^+X^-$, —NH$_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2C_{1-6}$ alkyl, —SO$_2$O$C_{1-6}$ alkyl, —OSO$_2C_{1-6}$ alkyl, —SO$C_{1-6}$ alkyl, —Si($C_{1-6}$ alkyl)$_3$, —OSi($C_{1-6}$ alkyl)$_3$ —C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$ alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from -O$R^{aa}$, —ON($R^{bb}$)$_2$, —OC(=O)S$R^{aa}$, —OC(=O)$R^{aa}$, —OCO$_2R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N($R^{bb}$)$_2$, —OS(=O)$R^{aa}$, —OSO$_2R^{aa}$, —OSi($R^{aa}$)$_3$, —OP($R^{cc}$)$_2$, —OP($R^{cc}$)$_3^+X^-$, —OP(O$R^{cc}$)$_2$, —OP(O$R^{cc}$)$_3^+X^-$, —OP(=O)($R^{aa}$)$_2$, —OP(=O)(O$R^{cc}$)$_2$, and —OP(=O)(N($R^{bb}$))$_2$, wherein $X^-$, $R^{aa}$, $R^{bb}$, and $R^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC (=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(N(R$^{bb}$)$_2$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(N(R$^{bb}$)$_2$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, hetcroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethylcarbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methylcarbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, 1-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $-S(=O)_2R^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mtc), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). In certain embodiments, a nitrogen protecting group described herein is Bn, Boc, Cbz, Fmoc, trifluoroacetyl, triphenylmethyl, acetyl, or Ts.

In certain embodiments, the substituent present on an oxygen atom is an oxygen protecting group (also referred to herein as an "hydroxyl protecting group"). Oxygen protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2^+X^-$, $-P(OR^{cc})_2$, $-P(OR^{cc})_3^+X^-$, $-P(=O)(R^{aa})_2$, $-P(=O)(OR^{cc})_2$, and $-P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxy tetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). In certain embodiments, an oxygen protecting group described herein is silyl, TBDPS, TBDMS, TIPS, TES, TMS, MOM, THP, t-Bu, Bn, allyl, acetyl, pivaloyl, or benzoyl.

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})$ $R^{aa}$, $-C(=NR^{bb})OR^{aa}$, $-C(=NR^{bb})N(R^{bb})_2$, $-S(=O)$ $R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)$ $(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference. In certain embodiments, a sulfur protecting group described herein is acetamidomethyl, t-Bu, 3-nitro-2-pyridine sulfenyl, 2-pyridine-sulfenyl, or triphenylmethyl.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3{}^-$, ClO$_4{}^-$, OH$^-$, H$_2$PO$_4{}^-$, HCO$_3{}^-$, HSO$_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4{}^-$, PR$_4{}^-$, PF$_6{}^-$, AsF$_6{}^-$, SbF$_6{}^-$, B[3,5-(CF$_3$)$_2$C$_6$H$_3$]$_4{}^-$, B(C$_6$F$_5$)$_4{}^-$, BPh$_4{}^-$, Al(OC (CF$_3$)$_3$)$_4$, and carborane anions (e.g., CB$_{11}$H$_{12}{}^-$ or (HCB$_{11}$Me$_5$Br$_6$)$^-$). Exemplary counterions which may be multivalent include CO$_3{}^{2-}$, HPO$_4{}^{2-}$, PO$_4{}^{3-}$, B$_4$O$_7{}^{2-}$, SO$_4{}^{2-}$, S$_2$O$_3{}^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group, can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), —OR$^{aa}$ (when the O atom is attached to a carbonyl group, wherein R$^{aa}$ is as defined herein), —O(C=O)R$^{LG}$, or —O(SO)$_2$R$^{LG}$ (e.g., tosyl, mesyl, besyl), wherein R$^{LG}$ is optionally substituted alkyl, optionally substituted aryl, or optionally substituted heteroaryl. In some cases, the leaving group is a halogen. In some embodiments, the leaving group is I. Examples of suitable leaving groups include, but are not limited to, halides (such as chloride, bromide, or iodide), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, haloformates, —NO$_2$, trialkylammonium, and aryliodonium salts. In certain embodiments, the leaving group is a sulfonic acid ester. In certain embodiments, the sulfonic acid ester comprises the formula —OSO$_2$R$^{LG1}$ wherein R$^{LG1}$ is selected from the group consisting alkyl optionally, alkenyl optionally substituted, heteroalkyl optionally substituted, aryl optionally substituted, heteroaryl optionally substituted, arylalkyl optionally substituted, and heteroarylalkyl optionally substituted. In certain embodiments, R$^{LG1}$ is substituted or unsubstituted C$_1$-C$_6$ alkyl. In certain embodiments, R$^{LG1}$ is methyl. In certain embodiments, $R^{LG1}$ is —$CF_3$. In certain embodiments, $R^{LG1}$ is substituted or unsubstituted aryl. In certain embodiments, $R^{LG1}$ is substituted or unsubstituted phenyl. In certain embodiments $R^{LG1}$ is:

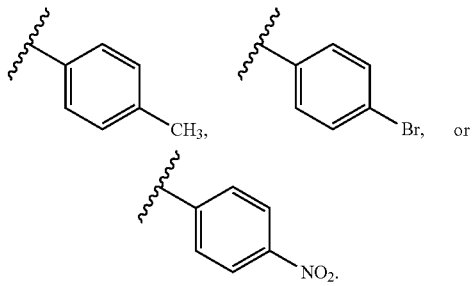

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium, and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal contains a compound of the present invention and one or more other component, including but not limited to, atoms, ions, molecules, or solvent molecules. In certain embodiments, a co-crystal contains a compound of the present invention and one or more solvent molecules. In certain embodiments, a co-crystal contains a compound of the present invention and one or more acid or base. In certain embodiments, a co-crystal contains a compound of the present invention and one or more components related to said compound, including not limited to, an isomer, tautomer, salt, solvate, hydrate, synthetic precursor, synthetic derivative, fragment or impurity of said compound.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is at most about 1,000 g/mol, at most about 900 g/mol, at most about 800 g/mol, at most about 700 g/mol, at most about 600 g/mol, at most about 500 g/mol, at most about 400 g/mol, at most about 300 g/mol, at most about 200 g/mol, or at most about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and at most about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present disclosure.

A "protein," "peptide," or "polypeptide" comprises a polymer of amino acid residues linked together by peptide bonds and refers to proteins, polypeptides, and peptides of any size, structure, or, function. Typically, a protein will be at least three amino acids long. A protein may refer to an individual protein or a collection of proteins. Proteins described herein preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The term "histone" refers to highly alkaline proteins found in eukaryotic cell nuclei that package and order the DNA into structural units called nucleosomes. They are the chief protein components of chromatin, acting as spools around which DNA winds, and play a role in gene regulation. In certain embodiments, the histone is histone H1 (e.g., histone H1F, histone H1H1). In certain embodiments, the histone is histone H2A (e.g., histone H2AF, histone H2A1, histone H2A2). In certain embodiments, the histone is histone H2B (e.g., histone H2BF, histone H2B1, histone H2B2). In certain embodiments, the histone is histone H3 (e.g., histone H3A1, histone H3A2, histone H3A3). In certain embodiments, the histone is histone H4 (e.g., histone H41, histone H44).

The term "bromodomain" refers to a protein domain that recognizes acetylated lysine residues such as those on the N-terminal tails of histones. In certain embodiments, a bromodomain of a BET protein comprises about 110 amino acids and shares a conserved fold comprising a left-handed bundle of four alpha helices linked by diverse loop regions that interact with chromatin. In certain embodiments, the bromodomain is ASH1L (GenBank ID: gi|8922081), ATAD2 (GenBank ID: gi|24497618), BAZ2B (GenBank ID: gi|7304923), BRD1 (GenBank ID: gi|11321642), BRD2(1) (GenBank ID: gi|4826806), BRD2(2) (GenBank ID: gi|4826806), BRD3(1) (GenBank ID: gi|11067749), BRD3(2) (GenBank ID: gi|11067749), BRD4(1) (GenBank ID: gi|19718731), BRD4(2) (GenBank ID: gi|19718731), BRD9 (GenBank ID: gi|57770383), BRDT(1) (GenBank ID: gi|46399198), BRPF1 (GenBank ID: gi|51173720), CECR2 (GenBank ID: gi|148612882), CREBBP (GenBank ID: gi|4758056), EP300 (GenBank ID: gi|50345997), FALZ (GenBank ID: gi|38788274), GCN5L2 (GenBank ID: gi|10835101), KIAA1240 (GenBank ID: gi|51460532), LOC93349 (GenBank ID: gi|134133279), PB1(1) (GenBank ID: gi|30794372), PB1(2) (GenBank ID: gi|30794372), PB1(3) (GenBank ID: gi|30794372), PB1(5) (GenBank ID: gi|30794372), PB1(6) (GenBank ID: gi|30794372), PCAF (GenBank ID: gi|40805843), PHIP(2) (GenBank ID: gi|34996489), SMARCA2 (GenBank ID: gi|48255900), SMARCA4 (GenBank ID: gi|21071056), SP140 (GenBank ID: gi|52487219), TAF1(1) (GenBank ID: gi|20357585), TAF1(2) (GenBank ID: gi|20357585), TAF1L(1) (GenBank ID: gi|24429572), TAF1L(2) (GenBank ID: gi|24429572), TIF1 (GenBank ID: gi|14971415), TRIM28 (GenBank ID: gi|5032179), or WDR9(2) (GenBank ID: gi|16445436).

The term "bromodomain-containing protein" or "bromodomain protein" refers to a protein, whether wild-type or mutant, natural or synthetic, truncated or complete, or a variant thereof, that possesses the minimum amino acid sequence sufficient for a functional bromodomain capable of mediating molecular recognition of acetyl-lysine of acetylated lysine residues on a second protein (e.g., a histone), such as on the tails of histones. Bromodomain-containing proteins include, for example, fusion proteins comprising a bromodomain and an additional portion having a desired functionality (e.g., a reporter portion).

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The terms "disease," "disorder," and "condition" are used interchangeably herein.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "administer," "administering," or "administration" refers to implanting, absorbing, ingesting, injecting, inhaling, or otherwise introducing a compound described herein, or a composition thereof, in or on a subject.

The terms "condition," "disease," and "disorder" are used interchangeably.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic, agent. In certain embodiments, a therapeutically effective amount is effective for inhibiting the activity of a bromodomain-containing protein. In certain embodiments, a therapeutically effective amount is effective for treating a disease described herein. In certain embodiments, a therapeutically effective amount is effective for inhibiting the activity of a bromodomain-containing protein and for treating a disease described herein.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for inhibiting the activity of a bromodomain-containing protein. In certain embodiments, a prophylactically effective amount is effective for preventing a disease described herein. In certain embodiments, a prophylactically effective amount is effective for inhibiting the activity of a bromodomain-containing protein and for preventing a disease described herein.

The term "inhibition", "inhibiting", "inhibit," or "inhibitor" refer to the ability of a compound to reduce, slow, halt or prevent activity of a particular biological process (e.g., activity of a bromodomain and/or a bromodomain-containing protein) in a cell relative to vehicle. In some embodiments, the term refers to a reduction of the level of enzyme activity, e.g., (bromodomain, bromodomain-containing protein activity), to a level that is statistically significantly lower than an initial level, which may, for example, be a baseline level of enzyme activity. In some embodiments, the term refers to a reduction of the level of enzyme activity, e.g., (bromodomain, bromodomain-containing protein) activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

When a compound, pharmaceutical composition, method, use, or kit is referred to as "selectively," "specifically," or "competitively" binding a first protein or a first chromatin, the compound, pharmaceutical composition, method, use, or kit binds the first protein or the first chromatin with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or second chromatin that is different from the first protein and the first chromatin. When a compound, pharmaceutical composition, method, use, or kit is referred to as "selectively," "specifically," or "competitively" modulating (e.g., increasing or inhibiting) the activity of a bromodomain-containing protein, the compound, pharmaceutical composition, method, use, or kit modulates the activity of the bromodomain-containing protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the bromodomain-containing protein.

The term "aberrant activity" refers to activity deviating from normal activity. The term "increased activity" refers to activity higher than normal activity.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, diseases associated with angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cello, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary*, 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck Squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma; testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type 1), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UTP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, post-surgical inflammation.

An "autoimmune disease" refers to a disease arising from an inappropriate immune response of the body of a subject against substances and tissues normally present in the body. In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid, arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and Mental illness, include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders: Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type TT diabetes, gestational diabetes), hyperglycemia, hyperinsulinemia, insulin resistance, and obesity.

A "kinase" is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1 g, CaMK2a, CaMK2b, CaMK2d, CaMK2 g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1 g1, CK1 g2, CK1 g2ps, CK1 g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK12, JAK2, JAK22, JAK3, JAK32, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38 g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK, skMLCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, ZC4/NRK.

BRIEF DESCRIPTION OF THE DRAWINGS

The accompanying drawings, which constitute a part of this specification, illustrate several embodiments of the invention and together with the description, serve to explain the principles of the invention.

FIG. 1. Mean whole blood concentration-time profiles for compounds 200 (A), 107 (B), and 109 (C) after intravenous dose at 5 mg/kg or oral dose at 10 mg/kg (N=3) in male CD1 mice.

DETAILED DESCRIPTION OF CERTAIN EMBODIMENTS

The present disclosure provides compounds of Formulae (I) and (II), which bind bromodomains and/or bromodomain-containing proteins. The compounds described herein may be able to bind in a pocket of a bromodomain (e.g., a bromodomain of a bromodomain-containing protein). In certain embodiments, the compounds described herein may bind in the pocket of a bromodomain and disrupt the interaction between the bromodomain binding pocket and an acetylated lysine residue of a second protein (e.g., a histone). In certain embodiments, the compounds described herein bind in the pocket of the bromodomain. The compound described herein may also modulate (e.g., inhibit) the activity of a bromodomain and/or bromodomain-containing protein. Also provided in the present disclosure are pharmaceutical compositions, methods, uses, and kits useful in modulating (e.g., inhibiting) the activity of a bromodomain-containing protein (e.g., a transcription factor). The compounds, pharmaceutical compositions, methods, uses, and kits may be useful in treating and/or preventing diseases associated with a bromodomain, diseases associated with a bromodomain-containing protein, diseases associated with the activity (e.g., aberrant activity) of a bromodomain, and diseases associated with the activity (e.g., aberrant activity) of a bromodomain-containing protein. Exemplary diseases that maybe prevented and/or treated with compounds described herein include proliferative diseases (e.g., cancers, benign neoplasms, pathological angiogenesis, inflammatory diseases, and autoimmune diseases), autoimmune diseases, cardiovascular diseases, viral infections, fibrotic diseases, neurological diseases, metabolic diseases, endocrine diseases, and radiation poisoning. The compounds, pharmaceutical compositions, methods, uses, and kits may also be useful for male contraception and for preventing and/or treating a viral infection (e.g., by inhibiting the replication of a virus, by killing a virus).

Compounds described herein (e.g., compounds of Formulae (I) and (II)) have been found to bind bromodomain-containing proteins. In certain embodiments, the compounds described herein bind to a bromodomain-containing protein. Without wishing to be bound by any particular theory, the compounds described herein are thought to bind in a pocket of a bromodomain of a bromodomain-containing protein. In certain embodiments, the compounds described herein bind in the binding pocket of the bromodomain by mimicking the contact between an acetyl-lysine residue of a second protein (e.g., a histone) and the binding pocket. In certain embodiments, the compounds described herein hind in the binding pocket of the bromodomain. In certain embodiments, the compounds described herein covalently bind to the bromodomain-containing protein. In certain embodiments, the compounds described herein non-covalently bind to the bromodomain-containing protein. In certain embodiments, the compounds described herein reversibly bind to the bromodomain-containing protein. In certain embodiments, the compounds described herein non-reversibly bind to the bromodomain-containing protein. In certain embodiments, the compounds described herein inhibit the activity (e.g., aberrant activity, increased activity) of a bromodomain-containing protein. In certain embodiments, the compounds described herein inhibit the activity (e.g., aberrant activity, increased activity) of a bromodomain. In certain embodiments, the activity of a bromodomain is the ability of the bromodomain to bind an acetylated lysine residue (e.g., an acetylated lysine residue on the NT-terminal tails of histones), which may be part of another protein or peptide. In certain embodiments, the compounds described herein specifically bind to a bromodomain-containing protein (e.g., bind to a bromodomain-containing protein with a higher binding affinity than to a different bromodomain-containing protein and/or to a protein that is not a bromodomain-containing protein). In certain embodiments, the compounds described herein specifically bind to a bromodomain of a bromodomain-containing protein (e.g., hind to a bromodomain of a bromodomain-containing protein with a higher binding affinity than to a non-bromodomain of the bromodomain-containing protein). In certain embodiments, the compounds described herein non-specifically bind to a bromodomain-containing protein (e.g., bind to a bromodomain of the bromodomain-containing protein). In certain embodiments, the compounds described herein reduce transcriptional elongation. In certain embodiments, the compounds described herein disrupt the subcellular localization of a bromodomain-containing protein. In certain embodiments, the compounds described herein reduce chromatin binding. In certain embodiments, the compounds described herein inhibit the formation of a chromatin by reducing the binding of a protein (e.g., histone) to a DNA. In certain embodiments, the compounds described herein inhibit the binding of Histone H4 Kac peptide to a bromodomain of a bromodomain-containing protein. In certain embodiments, the compounds described herein form one or more hydrogen bonds with an evolutionarily conserved asparagine in a bromodomain of a bromodomain-containing protein. In certain embodiments, the asparagine is Asn140 in BRD4(1) and Asn429 in BRD2(2). In certain embodiments, the bromodomain-containing protein is BRD4 or BRD2; and the asparagine is Asn140 in BRD4(1) and Asn429 in BRD2(2). In certain embodiments, the compounds described herein bind competitively with chromatin in a cellular environment. It is thus expected that the compounds described herein may be useful in the treatment of a disease associated with the activity a bromodomain-containing protein (e.g., a proliferative disease).

The compounds described herein may bind bromodomain-containing proteins and may inhibit the activity of the bromodomain-containing proteins. In certain embodiments, the bromodomain-containing protein is a bromo and extra terminal (BET) protein. In certain embodiments, the bromodomain-containing protein is BRD2. In certain embodiments, the bromodomain-containing protein is BRD2(1). In certain embodiments, the bromodomain-containing protein is BRD2(2). In certain embodiments, the bromodomain-containing protein is BRD3. In certain embodiments, the bromodomain-containing protein is BRD3(1). In certain embodiments, the bromodomain-containing protein is BRD3(2). In certain embodiments, the bromodomain-containing protein is BRD4. In certain embodiments, the bromodomain-containing protein is BRD4(1). In certain embodiments, the bromodomain-containing protein is BRD4(2). In certain embodiments, the bromodomain-containing protein is BRDT. In certain embodiments, the bromodomain-containing protein is BRDT(1). In certain embodiments, the bromodomain-containing protein is BRDT(2). In certain embodiments, the bromodomain-containing protein is a TBP (TATA box binding protein)-associated factor protein (TAF). In certain embodiments, the bromodomain-containing protein is TAF1. In certain embodiments, the bromodomain-containing protein is TAF1L. In certain embodiments, the bromodomain-containing protein is CREB-binding protein (CBP). In certain embodiments, the bromodomain-containing protein is E1A binding protein p300 (EP300).

The binding affinity of a compound described herein to a bromodomain-containing protein may be measured by the dissociation constant ($K_d$) value of an adduct of the compound described herein and the bromodomain-containing protein using methods known in the art (e.g., isothermal titration calorimetry (ITC)). In certain embodiments, the adduct comprises the compound described herein and the bromodomain-containing protein, which are bound (e.g., covalently or non-covalently) to each other. In certain embodiments, the $K_d$ value of the adduct is at most about 100 at most about 30 μM, at most about 10 μM, at most about 3 μM, at most about 1 μM, at most about 300 nM, at most about 100 nM, at most about 30 nM, at most about 10 nM, at most about 3 nM, or at most about 1 nM. In certain embodiments, the $K_d$ value of the adduct is at least about 1 nM, at least about 10 nM, at least about 100 nM, at least about 1 μM, at least about 10 μM, or at least about 100 μM. Combinations of the above-referenced ranges (e.g., at most about 10 μM and at least about 1 nM) are also within the scope of the disclosure. Other ranges are also possible. In certain embodiments, the $K_d$ value of the adduct is at most about 10 μM. In certain embodiments, the $K_d$ value of the adduct is at most about 300 nM. In certain embodiments, the $K_d$ value of the adduct is at most about 100 nM.

In certain embodiments, the activity of the bromodomain-containing proteins described herein is inhibited by the compounds described herein. The inhibition of the activity of a bromodomain-containing protein by a compound described herein may be measured by the half maximal inhibitory concentration ($IC_{50}$) value of a compound described herein when the compound described herein, or a pharmaceutical composition thereof, is contacted with the bromodomain-containing protein. In certain embodiments, $IC_{50}$ values are obtained by a competition binding assay. In certain embodiments, $IC_{50}$ values are obtained by a method described herein. In certain embodiments, the $IC_{50}$ value of a compound described herein is at most about 1 mM, at most about 300 μM, at most about 100 μM, at most about 30 μM, at most about 10 μM, at most about 3 μM, at most about 1 μM, at most about 300 nM, at most about 100 nM, at most about 30 nM, at most about 10 nM, at most about 3 nM, or at most about 1 nM. In certain embodiments, the $IC_{50}$ value of a compound described herein is at least about 1 nM, at least about 3 nM, at least about 10 nM, at least about 30 nM, at least about 100 nM, at least about 300 nM, at least about 1 μM, at least about 3 μM, at least about 10 μM, at least about 30 μM, at least about 100 μM, at least about 300 μM, or at least 1 mM. Combinations of the above-referenced ranges (e.g., at most about 300 μM and at least about 1 μM) are also within the scope of the disclosure. Other ranges are also possible. In certain embodiments, the $IC_{50}$ value of a compound described herein is at most about 300 μM. In certain embodiments, the $IC_{50}$ value of a compound described herein is at most about 30 μM. In certain embodiments, the $IC_{50}$ value of a compound described herein is at most about 10 μM.

The compounds described herein may selectively inhibit the activity of a bromodomain-containing protein. In certain embodiments, the compounds described herein selectively inhibit the activity of a bromodomain-containing protein compared to a different bromodomain-containing protein. In certain embodiments, the compounds described herein selectively inhibit the activity of a bromodomain-containing protein compared to a protein that is not a bromodomain-containing protein. In certain embodiments, the compounds described herein selectively inhibit the activity of a bromodomain-containing protein compared to a kinase (e.g., a kinase described herein). In certain embodiments, the compounds described herein selectively inhibit the activity of a bromodomain-containing protein compared to MPS1 (TTK), ERK5 (BMK1, MAPK7), a polo kinase (e.g., polo kinase 1, polo kinase 2, polo kinase 3, polo kinase 4), Ack1, Ack2, Abl, DCAMKL1, ABL1, an Abl mutant, DCAMKL2, ARK5, BRK, MKNK2, FGFR4, TNK1, PLK1, ULK2, PLK4, PRKD1, PRKD2, PRKD3, ROS 1, RPS6KA6, TAOK1, TAOK3, TNK2, Bcr-Abl, GAK, cSrc, TPR-Met, Tie2, MET, FGFR3, Aurora, AxI, Bmx, BTK, c-kit, CHK2, Flt3, MST2, p70S6K, PDGFR, PKB, PKC, Raf, ROCK-H, Rsk1, SGK, TrkA, TrkB, and/or TrkC. In certain embodiments, the compounds described herein selectively inhibit the activity of a bromodomain-containing protein compared to a MAP kinase. In certain embodiments, the compounds described herein selectively inhibit the activity of a bromodomain-containing protein compared to a mitotic spindle kinase. In certain embodiments, the compounds described herein selectively inhibit the activity of a bromodomain-containing protein compared to a polo kinase. In certain embodiments, the compounds described herein selectively inhibit a BET protein. In certain embodiments, the compounds described herein selectively inhibit BRD2. In certain embodiments, the compounds described herein selectively inhibit BRD3. In certain embodiments, the compounds described herein selectively inhibit BRD4. In certain embodiments, the compounds described herein selectively inhibit BRDT. In certain embodiments, the compounds described herein selectively inhibit a TAF protein (e.g., TAF1 or TAF1L), CBP, and/or EP300. In certain embodiments, a compound described herein is a non-selective inhibitor of two or more bromodomain-containing proteins. In certain embodiments, a compound described herein is a non-selective inhibitor of a bromodomain-containing protein and a protein that is not a bromodomain-containing protein.

The selectivity of a compound described herein in inhibiting the activity of a bromodomain-containing protein over a second protein (e.g., a kinase) that is different from the bromodomain-containing protein may be measured by the quotient of the $IC_{50}$ value of the compound described herein in inhibiting the activity of the second protein over the $IC_{50}$ value of the compound described herein in inhibiting the activity of the bromodomain-containing protein. The selectivity of a compound described herein for a bromodomain-containing protein over a second protein may also be measured by the quotient of the $K_d$ value of an adduct of the compound described herein and the second protein over the $K_d$ value of an adduct of the compound described herein and the bromodomain-containing protein. In certain embodiments, the selectivity is at least about 1-fold, at least about 3-fold, at least about 5-fold, at least about 10-fold, at least about 30-fold, at least about 100-fold, at least about 300-fold, at least about 1,000-fold, at least about 3,000-fold, at least about 10,000-fold, at least about 30,000-fold, or at least about 100,000-fold. In certain embodiments, the selectivity is at most about 100,000-fold, at most about 10,000-fold, at most about 1,000-fold, at most about 100-fold, at most about 10-fold, or at most about 1-fold. Combinations of the above-referenced ranges (e.g., at least about 2-fold and at most about 10,000-fold) are also within the scope of the disclosure. Other ranges are also possible. In certain embodiments, the selectivity is at least about 3-fold. In certain embodiments, the selectivity is at least about 10-fold. In certain embodiments, the selectivity is at least about 50-fold. In certain embodiments, the selectivity is at least about 100-fold. In certain embodiments, the selectivity is at least about 1,000-fold.

It is known in the art that a bromodomain-containing protein is implicated in a wide range of diseases. For example, BRD3 and BRD4 are related to BRD3 NUT midline carcinoma and BRD4 NUT midline carcinoma, respectively. BRDT is related to sperm formation, and CBP is related to mixed-lineage leukemia (MLL). Therefore, the compounds described herein are expected to be useful in treating and/or preventing diseases associated with bromodomain-containing proteins or as a male contraceptive.

Compounds of Formula (I) and (II)

In one aspect, the present invention provides compounds of Formula (I):

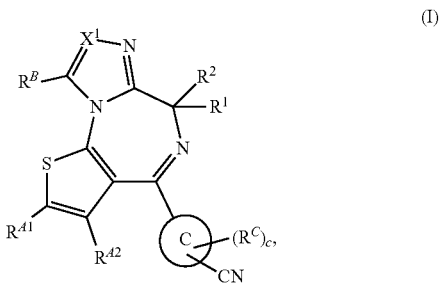

or a pharmaceutically acceptable salt, stereoisomer, tautomer, solvate, hydrate, polymorph, co-crystal, or prodrug thereof, wherein:

$R^{A1}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;

$R^{A2}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;

$X^1$ is N or $CR^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;

$R^B$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;

Ring C is aryl or heteroaryl;

each occurrence of $R^C$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^f$, —$SR^f$, —$N(R^f)_2$, —$NO_2$, or —CN;

c is 0, 1, 2, 3, or 4;

$R^1$ is hydrogen, halogen, optionally substituted alkyl, or —$(CH_2)_nL$, wherein n is 0, 1, 2, 3 or 4, and L is —C(=O)$R^3$, —C(=O)$OR^3$, —C(=O)$NR^3R^4$, —S(=O)$_2R^3$, —S(=O)$_2OR^3$, —S(=O)$_2NR^3R^4$, —$OR^3$, —$NR^3R^4$, —N($R^4$)C(=O)$R^3$, optionally substituted carbocyclyl, optionally substituted heterocyclyl, optionally substituted aryl, or optionally substituted heteroaryl;

$R^2$ is hydrogen, halogen, or optionally substituted alkyl;

each of $R^3$ and $R^4$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or optionally substituted acyl, an oxygen protecting group, or a nitrogen protecting group, or $R^3$ and $R^4$ are joined to form an optionally substituted heterocyclic or optionally substituted heteroaryl ring; and each occurrence of $R^f$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, or a nitrogen protecting group, or two $R^f$ are joined to form an optionally substituted heterocyclic or optionally substituted heteroaryl ring.

In certain embodiments, the compound of Formula (I) is not of formula:

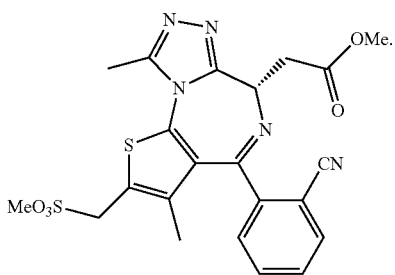

In certain embodiments, the compound of Formula (I) is not of formula:

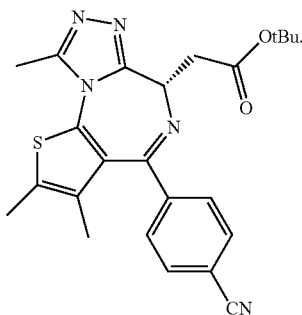 [SMILES: Cc1sc2c(c1C)C(c1ccc(C#N)cc1)=N[C@@H](CC(=O)OC(C)(C)C)c1nnc(C)n1-2]

In certain embodiments, $R^{41}$ is not substituted alkyl. In certain embodiments, $R^{41}$ is not substituted $C_1$ alkyl. In certain embodiments, $R^{41}$ is not sulfonyl substituted alkyl. In certain embodiments, $R^{41}$ is hydrogen, halogen, methyl, optionally substituted $C_{2-6}$ alkyl, optionally substituted alkenyl, optionally substituted alkynyl, optionally substituted carbocyclyl, optionally substituted heterocyclyl, optionally substituted aryl, optionally Substituted heteroaryl, optionally substituted acyl, —$OR^f$, —$SR^f$, —$N(R^f)_2$, —$NO_2$, or —CN.

In certain embodiments, $R^1$ is not —$CH_2C(=O)OR^3$. In certain embodiments, $R^1$ is hydrogen, halogen, or —$(CH_2)_nL$, wherein n is 0, 1, 2, 3 or 4, and L is —C(=O)$R^3$, —C(=O)$NR^3R^4$, —S(=O)$_2R^3$, —S(=O)$_2OR^3$, —S(=O)$_2NR^3R^4$, —$OR^3$, —$NR^3R^4$, —$N(R^4)C(=O)R^3$, optionally substituted carbocyclyl, optionally substituted heterocyclyl, optionally substituted aryl, or optionally substituted heteroaryl, and $R^2$ is hydrogen or halogen.

In certain embodiments, Ring C is not of formula:

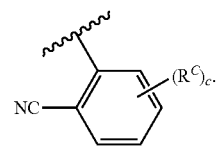

In certain embodiments, Ring C is not of formula:

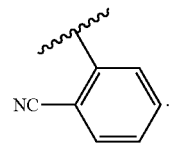

In certain embodiments, compounds of Formula (I) do not include compounds disclosed in any of U.S. Pat. Nos. 5,712,274, 8,044,042, 8,476,260, 8,981,083, WIPO Application No. PCT/US2014/023386, filed Mar. 11, 2014, WIPO Application No. PCT/US2011/036647, filed May 16, 2011, WIPO Application No. PCT/US2011/036667, filed May 16, 2011, WIPO Application No. PCT/US2011/036672, filed May 16, 2011, WIPO Application No. PCT/US2011/036701, filed May 16, 2011, WIPO Application No. PCT/JP2008/073864, filed Dec. 26, 2008, WIPO Application No. PCT/JP1992/001198, Sep. 18, 1992, WIPO Application No. PCT/JP1993/001329, filed Sep. 16, 1993, and WIPO Application No. PCT/JP2006/310709, filed May 30, 2006.

In one aspect, the present invention provides compounds of Formula (II):

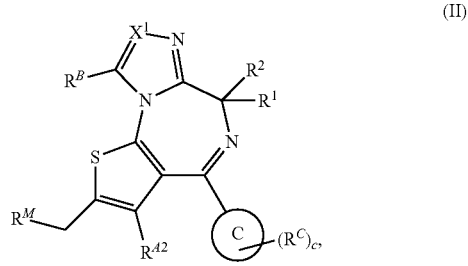

(II)

or a pharmaceutically acceptable salt, stereoisomer, tautomer, solvate, hydrate, polymorph, co-crystal, or prodrug thereof, wherein:

$R^M$ is —CN, —$N(R^f)_2$, or —$CH_2N(R^f)_2$;

$R^{42}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;

$X^1$ is N or $CR^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;

$R^B$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN;

Ring C is aryl or heteroaryl;

each occurrence of R$^C$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —OR$^f$, —SR$^f$, —N(R$^f$)$_2$, —NO$_2$, or —CN;

c is 0, 1, 2, 3, or 4;

R$^1$ is hydrogen, halogen, optionally substituted alkyl, or —(CH$_2$)$_n$L, wherein n is 0, 1, 2, 3, or 4, and L is —C(=O)R$^3$, —C(=O)OR$^3$, —C(=O)NR$^3$R$^4$, —S(=O)$_2$R$^3$, —S(=O)$_2$OR$^3$, —S(=O)$_2$NR$^3$R$^4$, —OR$^3$, —NR$^3$R$^4$, —N(R$^4$)C(=O)R$^3$, optionally substituted carbocyclyl, optionally substituted heterocyclyl, optionally substituted aryl, or optionally substituted heteroaryl;

R$^2$ is hydrogen, halogen, or optionally substituted alkyl;

each R$^3$ and R$^4$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or optionally substituted acyl, an oxygen protecting group, or a nitrogen protecting group, or R$^3$ and R$^4$ are joined to form an optionally substituted heterocyclic or optionally substituted heteroaryl ring; and each occurrence of R$^f$ is independently, hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, or a nitrogen protecting group, or two R$^f$ are joined to form an optionally substituted heterocyclic or optionally substituted heteroaryl ring.

In certain embodiments, the compound of Formula (I) is not of formula:

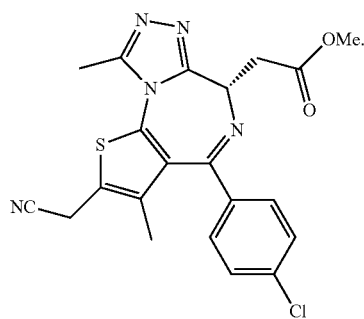 [SMILES: COC(=O)C[C@@H]1N=C(c2ccc(Cl)cc2)c2c(sc(CC#N)c2C)-n2c(C)nnc21]

In certain embodiments, the compound of Formula (I) is not of formula:

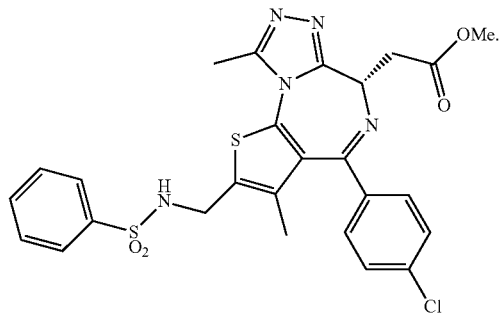 [SMILES: COC(=O)C[C@@H]1N=C(c2ccc(Cl)cc2)c2c(sc(CNS(=O)(=O)c3ccccc3)c2C)-n2c(C)nnc21]

In certain embodiments, R$^1$ is not —CH$_2$C(=O)OR$^3$. In certain embodiments, R$^1$ is hydrogen, halogen, or —(CH$_2$)$_n$L, wherein n is 0, 1, 2, 3 or 4, and L is —C(=O)R$^3$, —C(=O)NR$^3$R$^4$, —S(=O)$_2$R$^3$, —S(=O)$_2$OR$^3$, —S(=O)$_2$NR$^3$R$^4$, —OR$^3$, —NR$^3$R$^4$, —N(R$^4$)C(=O)R$^3$, optionally substituted carbocyclyl, optionally substituted heterocyclyl, optionally substituted aryl, or optionally substituted heteroaryl, and R$^2$ is hydrogen or halogen.

In certain embodiments, compounds of Formula (II) do not include compounds disclosed in any of U.S. Pat. Nos. 5,712,274, 8,044,042, 8,476,260, 8,981,083, WIPO Application No. PCT/US2014/023386, filed Mar. 11, 2014, WIPO Application No. PCT/US2011/036647, filed May 16, 2011, WIPO Application No. PCT/US2011/036667, filed May 16, 2011, WIPO Application No. PCT/US2011/036672, filed May 16, 2011, WIPO Application No. PCT/US2011/036701, filed May 16, 2011, WIPO Application No. PCT/JP2008/073864, filed Dec. 26, 2008, WIPO Application No. PCT/JP1992/001198, Sep. 18, 1992, WIPO Application No. PCT/JP1993/001329, filed Sep. 16, 1993, and WIPO Application No. PCT/JP2006/310709, filed May 30, 2006.

R$^1$ and R$^2$

Compounds of Formulae (I) and (II) comprise R$^1$ and R$^2$. In some embodiments, the carbon to which R$^1$ and R$^2$ is attached is in the (R)-configuration. In some embodiments, the carbon to which R$^1$ and R$^2$ is attached is in the (S)-configuration. In some embodiments, R$^2$ is hydrogen, and the carbon to which R$^1$ is attached is in the (R)-configuration. In some embodiments, R$^2$ is hydrogen, and the carbon to which R$^1$ is attached is in the (S)-configuration. In some embodiments, R$^1$ and R$^2$ are the same. In some embodiments, R$^1$ and R$^2$ are different.

As generally defined herein, R$^1$ is hydrogen, halogen, optionally substituted alkyl, or —(CH$_2$)$_n$L, wherein n is 0, 1, 2, 3 or 4, and L is —C(=O)R$^3$, —C(=O)OR$^3$, —C(=O)NR$^3$R$^4$, —S(=O)$_2$R$^3$, —S(=O)$_2$OR$^3$, —S(=O)$_2$NR$^3$R$^4$, —OR$^3$, —NR$^3$R$^4$, —N(R$^4$)C(=O)R$^3$, optionally substituted carbocyclyl, optionally substituted heterocyclyl, optionally substituted aryl, or optionally substituted heteroaryl.

In certain embodiments, R$^1$ is hydrogen. In certain embodiments, R$^1$ is a non-hydrogen group. In certain embodiments, R$^1$ is halogen. In certain embodiments, R$^1$ is —F. In certain embodiments, R$^1$ is —Cl, —Br, or —I.

In certain embodiments, R$^1$ is optionally substituted alkyl, e.g., optionally substituted C$_{1-6}$ alkyl, optionally substituted C$_1^1$ alkyl, optionally substituted C$_{1-3}^1$ alkyl, optionally substituted C$_{3-4}$ alkyl, optionally substituted C$_{4-5}$ alkyl, or optionally substituted C$_{5-6}$ alkyl. In certain embodiments, R$^1$ is unsubstituted alkyl e.g., unsubstituted $C_{1-6}$ alkyl, unsubstituted $C_{1-2}^1$ alkyl, unsubstituted $C_{-3}^1$ alkyl, unsubstituted $C_{3-4}$ alkyl, unsubstituted $C_{4-5}$ alkyl, or unsubstituted $C_{5-6}$ alkyl. In certain embodiments, $R^1$ is methyl. In certain embodiments, $R^1$ is ethyl, propyl, or butyl. In certain embodiments, $R^1$ is haloalkyl, e.g., —$CHF^1$, —$CHCl^1$, —$CH^1CHF^1$, —$CH^1CHCl^1$. In certain embodiments, $R^1$ is perhaloalkyl, e.g., —$CF_3$, —$CF^1CF_3$, —$CCl_3$. In certain embodiments, $R^1$ is hydroxyalkyl, e.g., —$CH^1OH$, —$CH^1CH^1OH$, —$CH^1OR^f$, —$CH^1CH^1OR^f$. In certain embodiments, $R^1$ is aminoalkyl, e.g., —$CH^1NH^1$, —$CH^1CH^1NH^1$, —$CH^1NMe^1$, —$CH^1CH^1NMe^1$, —$CH^1N(R^f)^1$, —$CH^1CH^1N(R^f)^1$.

In certain embodiments, $R^1$ is —$(CH_2)_nL$, wherein n is 0, 1, 2, 3 or 4, and L is —$C(=O)R^3$, —$C(=O)OR^3$, —$C(=O)NR^3R^4$, —$S(=O)_2R^3$, —$S(=O)_2OR^3$, —$S(=O)_2NR^3R^4$, —$OR^3$, —$NR^3R^4$, —$N(R^4)C(=O)R^3$, optionally substituted carbocyclyl, optionally substituted heterocyclyl, optionally substituted aryl, or optionally substituted heteroaryl. In certain embodiments, n is 0. In certain embodiments, n is 1. In certain embodiments, n is 2. In certain embodiments, n is 3. In certain embodiments, n is 4. In certain embodiments, n is 0, 1, 2, or 3. In certain embodiments, n is 0, 1, or 2. In certain embodiments, n is 0 or 1. In certain embodiments, n is 1, 2, 3, or 4. In certain embodiments, n is 2, 3, or 4. In certain embodiments, n is 3 or 4. When n is 0, $R^1$ is -L, such that $R^1$ is —$C(=O)R^3$, —$C(=O)OR^3$, —$C(=O)NR^3R^4$, —$S(=O)_2R^3$, —$S(=O)_2OR^3$, —$S(=O)_2NR^3R^4$, —$OR^3$, —$NR^3R^4$, —$N(R^4)C(=O)R^3$, optionally substituted carbocyclyl, optionally substituted heterocyclyl, optionally substituted aryl, or optionally substituted heteroaryl.

In certain embodiments, L is —$C(=O)R^3$. In certain embodiments, L is —$C(=O)OR^3$. In certain embodiments, L is —$C(=O)NR^3R^4$. In certain embodiments, L is —$C(=O)NHR^3$. In certain embodiments, L is —$S(=O)_2R^3$. In certain embodiments, L is —$S(=O)_2OR^3$. In certain embodiments, L is —$S(=O)_2NR^3R^4$. In certain embodiments, L is —$S(=O)_2OR^3$. In certain embodiments, L is —$S(=O)_2NHR^3$. In certain embodiments, L is —$OR^3$. In certain embodiments, L is —$NR^3R^4$. In certain embodiments, L is —$NHR^3$. In certain embodiments, L is —$N(R^4)C(=O)R^3$. In certain embodiments, L is —$NHC(=O)R^3$.

As generally defined herein, each of $R^3$ and $R^4$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or optionally substituted acyl, an oxygen protecting group, or a nitrogen protecting group, or $R^3$ and $R^4$ are joined to form an optionally substituted heterocyclic or optionally substituted heteroaryl ring.

In certain embodiments, $R^3$ is hydrogen. In certain embodiments, $R^3$ is a non-hydrogen group. In certain embodiments, $R^3$ is halogen. In certain embodiments, $R^3$ is —F. In certain embodiments, $R^3$ is —Cl, —Br, or —I. In certain embodiments, $R^3$ is —$NO_2$. In certain embodiments, $R^3$ is —CN.

In certain embodiments, $R^3$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^3$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^3$ is methyl. In certain embodiments, $R^3$ is ethyl, propyl, or butyl. In certain embodiments, $R^3$ is haloalkyl, e.g., —$CHF_2$, —$CHCl_2$, —$CH_2CHF_2$, —$CH_2CHCl_2$. In certain embodiments, $R^3$ is perhaloalkyl, e.g., —$CF_3$, —$CF_2CF_3$, —$CCl_3$. In certain embodiments, $R^3$ is hydroxyalkyl, e.g., —$CH_2CH_2OH$, —$CH_2OR^f$, —$CH_2CH_2OR^f$. In certain embodiments, $R^3$ is aminoalkyl, e.g., —$CH_2NH_2$, —$CH_2CH_2NH_2$, —$CH_2NMe_2$, —$CH_2CH_2NMe_2$, —$CH_2N(R^f)_2$, —$CH_2CH_2N(R^f)_2$.

In certain embodiments, $R^3$ is optionally substituted alkenyl, e.g., optionally substituted $C_{2-6}$ alkenyl. In certain embodiments, $R^3$ is unsubstituted alkenyl, e.g., unsubstituted $C_{2-6}$ alkenyl. In certain embodiments, $R^3$ is vinyl, allyl, or prenyl. In certain embodiments, $R^3$ is optionally substituted alkynyl, e.g., optionally substituted $C_{2-6}$ alkynyl. In certain embodiments, $R^3$ is unsubstituted alkynyl, e.g., unsubstituted $C_2L_6$ alkynyl.

In certain embodiments, $R^3$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^3$ is unsubstituted carbocyclyl, e.g., unsubstituted $C_{3-6}$ carbocyclyl. In some embodiments, $R^3$ is cyclopropyl, cyclobutyl, cyclopentyl, or cyclohexyl. In certain embodiments, $R^3$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^3$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^3$ is optionally substituted aryl, e.g., optionally substituted phenyl. In certain embodiments, $R^3$ is unsubstituted aryl, e.g., unsubstituted phenyl. In certain embodiments, $R^3$ is optionally substituted heteroaryl, e.g., optionally substituted 5-6 membered heteroaryl, or optionally substituted 9-10 membered bicyclic heteroaryl. In certain embodiments, $R^3$ is unsubstituted heteroaryl, e.g., unsubstituted 5-6 membered heteroaryl, or unsubstituted 9-10 membered bicyclic heteroaryl. In certain embodiments, $R^3$ is optionally substituted aralkyl, e.g., optionally substituted benzyl. In certain embodiments, $R^3$ is optionally substituted heteroaralkyl, e.g., methyl substituted with an optionally substituted 5-6 membered heteroaryl ring. In certain embodiments, $R^3$ is unsubstituted aralkyl, e.g., unsubstituted benzyl. In certain embodiments, $R^3$ is unsubstituted heteroaralkyl, e.g., methyl substituted with an unsubstituted 5-6 membered heteroaryl ring.

In certain embodiments, $R^3$ is optionally substituted acyl, e.g., —CHO, —$CO_2H$, or —$C(=O)NH_2$. In certain embodiments, $R^3$ is —$C(=O)R^f$, —$C(=O)OR^f$, —$C(=O)NH(R^f)$, or —$C(=O)N(R^f)_2$. In certain embodiments, $R^3$ is —$C(=O)R^f$, and $R^f$ is optionally substituted alkyl, e.g., —$C(=O)Me$. In certain embodiments, $R^3$ is —$C(=O)R^f$, and $R^f$ is optionally substituted alkenyl. In certain embodiments, $R^3$ is —$C(=O)R^f$, and $R^f$ is optionally substituted carbocyclyl, heterocyclyl, aryl, or heteroaryl. In certain embodiments, $R^3$ is —$C(=O)OR^f$, and $R^f$ is optionally substituted alkyl. In certain embodiments, $R^3$ is —$C(=O)OR^f$, and $R^f$ is optionally substituted alkenyl. In certain embodiments, $R^3$ is —$C(=O)OR^f$, and $R^f$ is optionally substituted carbocyclyl, heterocyclyl, aryl, or heteroaryl. In certain embodiments, $R^3$ is —$C(=O)N(R^f)_2$, and at least one $R^f$ is optionally substituted alkyl. In certain embodiments, $R^3$ is —C(=O)NHR$^f$, and R$^f$ is optionally substituted alkyl. In certain embodiments, $R^3$ is —C(=O)NHR$^f$, and R$^f$ is optionally substituted alkenyl. In certain embodiments, $R^3$ is —C(=O)NHR$^f$, and R$^f$ is optionally substituted carbocyclyl, heterocyclyl, aryl, or heteroaryl. In certain embodiments, $R^3$ is a nitrogen protecting group. In some embodiments, $R^3$ is Bn, Boc, Cbz, Fmoc, trifluoroacetyl, triphenylmethyl, acetyl, or Ts.

In certain embodiments, $R^4$ is hydrogen. In certain embodiments, $R^4$ is a non-hydrogen group. In certain embodiments, $R^4$ is halogen. In certain embodiments, $R^4$ is —F. In certain embodiments, $R^4$ is —Cl, —Br, or —I. In certain embodiments, $R^4$ is —NO$_2$. In certain embodiments, $R^4$ is —CN.

In certain embodiments, $R^4$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^4$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^4$ is methyl. In certain embodiments, $R^4$ is ethyl, propyl, or butyl. In certain embodiments, $R^4$ is haloalkyl, e.g., —CHF$_2$, —CHCl$_2$, —CH$_2$CHF$_2$, —CH$_2$CHCl$_2$. In certain embodiments, $R^4$ is perhaloalkyl, e.g., —CF$_3$, —CF$_2$CF$_3$, —CCl$_3$. In certain embodiments, $R^4$ is hydroxyalkyl, e.g., —CH$_2$OH, —CH$_2$CH$_2$OH, —CH$_2$OR$^f$, —CH$_2$CH$_2$OR$^f$. In certain embodiments, $R^4$ is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N(R$^f$)$_2$, —CH2CH2N(R$^f$)$_2$.

In certain embodiments, $R^4$ is optionally substituted alkenyl, e.g., optionally substituted $C_{2-6}$ alkenyl. In certain embodiments, $R^4$ is unsubstituted alkenyl, e.g., unsubstituted $C_{2-6}$ alkenyl. In certain embodiments, $R^4$ is vinyl, allyl, or prenyl. In certain embodiments, $R^4$ is optionally substituted alkynyl, e.g., optionally substituted $C_{2-6}$ alkynyl. In certain embodiments, $R^4$ is unsubstituted alkynyl, e.g., unsubstituted $C_{2-6}$ alkynyl.

In certain embodiments, $R^4$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^4$ is unsubstituted carbocyclyl, e.g., unsubstituted $C_{3-6}$ carbocyclyl. In some embodiments, $R^4$ is cyclopropyl, cyclobutyl, cyclopentyl, or cyclohexyl. In certain embodiments, $R^4$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^4$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^4$ is optionally substituted aryl, e.g., optionally substituted phenyl. In certain embodiments, $R^4$ is unsubstituted aryl, e.g., unsubstituted phenyl. In certain embodiments, $R^4$ is optionally substituted heteroaryl, e.g., optionally substituted 5-6 membered heteroaryl, or optionally substituted 9-10 membered bicyclic heteroaryl. In certain embodiments, $R^4$ is unsubstituted heteroaryl, e.g., unsubstituted 5-6 membered heteroaryl, or unsubstituted 9-10 membered bicyclic heteroaryl. In certain embodiments, $R^4$ is optionally substituted aralkyl, e.g., optionally substituted benzyl. In certain embodiments, $R^4$ is optionally substituted heteroaralkyl, e.g., methyl substituted with an optionally substituted 5-6 membered heteroaryl ring. In certain embodiments, $R^4$ is unsubstituted aralkyl, e.g., unsubstituted benzyl. In certain embodiments, $R^4$ is unsubstituted heteroaralkyl, e.g., methyl substituted with an unsubstituted 5-6 membered heteroaryl ring.

In certain embodiments, $R^4$ is optionally substituted acyl, e.g., —CHO, —CO$_2$H, or —C(=O)NH$_2$. In certain embodiments, $R^4$ is —C(=O)R$^f$, —C(=O)OR$^f$, —C(=O)NH(R$^f$), or —C(=O)N(R$^f$)$_2$. In certain embodiments, $R^4$ is —C(=O)R$^f$, and R$^f$ is optionally substituted alkyl, e.g., —C(=O)Me. In certain embodiments, $R^4$ is —C(=O)R$^f$, and R$^f$ is optionally substituted alkenyl. In certain embodiments, $R^4$ is —C(=O)R$^f$, and R$^f$ is optionally substituted carbocyclyl, heterocyclyl, aryl, or heteroaryl. In certain embodiments, $R^4$ is —C(=O)OR$^f$, and R$^f$ is optionally substituted alkyl. In certain embodiments, $R^4$ is —C(=O)OR$^f$, and R$^f$ is optionally substituted alkenyl. In certain embodiments, $R^4$ is —C(=O)OR$^f$, and R$^f$ is optionally substituted carbocyclyl, heterocyclyl, aryl, or heteroaryl. In certain embodiments, $R^4$ is —C(=O)N(R$^f$)$_2$, and at least one R$^f$ is optionally substituted alkyl. In certain embodiments, $R^4$ is —C(=O)NHR$^f$, and R$^f$ is optionally substituted alkyl. In certain embodiments, $R^4$ is —C(=O)NHR$^f$, and R$^f$ is optionally substituted alkenyl. In certain embodiments, $R^4$ is —C(=O)NHR$^f$, and R$^f$ is optionally substituted carbocyclyl, heterocyclyl, aryl, or heteroaryl. In certain embodiments, $R^4$ is a nitrogen protecting group. In some embodiments, $R^4$ is Bn, Boc, Cbz, Fmoc, trifluoroacetyl, triphenylmethyl, acetyl, or Ts.

In certain embodiments, $R^3$ and $R^4$ are the same. In certain embodiments, $R^3$ and $R^4$ are different. In certain embodiments, $R^3$ and $R^4$ are both hydrogen. In certain embodiments, $R^3$ and $R^4$ are both optionally substituted alkyl. In certain embodiments, $R^3$ and $R^4$ are both optionally substituted $C_{1-6}$ alkyl. In certain embodiments, $R^3$ and $R^4$ are both unsubstituted $C_{1-6}$ alkyl. In certain embodiments, $R^3$ and $R^4$ are both methyl. In certain embodiments, $R^3$ and $R^4$ are both ethyl, propyl, or butyl.

In certain embodiments, $R^3$ and $R^4$ are joined to form an optionally substituted heterocyclic ring. In certain embodiments, $R^3$ and $R^4$ are joined to form an unsubstituted heterocyclic ring. In some embodiments, $R^3$ and $R^4$ are joined to form a substituted or unsubstituted piperidinyl, dihydropyridinyl, piperazinyl, or morpholinyl ring. In certain embodiments, $R^3$ and $R^4$ are joined to form a substituted or unsubstituted piperidinyl ring. In certain embodiments, $R^3$ and $R^4$ are joined to form a substituted or unsubstituted dihydropyridinyl ring. In certain embodiments, $R^3$ and $R^4$ are joined to form a substituted or unsubstituted piperazinyl ring. In certain embodiments, $R^3$ and $R^4$ are joined to form a substituted or unsubstituted morpholinyl ring. In certain embodiments, $R^3$ and $R^4$ are joined to form an optionally substituted heteroaryl ring. In certain embodiments, $R^3$ and $R^4$ are joined to form an unsubstituted heteroaryl ring. In some embodiments, $R^3$ and $R^4$ are joined to form a substituted or unsubstituted pyrrolyl, imidazolyl, pyrazolyl, triazolyl, or tetrazolyl ring. In certain embodiments, $R^3$ and $R^4$ are joined to form a substituted or unsubstituted pyrrolyl ring. In certain embodiments, $R^3$ and $R^4$ are joined to form a substituted or unsubstituted imidazolyl ring. In certain embodiments, $R^3$ and $R^4$ are joined to form a substituted or unsubstituted pyrazolyl ring. In certain embodiments, $R^3$ and $R^4$ are joined to form a substituted or unsubstituted triazolyl ring. In certain embodiments, $R^3$ and $R^4$ are joined to form a substituted or unsubstituted tetrazolyl ring.

In certain embodiments, $R^L$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^L$ is unsubstituted carbocyclyl, e.g., unsubstituted $C_{3-6}$ carbocyclyl. In some embodiments, $R^L$ is cyclopropyl, cyclobutyl, cyclopentyl, or cyclohexyl. In certain embodiments, $R^L$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^L$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^L$ is optionally substituted aryl, e.g., optionally substituted phenyl. In certain embodiments, $R^L$ is unsubstituted aryl, e.g., unsubstituted phenyl. In certain embodiments, $R^L$ is optionally substituted heteroaryl, e.g., optionally substituted 5-6 membered heteroaryl, or optionally substituted 9-10 membered bicyclic heteroaryl. In certain embodiments, $R^L$ is unsubstituted heteroaryl, e.g., unsubstituted 5-6 membered heteroaryl, or unsubstituted 9-10 membered bicyclic heteroaryl. In certain embodiments, $R^L$ is optionally substituted aralkyl, e.g., optionally substituted benzyl. In certain embodiments, $R^L$ is optionally substituted heteroaralkyl, e.g., methyl substituted with an optionally substituted 5-6 membered heteroaryl ring. In certain embodiments, $R^L$ is unsubstituted aralkyl, e.g., unsubstituted benzyl. In certain embodiments, $R^L$ is unsubstituted heteroaralkyl, e.g., methyl substituted with an unsubstituted 5-6 membered heteroaryl ring.

In certain embodiments, L is —$OR^3$, e.g., —OH. In certain embodiments, L is —$OR^3$, and $R^3$ is optionally substituted alkyl. In certain embodiments, L is —$OR^3$, and $R^3$ is unsubstituted $C_{1-6}$ alkyl. In certain embodiments, L is —$OR^3$, and $R^3$ is optionally substituted alkenyl. In certain embodiments, L is —$OR^3$, and $R^3$ is optionally substituted carbocyclyl, optionally substituted heterocyclyl, optionally substituted aryl optionally substituted heteroaryl. In certain embodiments, L is —$OR^3$, and $R^3$ is unsubstituted carbocyclyl, unsubstituted heterocyclyl, unsubstituted aryl unsubstituted heteroaryl. In certain embodiments, L is —$OR^3$, and $R^3$ is optionally substituted acyl, e.g., L is —OC(=O)$R^f$, —OC(=O)$OR^f$, or —OC(=O)N($R^f$)$_2$. In certain embodiments, L is —$OR^3$, and $R^3$ is an oxygen protecting group.

In certain embodiments, L is —$NR^3R^4$, e.g., —$NH_2$, —$NHR^3$. In certain embodiments, L is —$NHR^3$, and $R^3$ is optionally substituted alkyl. In certain embodiments, L is —$NR^3R^4$, and at least one of $R^3$ and $R^4$ is optionally substituted alkyl. In certain embodiments, L is —$NHR^3$, and $R^3$ is unsubstituted alkyl. In certain embodiments, L is —$NR^3R^4$, and at least one of $R^3$ and $R^4$ is unsubstituted alkyl. In certain embodiments, $R^1$ is —($CH_2$)NH (optionally substituted $C_{1-6}$ alkyl). In certain embodiments, L is —$NHR^3$, and $R^3$ is optionally substituted carbocyclyl, optionally substituted heterocyclyl, optionally substituted aryl, or optionally substituted heteroaryl. In certain embodiments, L is —$NHR^3$, and $R^3$ is optionally substituted phenyl. In certain embodiments, $R^1$ is of the formula:

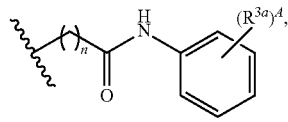

wherein $R^{3a}$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^g)_2$, or —$NO_2$; $R^g$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group; n is 0, 1, 2, 3 or 4; and A is 0, 1, 2, 3, 4, or 5. In certain embodiments, $R^{3a}$ is halogen (e.g., F, Cl, Br, or I). In certain embodiments, at least one $R^{A1}$ is substituted or unsubstituted alkyl (e.g., substituted or unsubstituted $C_{1-6}$ alkyl). In certain embodiments, $R^{3a}$ is substituted or unsubstituted methyl. In certain embodiments, $R^{3a}$ is substituted or unsubstituted ethyl. In certain embodiments, $R^{3a}$ is substituted or unsubstituted propyl. In certain embodiments, $R^{3a}$ is substituted or unsubstituted alkenyl (e.g., substituted or unsubstituted $C_{2-6}$ alkenyl). In certain embodiments, $R^{3a}$ is substituted or unsubstituted alkynyl (e.g., substituted or unsubstituted $C_{2-6}$ alkynyl). In certain embodiments, $R^{3a}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{3a}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, Ria is substituted or unsubstituted aryl (e.g., substituted or unsubstituted, 6- to 10-membered aryl). In certain embodiments, $R^{3a}$ is benzyl. In certain embodiments, $R^{3a}$ is substituted or unsubstituted phenyl. In certain embodiments, $R^{3a}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{3a}$ is —$OR^f$ (e.g., —OH or —OMe). In certain embodiments, $R^{3a}$ is optionally substituted acyl (e.g., —C(=O)$R^f$) (e.g., —C(=O)Me). In certain embodiments, $R^{3a}$ is —$SR^f$, —$N(R^g)_2$, or —$NO_2$, In certain embodiments, $R^g$ is optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group. In certain embodiments, n is 0. In certain embodiments, n is 1. In certain embodiments, n is 2. In certain embodiments, n is 3. In certain embodiments, n is 4. In certain embodiments, A is 0. In certain embodiments, A is 1. In certain embodiments, A is 2. In certain embodiments, A is 3. In certain embodiments, A is 4. In certain embodiments, A is 5. In certain embodiments, $R^f$ is hydrogen. In certain embodiments, $R^f$ is optionally substituted alkyl (e.g., substituted or unsubstituted $C_{1-6}$ alkyl). In certain embodiments, $R^f$ is substituted or unsubstituted methyl. In certain embodiments, $R^f$ is substituted or unsubstituted ethyl. In certain embodiments, R $R^{f3a}$ is substituted or unsubstituted propyl. In certain embodiments, $R^f$ is substituted or unsubstituted alkenyl (e.g., substituted or unsubstituted $C_{2-6}$ alkenyl). In certain embodiments, $R^f$ is substituted or unsubstituted alkynyl (e.g., substituted or unsubstituted $C_{2-6}$ alkynyl). In certain embodiments, $R^f$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^f$ is substituted or unsubstituted heterocyclyl (e.g., substituted or unsubstituted, 5- to 10-membered monocycle or bicyclic heterocyclic ring, wherein one or two atoms in the heterocyclic ring are independently nitrogen, oxygen, or sulfur). In certain embodiments, $R^f$ is substituted or unsubstituted aryl (e.g., substituted or unsubstituted, 6- to 10-membered aryl). In certain embodiments, $R^f$ is substituted or unsubstituted heteroaryl (e.g., substituted or unsubstituted, 5- to 6-membered, monocycle heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, two $R^f$ are joined to form an optionally substituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur), or optionally substituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^f$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^f$ is optionally substituted acyl or optionally substituted sulfonyl. In certain embodiments. L is —NHR³, and R³ is unsubstituted carbocyclyl, unsubstituted heterocyclyl, unsubstituted aryl, or unsubstituted heteroaryl. In certain embodiments, L is —NHR³, and R³ is optionally substituted acyl, e.g., L is —NHC(=O)R$^f$, —NHC(=O)OR$^f$, or —NHC(=O)NHR$^f$. In certain embodiments, L is —NR³R⁴, and at least one of R³ and R⁴ is a nitrogen protecting group. In certain embodiments, L is —NR³R⁴, and R³ and R⁴ are joined to form an optionally substituted heterocyclic or optionally substituted heteroaryl ring. In certain embodiments, L is —NR³R⁴, and R³ and R⁴ are joined to form an unsubstituted heterocyclic or unsubstituted heteroaryl ring.

In certain embodiments, R¹ is of formula:

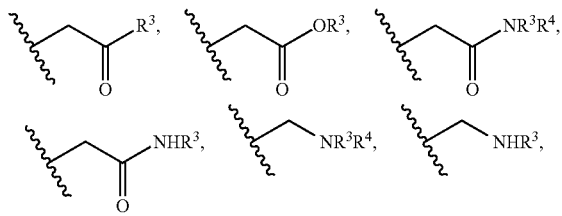

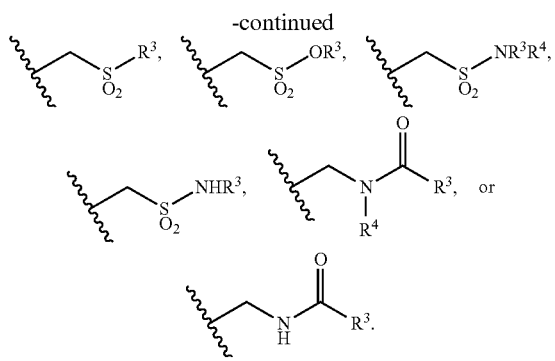

In certain embodiments. R¹ is of formula:

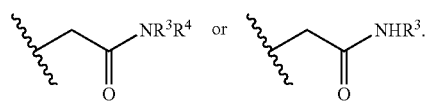

In certain embodiments, R¹ is of formula:

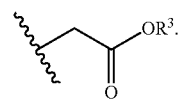

In certain embodiments, R¹ is of formula:

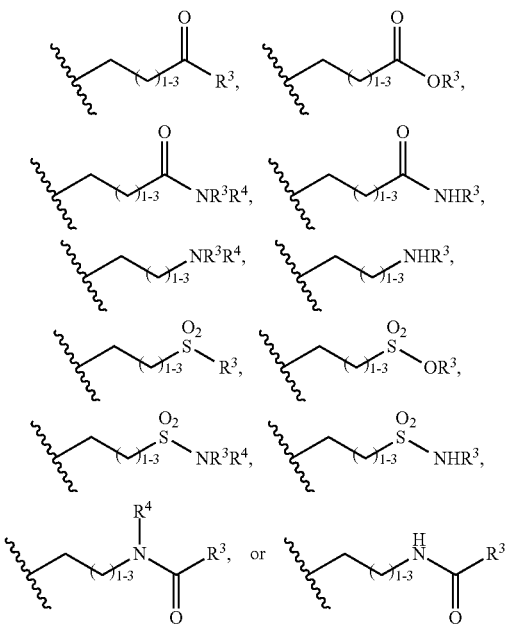

In certain embodiments, R¹ is of formula:

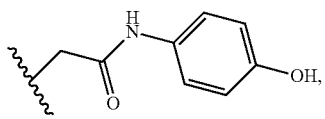

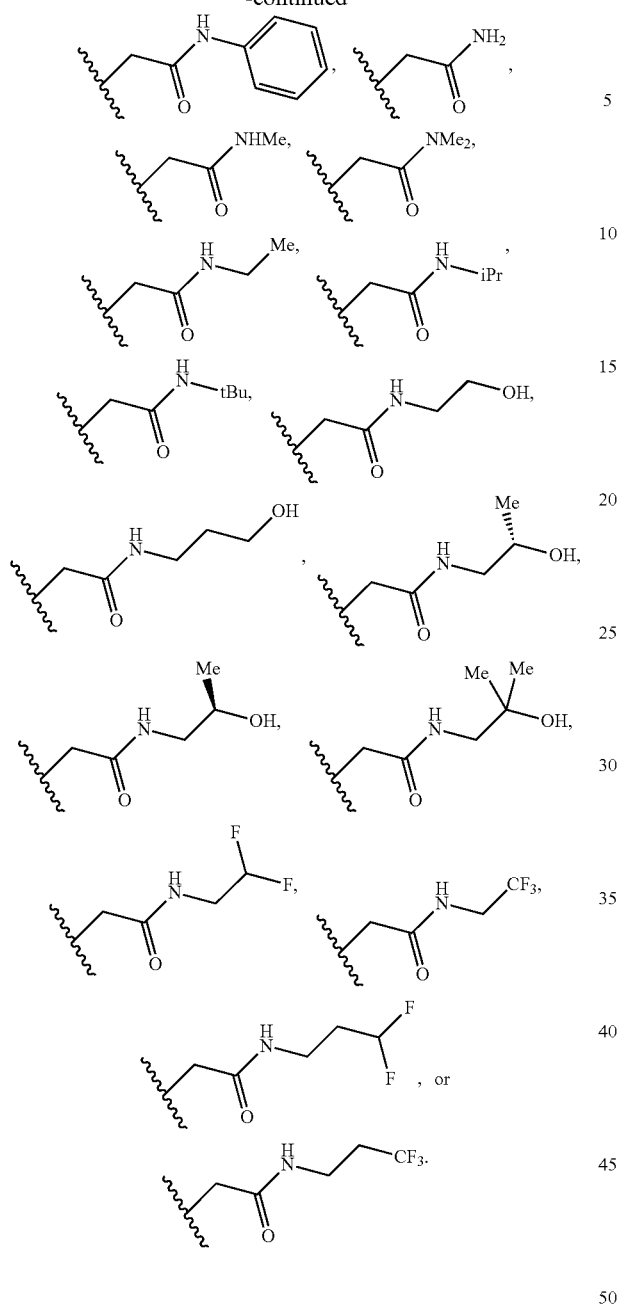
In certain embodiments, $R^1$ is of formula:
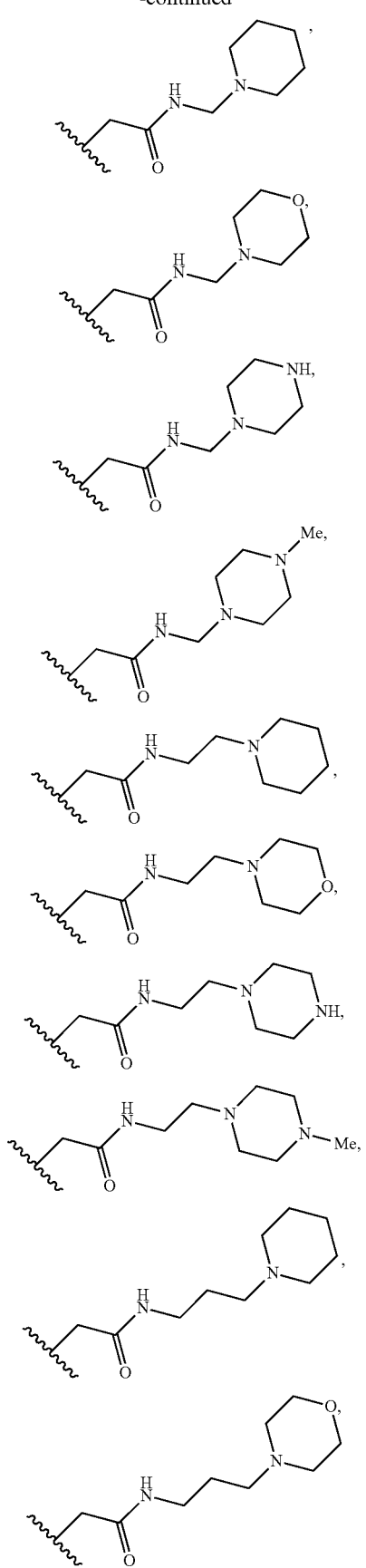

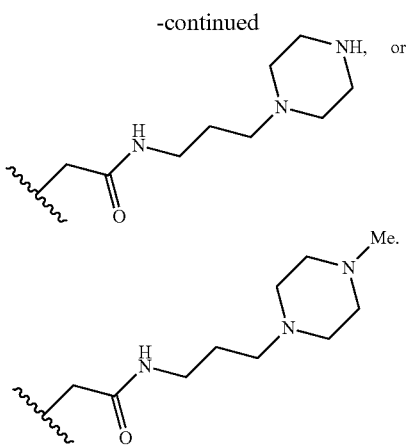

As generally defined herein, R² is hydrogen, halogen, or optionally substituted alkyl. In certain embodiments, R² is hydrogen. In certain embodiments, R² is a non-hydrogen group. In certain embodiments, R² is halogen. In certain embodiments, R² is —F. In certain embodiments, R² is —Cl, —Br, or —I.

In certain embodiments, R² is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, R² is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, R² is methyl. In certain embodiments, R² is ethyl, propyl, or butyl. In certain embodiments, R² is haloalkyl, e.g., —CHF₂, —CHCl₂, —CH₂CHF₂, —CH₂CHCl₂. In certain embodiments, R² is perhaloalkyl, e.g., —CF₃, —CF₂CF₃, —CCl₃. In certain embodiments, R² is hydroxyalkyl, e.g., —CH₂OH, —CH₂CH₂OH, —CH₂OR$^f$, —₂CH₂OR$^f$. In certain embodiments, R² is aminoalkyl, e.g., —CH₂NH₂, —CH₂CH₂NH₂, —CH₂NMe₂, —CH₂CH₂NMe₂, —CH₂N(R$^f$)₂, —CH2CH2N(R$^f$)₂.

$R^{41}$ and $R^{42}$

Compounds of Formula (I) comprise groups $R^{41}$ and $R^{42}$. Compounds of Formula (II) comprise group $R^{42}$ and —CH₂R$^M$ at the position to which $R^{41}$ is attached in compounds of Formula (I).

As generally defined herein, $R^{41}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)₂, —NO₂, or —CN. In certain embodiments, $R^{41}$ is —CH₂R$^M$, wherein R$^M$ is —CN, —N(R$^f$)₂, or —CH₂N(R$^f$)₂. In certain embodiments, $R^{42}$ is —CH₂R$^M$, wherein R$^M$ is —CN, —N(R$^f$)₂, or —CH₂N(R$^f$)₂.

In certain embodiments, $R^{41}$ is hydrogen. In certain embodiments, $R^{41}$ is a non-hydrogen group. In certain embodiments, $R^{41}$ is halogen. In certain embodiments, $R^{41}$ is —F. In certain embodiments, $R^{41}$ is —Cl, —Br, or —I. In certain embodiments, $R^{41}$ is —NO₂. In certain embodiments, $R^{41}$ is —CN.

In certain embodiments, $R^{41}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{41}$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^{41}$ is methyl. In certain embodiments, $R^{41}$ is ethyl, propyl, or butyl. In certain embodiments, $R^{41}$ is haloalkyl, e.g., —CHF₂, —CHCl₂, —CH₂CHF₂, —CH₂CHCl₂. In certain embodiments, $R^{41}$ is perhaloalkyl, e.g., —CF₃, —CF₂CF₃, —CCl₃. In certain embodiments, $R^{41}$ is hydroxyalkyl, e.g., —CH₂OH, —CH₂CH₂OH, —CH₂OR$^f$, —CH₂CH₂OR$^f$. In certain embodiments, $R^{41}$ is aminoalkyl, e.g., —CH₂NH₂, —CH₂CH₂NH₂, —CH₂NMe₂, —CH₂CH₂NMe₂, —CH₂N(R$^f$)₂, —CH2CH2N(R$^f$)₂.

In certain embodiments, $R^{41}$ is optionally substituted alkenyl, e.g., optionally substituted $C_{2-6}$ alkenyl. In certain embodiments, $R^{41}$ is unsubstituted alkenyl, e.g., unsubstituted $C_{2-6}$ alkenyl. In certain embodiments, $R^{41}$ is vinyl, allyl, or prenyl. In certain embodiments, $R^{41}$ is optionally substituted alkynyl, e.g., optionally substituted $C_{2-6}$ alkynyl. In certain embodiments, $R^{41}$ is unsubstituted alkynyl, e.g., unsubstituted $C_{2-6}$ alkynyl.

In certain embodiments, $R^{41}$ is optionally substituted carbocyclyl, e.g., optionally substituted $C_{3-6}$ carbocyclyl, optionally substituted $C_{3-4}$ carbocyclyl, optionally substituted $C_{4-5}$ or optionally substituted $C_{5-6}$ carbocyclyl. In certain embodiments, $R^{41}$ is unsubstituted carbocyclyl, e.g., unsubstituted $C_{3-6}$ carbocyclyl. In some embodiments, $R^{41}$ is cyclopropyl, cyclobutyl, cyclopentyl, or cyclohexyl. In certain embodiments, $R^{41}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^{41}$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^{41}$ is optionally substituted aryl, e.g., optionally substituted phenyl. In certain embodiments, $R^{41}$ is unsubstituted aryl, e.g., unsubstituted phenyl. In certain embodiments, $R^{41}$ is optionally substituted heteroaryl, e.g., optionally substituted 5-6 membered heteroaryl, or optionally substituted 9-10 membered bicyclic heteroaryl. In certain embodiments, $R^{41}$ is unsubstituted heteroaryl, e.g., unsubstituted 5-6 membered heteroaryl, or unsubstituted 9-10 membered bicyclic heteroaryl. In certain embodiments, $R^{41}$ is optionally substituted aralkyl, e.g., optionally substituted benzyl. In certain embodiments, $R^{41}$ is optionally substituted heteroaralkyl, e.g., methyl substituted with an optionally substituted 5-6 membered heteroaryl ring. In certain embodiments, $R^{41}$ is unsubstituted aralkyl, e.g., unsubstituted benzyl. In certain embodiments, $R^{41}$ is unsubstituted heteroaralkyl, e.g., methyl substituted with an unsubstituted 5-6 membered heteroaryl ring.

In certain embodiments, $R^{41}$ is optionally substituted acyl, e.g., —CHO, —CO₂H, or —C(=O)NH₂. In certain embodiments, $R^{41}$ is —C(=O)R$^f$, —C(=O)OR$^f$, —C(=O)NH(R$^f$), or —C(=O)N(R$^f$)₂. In certain embodiments, $R^{41}$ is —C(=O)R$^f$, and R$^f$ is optionally substituted alkyl, e.g., —C(=O)Me. In certain embodiments, $R^{41}$ is —C(=O)R$^f$, and R$^f$ is optionally substituted alkenyl. In certain embodiments, $R^{41}$ is —C(=O)R$^f$, and R$^f$ is optionally substituted carbocyclyl, heterocyclyl, aryl, or heteroaryl. In certain embodiments, $R^{41}$ is —C(=O)OR$^f$, and R$^f$ is optionally substituted alkyl. In certain embodiments, $R^{41}$ is —C(=O)

OR$^f$, and R$^f$ is optionally substituted alkenyl. In certain embodiments, R$^{41}$ is —C(=O)OR$^f$, and R$^f$ is optionally substituted carbocyclyl, heterocyclyl, aryl, or heteroaryl. In certain embodiments, R$^{41}$ is —C(=O)N(R$^f$)$_2$, and at least one R$^f$ is optionally substituted alkyl. In certain embodiments, R$^{41}$ is —C(=O)NHR$^f$, and R$^f$ is optionally substituted alkyl. In certain embodiments, R$^{41}$ is —C(=O)NHR$^f$, and R$^f$ is optionally substituted alkenyl. In certain embodiments, R$^{41}$ is —C(=O)NHR$^f$, and R$^f$ is optionally substituted carbocyclyl, heterocyclyl, aryl, or heteroaryl.

In certain embodiments, R$^{41}$ is —OR$^f$, e.g., —OH. In certain embodiments, R$^{41}$ is —OR$^f$, and R$^f$ is optionally substituted alkyl. In certain embodiments, R$^{41}$ is —OR$^f$, and R$^f$ is unsubstituted C$_{1-6}$ alkyl. In certain embodiments, R$^{41}$ is —OR$^f$, and R$^f$ is optionally substituted alkenyl. In certain embodiments, R$^{41}$ is —OR$^f$, and R$^f$ is optionally substituted carbocyclyl, optionally substituted heterocyclyl, optionally substituted aryl optionally substituted heteroaryl. In certain embodiments, R$^{41}$ is —OR$^f$, and R$^f$ is unsubstituted carbocyclyl, unsubstituted heterocyclyl, unsubstituted aryl unsubstituted heteroaryl. In certain embodiments, R$^{41}$ is —OR$^f$, and R$^f$ is optionally substituted acyl, e.g., R$^{41}$ is —OC(=O)R$^f$, —OC(=O) OR$^f$, or —OC(=O)N(R$^f$)$_2$. In certain embodiments, R$^{41}$ is —OR$^f$, and R$^f$ is an oxygen protecting group.

In certain embodiments, R$^{41}$ is —SR$^f$, e.g., —SH. In certain embodiments, R$^{41}$ is —SR$^f$, and R$^f$ is optionally substituted alkyl. In certain embodiments, R$^{41}$ is —SR$^f$, and R$^f$ is unsubstituted C$_{1-6}$ alkyl. In certain embodiments, R$^{41}$ is —SR$^f$, and R$^f$ is optionally substituted carbocyclyl, optionally substituted heterocyclyl, optionally substituted aryl optionally substituted heteroaryl. In certain embodiments, R$^{41}$ is —SR$^f$, and R$^f$ is unsubstituted carbocyclyl, unsubstituted heterocyclyl, unsubstituted aryl unsubstituted heteroaryl. In certain embodiments, R$^{41}$ is —SR$^f$, and R$^f$ is a sulfur protecting group.

In certain embodiments, R$^{41}$ is —N(R$^f$)$_2$, e.g., —NH$_2$, —NHR$^f$. In certain embodiments, R$^{41}$ is —NH(R$^f$), and R$^f$ is optionally substituted alkyl. In certain embodiments, R$^{41}$ is —N(R$^f$)$_2$, and at least one R$^f$ is optionally substituted alkyl. In certain embodiments, R$^{41}$ is —NH(R$^f$), and R$^f$ is unsubstituted alkyl. In certain embodiments, R$^{41}$ is —N(R$^f$)$_2$, and at least one R$^f$ is unsubstituted alkyl. In certain embodiments, R$^{41}$ is —NHR$^f$, and R$^f$ is optionally substituted carbocyclyl, optionally substituted heterocyclyl, optionally substituted aryl, or optionally substituted heteroaryl. In certain embodiments, R$^{41}$ is —NHR$^f$, and R$^f$ is unsubstituted carbocyclyl, unsubstituted heterocyclyl, unsubstituted aryl, or unsubstituted heteroaryl. In certain embodiments, R$^{41}$ is —NHR$^f$, and R$^f$ is optionally substituted acyl. e.g., R$^{41}$ is —NHC(=O)R$^f$. —NHC(=O)OR$^f$, or —NHC(=O)NHR$^f$. In certain embodiments, R$^{41}$ is —N(R$^f$)$_2$, and at least one R$^f$ is a nitrogen protecting group. In certain embodiments, R$^{41}$ is —N(R$^f$)$_2$, and both R$^f$ are joined to form an optionally substituted heterocyclic or optionally substituted heteroaryl ring. In certain embodiments, R$^{41}$ is —N(R$^f$)$_2$, and both R$^f$ are joined to form an unsubstituted heterocyclic or unsubstituted heteroaryl ring.

As generally defined herein, R$^{42}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN.

In certain embodiments, R$^{42}$ is hydrogen. In certain embodiments, R$^{42}$ is a non-hydrogen group. In certain embodiments, R$^{42}$ is halogen. In certain embodiments, R$^{42}$ is —F. In certain embodiments, R$^{42}$ is —Cl, —Br, or —I. In certain embodiments, R$^{42}$ is —NO$_2$. In certain embodiments, R$^{42}$ is —CN.

In certain embodiments, R$^{42}$ is optionally substituted alkyl, e.g., optionally substituted C$_{1-6}$ alkyl, optionally substituted C$_{1-2}$ alkyl, optionally substituted C$_{2-3}$ alkyl, optionally substituted C$_{3-4}$ alkyl, optionally substituted C$_{4-5}$ alkyl, or optionally substituted C$_{5-6}$ alkyl. In certain embodiments, R$^{42}$ is unsubstituted alkyl, e.g., unsubstituted C$_{1-6}$ alkyl, unsubstituted C$_{1-2}$ alkyl, unsubstituted C$_{2-3}$ alkyl, unsubstituted C$_{3-4}$ alkyl, unsubstituted C$_{4-5}$ alkyl, or unsubstituted C$_{5-6}$ alkyl. In certain embodiments, R$^{42}$ is methyl. In certain embodiments, R$^{42}$ is ethyl, propyl, or butyl. In certain embodiments, R$^{42}$ is haloalkyl, e.g., —CHF$_2$, —CHCl$_2$, —CH$_2$CHF$_2$, —CH$_2$CHCl$_2$. In certain embodiments, R$^{42}$ is perhaloalkyl, e.g., —CF$_3$, —CF$_2$CF$_3$, —CCl$_3$. In certain embodiments, R$^{42}$ is hydroxyalkyl, e.g., —CH$_2$OH, —CH$_2$CH$_2$OH, —CH$_2$OR$^f$, —CH$_2$CH$_2$OR$^f$. In certain embodiments, R$^{42}$ is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N(R$^f$)$_2$, —CH2CH2N(R$^f$)$_2$.

In certain embodiments. R$^{42}$ is optionally substituted alkenyl, e.g., optionally substituted C$_{2-6}$ alkenyl. In certain embodiments, R$^{42}$ is unsubstituted alkenyl, e.g., unsubstituted C$_{2-6}$ alkenyl. In certain embodiments, R$^{42}$ is vinyl, allyl, or prenyl. In certain embodiments, R$^{42}$ is optionally substituted alkynyl, e.g., optionally substituted C$_{1-6}$ alkynyl. In certain embodiments, R$^{42}$ is unsubstituted alkynyl, e.g., unsubstituted C$_{2-6}$ alkynyl.

In certain embodiments, R$^{42}$ is optionally substituted carbocyclyl, e.g., optionally substituted C$_{3-6}$ carbocyclyl, optionally substituted C$_{3-4}$ carbocyclyl, optionally substituted C$_{4-5}$ carbocyclyl, or optionally substituted C$_{5-6}$ carbocyclyl. In certain embodiments, R$^{42}$ is unsubstituted carbocyclyl, e.g., unsubstituted C$_{3-6}$ carbocyclyl. In some embodiments, R$^{42}$ is cyclopropyl, cyclobutyl, cyclopentyl, or cyclohexyl. In certain embodiments, R$^{42}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, R$^{42}$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, R$^{42}$ is optionally substituted aryl, e.g., optionally substituted phenyl. In certain embodiments, R$^{42}$ is unsubstituted aryl, e.g., unsubstituted phenyl. In certain embodiments, R$^{42}$ is optionally substituted heteroaryl, e.g., optionally substituted 5-6 membered heteroaryl, or optionally substituted 9-10 membered bicyclic heteroaryl. In certain embodiments, R$^{42}$ is unsubstituted heteroaryl, e.g., unsubstituted 5-6 membered heteroaryl, or unsubstituted 9-10 membered bicyclic heteroaryl. In certain embodiments, R$^{42}$ is optionally substituted aralkyl, e.g., optionally substituted benzyl. In certain embodiments, R$^{42}$ is optionally substituted heteroaralkyl, e.g., methyl substituted with an optionally substituted 5-6 membered heteroaryl ring. In certain embodiments, R$^{42}$ is unsubstituted aralkyl, e.g., unsubstituted benzyl. In certain embodiments, R$^{42}$ is unsubstituted heteroaralkyl, e.g., methyl substituted with an unsubstituted 5-6 membered heteroaryl ring.

In certain embodiments, R$^{42}$ is optionally substituted acyl, e.g., —CHO, —CO$_2$H, or —C(=O)NH$_2$. In certain embodiments, R$^{42}$ is —C(=O)R$^f$, —C(=O)OR$^f$, —C(=O)NH(R$^f$), or —C(=O)N(R$^f$)$_2$. In certain embodiments, R$^{42}$ is —C(=O)R$^f$, and R$^f$ is optionally substituted alkyl, e.g., —C(=O)Me. In certain embodiments, R$^{A2}$ is —C(=O)R$^f$, and R$^f$ is optionally substituted alkenyl. In certain embodiments, R$^{A2}$ is —C(=O)R$^f$, and R$^f$ is optionally substituted carbocyclyl, heterocyclyl, aryl, or heteroaryl. In certain embodiments, R$^{A2}$ is —C(=O)OR$^f$, and R$^f$ is optionally substituted alkyl. In certain embodiments, R$^{A2}$ is —C(=O)OR$^f$, and R$^f$ is optionally substituted alkenyl. In certain embodiments, R$^{A2}$ is —C(=O)OR$^f$, and R$^f$ is optionally substituted carbocyclyl, heterocyclyl, aryl, or heteroaryl. In certain embodiments, R$^{A2}$ is —C(=O)N(R$^f$)$_2$, and at least one R$^f$ is optionally substituted alkyl. In certain embodiments, R$^{A2}$ is —C(=O)NHR$^f$, and R$^f$ is optionally substituted alkyl. In certain embodiments, R$^{A2}$ is —C(=O)NHR$^f$, and R$^f$ is optionally substituted alkenyl. In certain embodiments, R$^{A2}$ is —C(=O)NHR$^f$, and R$^f$ is optionally substituted carbocyclyl, heterocyclyl, aryl, or heteroaryl.

In certain embodiments, R$^{A2}$ is —OR$^f$, e.g., —OH. In certain embodiments, R$^{A2}$ is —OR$^f$, and R$^f$ is optionally substituted alkyl. In certain embodiments, R$^{A2}$ is —OR$^f$, and R$^f$ is unsubstituted C$_{1-6}$ alkyl. In certain embodiments, R$^{A2}$ is —OR$^f$, and R$^f$ is optionally substituted alkenyl. In certain embodiments, R$^{A2}$ is —OR$^f$, and R$^f$ is optionally substituted carbocyclyl, optionally substituted heterocyclyl, optionally substituted aryl optionally substituted heteroaryl. In certain embodiments, R$^{A2}$ is —OR$^f$, and R$^f$ is unsubstituted carbocyclyl, unsubstituted heterocyclyl, unsubstituted aryl unsubstituted heteroaryl. In certain embodiments, R$^{A2}$ is —OR$^f$, and R$^f$ is optionally substituted acyl, e.g., R$^{A2}$ is —OC(=O)R$^f$, —OC(=O)OR$^f$, or —OC(=O)N(R$^f$)$_2$. In certain embodiments, R$^{A2}$ is —OR$^f$, and R$^f$ is a sulfur protecting group.

In certain embodiments, R$^{A2}$ is —SR$^f$, e.g., —SH. In certain embodiments, R$^{A2}$ is —SR$^f$, and R$^f$ is optionally substituted alkyl. In certain embodiments, R$^{A2}$ is —SR$^f$, and R$^f$ is unsubstituted C$_{1-6}$ alkyl. In certain embodiments, R$^{A2}$ is —SR$^f$, and R$^f$ is optionally substituted carbocyclyl, optionally substituted heterocyclyl, optionally substituted aryl optionally substituted heteroaryl. In certain embodiments, R$^{A2}$ is —SR$^f$, and R$^f$ is unsubstituted carbocyclyl, unsubstituted heterocyclyl, unsubstituted aryl unsubstituted heteroaryl. In certain embodiments, R$^{A2}$ is —SR$^f$, and R$^f$ is an oxygen protecting group.

In certain embodiments, R$^{A2}$ is —N(R$^f$)$_2$, e.g., —NH$_2$, —NHR$^f$. In certain embodiments, R$^{A2}$ is —NH(R$^f$), and R$^f$ is optionally substituted alkyl. In certain embodiments, R$^{A2}$ is —N(R$^f$)$_2$, and at least one R$^f$ is optionally substituted alkyl. In certain embodiments, R$^{A2}$ is —NH(R$^f$), and R$^f$ is unsubstituted alkyl. In certain embodiments, R$^{A2}$ is —N(R$^f$)$_2$, and at least one R$^f$ is unsubstituted alkyl. In certain embodiments, R$^{A2}$ is —NHR$^f$, and R$^f$ is optionally substituted carbocyclyl, optionally substituted heterocyclyl, optionally substituted aryl, or optionally substituted heteroaryl. In certain embodiments, R$^{A2}$ is —NHR$^f$, and R$^f$ is unsubstituted carbocyclyl, unsubstituted heterocyclyl, unsubstituted aryl, or unsubstituted heteroaryl. In certain embodiments, R$^{A2}$ is —NHR$^f$, and R$^f$ is optionally substituted acyl, e.g., R$^{A2}$ is —NHC(=O)R$^f$, —NHC(=O)OR$^f$, or —NHC(=O)NHR$^f$. In certain embodiments, R$^{A2}$ is —N(R$^f$)$_2$, and at least one R$^f$ is a nitrogen protecting group. In certain embodiments, R$^{A2}$ is —N(R$^f$)$_2$, and both R$^f$ are joined to form an optionally substituted heterocyclic or optionally substituted heteroaryl ring. In certain embodiments, R$^{A2}$ is —N(R$^f$)$_2$, and both R$^f$ are joined to form an unsubstituted heterocyclic or unsubstituted heteroaryl ring.

In some embodiments, R$^{A1}$ and R$^{A2}$ are the same. In some embodiments, R$^{A1}$ and R$^{A2}$ are different. In certain embodiments, both R$^{A1}$ and R$^{A2}$ are hydrogen. In certain embodiments, both R$^{A1}$ and R$^{A2}$ are optionally substituted halogen. In certain embodiments, both R$^{A1}$ and R$^{A2}$ are optionally substituted alkyl. In certain embodiments, both R$^{A1}$ and R$^{A2}$ are optionally substituted C$_{1-6}$ alkyl. In certain embodiments, both R$^{A1}$ and R$^{A2}$ are unsubstituted C$_{1-6}$ alkyl. In certain embodiments, both R$^{A1}$ and R$^{A2}$ are methyl.

R$^M$

As generally defined herein, R$^M$ is —CN, —N(R$^f$)$_2$, or —CH$_2$N(R$^f$)$_2$. In certain embodiments, R$^M$ is —CN. In certain embodiments, R$^M$ is —N(R$^f$)$_2$. In some embodiments, R$^M$ is —NHR$^f$. In some embodiments, R$^M$ is NH$_2$. In certain embodiments, R$^M$ is —CH$_2$N(R$^f$)$_2$. In certain embodiments, R$^M$ is —CH$_2$NHR$^f$. In certain embodiments, R$^M$ is —CH$_2$NH$_2$.

In certain embodiments, R$^M$ is —NH(R$^f$), and R$^f$ is optionally substituted alkyl. In certain embodiments, R$^M$ is —N(R$^f$)$_2$, and at least one R$^f$ is optionally substituted alkyl. In certain embodiments, R$^M$ is —NH(R$^f$), and R$^f$ is unsubstituted alkyl. In certain embodiments, R$^M$ is —N(R$^f$)$_2$, and at least one R$^f$ is unsubstituted alkyl. In certain embodiments, R$^M$ is —NHR$^f$, and R$^f$ is optionally substituted carbocyclyl, optionally substituted heterocyclyl, optionally substituted aryl, or optionally substituted heteroaryl. In certain embodiments, R$^M$ is —NHR$^f$, and R$^f$ is unsubstituted carbocyclyl, unsubstituted heterocyclyl, unsubstituted aryl, or unsubstituted heteroaryl. In certain embodiments, R$^M$ is —NHR$^f$, and R$^f$ is optionally substituted acyl, e.g., R$^M$ is —NHC(=O)R$^f$, —NHC(=O)OR$^f$, or —NHC(=O)NHR$^f$. In certain embodiments, R$^M$ is —N(R$^f$)$_2$, and at least one R$^f$ is a nitrogen protecting group. In certain embodiments, R$^M$ is —N(R$^f$)$_2$, and both R$^f$ are joined to form an optionally substituted heterocyclic or optionally substituted heteroaryl ring. In certain embodiments, R$^M$ is —N(R$^f$)$_2$, and both R$^f$ are joined to form an unsubstituted heterocyclic or unsubstituted heteroaryl ring.

In certain embodiments, R$^M$ is —CH$_2$NH(R$^f$), and R$^f$ is optionally substituted alkyl. In certain embodiments, R$^M$ is —CH$_2$N(R$^f$)$_2$, and at least one R$^f$ is optionally substituted alkyl. In certain embodiments, R$^M$ is —CH$_2$NH(R$^f$), and R$^f$ is unsubstituted alkyl. In certain embodiments, R$^M$ is —CH$_2$N(R$^f$)$_2$, and at least one R$^f$ is unsubstituted alkyl. In certain embodiments, R$^M$ is —CH$_2$NHR$^f$, and R$^f$ is optionally substituted carbocyclyl, optionally substituted heterocyclyl, optionally substituted aryl, or optionally substituted heteroaryl. In certain embodiments, R$^M$ is —CH$_2$NHR$^f$, and R$^f$ is unsubstituted carbocyclyl, unsubstituted heterocyclyl, unsubstituted aryl, or unsubstituted heteroaryl. In certain embodiments, R$^M$ is —CH$_2$NHR$^f$, and R$^f$ is optionally substituted acyl, e.g., R$^M$ is —CH$_2$NHC(=O)R$^f$, —CH$_2$NHC(=O)OR$^f$, or —CH$_2$NHC(=O)NHR$^f$. In certain embodiments, R$^M$ is —CH$_2$N(R$^f$)$_2$, and at least one R$^f$ is a nitrogen protecting group. In certain embodiments, R$^M$ is —CH$_2$N(R$^f$)$_2$, and both R$^f$ are joined to form an optionally substituted heterocyclic or optionally substituted heteroaryl ring. In certain embodiments, R$^M$ is —CH$_2$N(R$^f$)$_2$, and both R$^f$ are joined to form an unsubstituted heterocyclic or unsubstituted heteroaryl ring.

R$^B$ and X$^1$

As generally defined herein, R$^B$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —OR$^f$, —SR$^f$, —N(R$^f$)$_2$, —NO$_2$, or —CN. In certain embodiments, R$^B$ is —CH$_2$R$^M$, wherein R$^M$ is —CN, —N(R$^f$)$_2$, or —CH$_2$N(R$^f$)$_2$.

In certain embodiments, $R^B$ is hydrogen. In certain embodiments, $R^B$ is a non hydrogen group. In certain embodiments, $R^B$ is halogen. In certain embodiments, $R^B$ is —F. In certain embodiments, $R^B$ is —Cl, —Br, or —I. In certain embodiments, $R^B$ is —NO$_2$. In certain embodiments, $R^B$ is —CN.

In certain embodiments, $R^B$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^B$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^B$ is methyl. In certain embodiments, $R^B$ is ethyl, propyl, or butyl. In certain embodiments, $R^B$ is haloalkyl, e.g., —CHF$_2$, —CHCl$_2$, —CH$_2$CHF$_2$, —CH$_2$CHCl$_2$. In certain embodiments, $R^B$ is perhaloalkyl, e.g., —CF$_3$, —CF$_2$CF$_3$, —CCl$_3$. In certain embodiments, $R^B$ is hydroxyalkyl, e.g., —CH$_2$OH, —CH$_2$CH$_2$OH, —CH$_2$OR$^f$, —CH$_2$CH$_2$OR$^f$. In certain embodiments, $R^B$ is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N(R$^f$)$_2$, —CH2CH2N(R$^f$)$_2$.

In certain embodiments, $R^B$ is optionally substituted alkenyl, e.g., optionally substituted $C_{2-6}$ alkenyl. In certain embodiments, $R^B$ is unsubstituted alkenyl, e.g., unsubstituted $C_{2-6}$ alkenyl. In certain embodiments, $R^B$ is vinyl, allyl, or prenyl. In certain embodiments, $R^B$ is optionally substituted alkynyl, e.g., optionally substituted $C_{2-6}$ alkynyl. In certain embodiments, $R^B$ is unsubstituted alkynyl, e.g., unsubstituted $C_{2-6}$ alkynyl.

In certain embodiments, $R^B$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^B$ is unsubstituted carbocyclyl, e.g., unsubstituted $C_{3-6}$ carbocyclyl. In some embodiments, $R^B$ is cyclopropyl, cyclobutyl, cyclopentyl, or cyclohexyl. In certain embodiments, $R^B$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^B$ is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments. $R^B$ is optionally substituted aryl, e.g., optionally substituted phenyl. In certain embodiments, $R^B$ is unsubstituted aryl, e.g., unsubstituted phenyl. In certain embodiments, $R^B$ is optionally substituted heteroaryl, e.g., optionally substituted 5-6 membered heteroaryl, or optionally substituted 9-10 membered bicyclic heteroaryl. In certain embodiments, $R^B$ is unsubstituted heteroaryl, e.g., unsubstituted 5-6 membered heteroaryl, or unsubstituted 9-10 membered bicyclic heteroaryl. In certain embodiments, $R^B$ is optionally substituted aralkyl, e.g., optionally substituted benzyl. In certain embodiments, $R^B$ is optionally substituted heteroaralkyl, e.g., methyl substituted with an optionally substituted 5-6 membered heteroaryl ring. In certain embodiments, $R^B$ is unsubstituted aralkyl, e.g., unsubstituted benzyl. In certain embodiments, $R^B$ is unsubstituted heteroaralkyl, e.g., methyl substituted with an unsubstituted 5-6 membered heteroaryl ring.

In certain embodiments, $R^B$ is optionally substituted acyl, e.g., —CHO, —CO$_2$H, or —C(=O)NH$_2$. In certain embodiments, $R^B$ is —C(=O)R$^f$, —C(=O)OR$^f$, —C(=O)NH(R$^f$), or —C(=O)N(R$^f$)$_2$. In certain embodiments, $R^B$ is —C(=O)R$^f$, and R$^f$ is optionally substituted alkyl, e.g., —C(=O)Me. In certain embodiments; $R^B$ is —C(=O)R$^f$, and R$^f$ is optionally substituted alkenyl. In certain embodiments, $R^B$ is —C(=O)R$^f$, and R$^f$ is optionally substituted carbocyclyl, heterocyclyl, aryl, or heteroaryl. In certain embodiments, $R^B$ is —C(=O)OR$^f$, and R$^f$ is optionally substituted alkyl. In certain embodiments, $R^B$ is —C(=O)OR$^f$, and R$^f$ is optionally substituted alkenyl. In certain embodiments, $R^B$ is —C(=O)OR$^f$, and R$^f$ is optionally substituted carbocyclyl, heterocyclyl, aryl, or heteroaryl. In certain embodiments, $R^B$ is —C(=O)N(R$^f$)$_2$, and at least one R$^f$ is optionally substituted alkyl. In certain embodiments, $R^B$ is —C(=O)NHR$^f$, and R$^f$ is optionally substituted alkyl. In certain embodiments, $R^B$ is —C(=O)NHR$^f$, and R$^f$ is optionally substituted alkenyl. In certain embodiments, $R^B$ is —C(=O)NHR$^f$, and R$^f$ is optionally substituted carbocyclyl, heterocyclyl, aryl, or heteroaryl.

In certain embodiments, $R^B$ is —OR$^f$, e.g., —OH. In certain embodiments, $R^B$ is —OR$^f$, and R$^f$ is optionally substituted alkyl. In certain embodiments, $R^B$ is —OR$^f$, and R$^f$ is unsubstituted $C_{1-6}$ alkyl. In certain embodiments, $R^B$ is —OR$^f$, and R$^f$ is optionally substituted alkenyl. In certain embodiments, $R^B$ is —OR$^f$, and R$^f$ is optionally substituted carbocyclyl, optionally substituted heterocyclyl, optionally substituted aryl optionally substituted heteroaryl. In certain embodiments, $R^B$ is —OR$^f$, and R$^f$ is unsubstituted carbocyclyl, unsubstituted heterocyclyl, unsubstituted aryl unsubstituted heteroaryl. In certain embodiments, $R^B$ is —OR$^f$, and R$^f$ is optionally substituted acyl, e.g., $R^B$ is —OC(=O)R$^f$, —OC(=O)OR$^f$, or —OC(=O)N(R$^f$)$_2$. In certain embodiments, $R^B$ is —OR$^f$, and R$^f$ is an oxygen protecting group.

In certain embodiments, $R^B$ is —SR$^f$, e.g., —SH. In certain embodiments, $R^B$ is —SR$^f$, and R$^f$ is optionally substituted alkyl. In certain embodiments, $R^B$ is —SR$^f$, and R$^f$ is unsubstituted $C_{1-6}$ alkyl. In certain embodiments, $R^B$ is —SR$^f$, and R$^f$ is optionally substituted carbocyclyl, optionally substituted heterocyclyl, optionally substituted aryl optionally substituted heteroaryl. In certain embodiments, $R^B$ is —SR$^f$, and R$^f$ is unsubstituted carbocyclyl, unsubstituted heterocyclyl, unsubstituted aryl unsubstituted heteroaryl. In certain embodiments, $R^B$ is —SR$^f$, and R$^f$ is a sulfur protecting group.

In certain embodiments, $R^B$ is —N(R$^f$)$_2$, e.g., —NH$_2$, —NHR$^f$. In certain embodiments, $R^B$ is —NH(R$^f$), and R$^f$ is optionally substituted alkyl. In certain embodiments, $R^B$ is —N(R$^f$)$_2$, and at least one R$^f$ is optionally substituted alkyl. In certain embodiments, $R^B$ is —NH(R$^f$), and R$^f$ is unsubstituted alkyl. In certain embodiments, $R^B$ is —N(R$^f$)$_2$, and at least one R$^f$ is unsubstituted alkyl. In certain embodiments, $R^B$ is —NHR$^f$, and R$^f$ is optionally substituted carbocyclyl, optionally substituted heterocyclyl, optionally substituted aryl, or optionally substituted heteroaryl. In certain embodiments, $R^B$ is —NHR$^f$, and R$^f$ is unsubstituted carbocyclyl, unsubstituted heterocyclyl, unsubstituted aryl, or unsubstituted heteroaryl. In certain embodiments, $R^B$ is —NHR$^f$, and R$^f$ is optionally substituted acyl, e.g., $R^B$ is —NHC(=O)R$^f$, —NHC(=O)OR$^f$, or —NHC(=O)NHR$^f$. In certain embodiments, $R^B$ is —N(R$^f$)$_2$, and at least one R$^f$ is a nitrogen protecting group. In certain embodiments, $R^B$ is —N(R$^f$)$_2$, and both R$^f$ are joined to form an optionally substituted heterocyclic or optionally substituted heteroaryl ring. In certain embodiments, $R^B$ is —N($R^f$)$_2$, and both $R^f$ are joined to form an unsubstituted heterocyclic or unsubstituted heteroaryl ring.

As generally defined herein, $X^1$ is N or $CR^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —N($R^f$)$_2$, —NO$_2$, or —CN.

In certain embodiments, $X^1$ is N. In certain embodiments, $X^1$ is $CR^5$. In some embodiments, $X^1$ is CMe.

As generally defined herein, $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —N($R^f$)$_2$, —NO$_2$, or —CN. In certain embodiments, $R^5$ is —CH$_2$$R^M$, wherein $R^M$ is —CN, —N($R^f$)$_2$, or —CH$_2$N($R^f$)$_2$.

In certain embodiments, $R^5$ is hydrogen. In certain embodiments, $R^5$ is a non-hydrogen group. In certain embodiments, $R^5$ is halogen. In certain embodiments, $R^5$ is —F. In certain embodiments, $R^5$ is —Cl, —$^5$r, or —I. In certain embodiments, $R^5$ is —NO$_2$. In certain embodiments, $R^5$ is —CN.

In certain embodiments, $R^5$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^5$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^5$ is methyl. In certain embodiments, $R^5$ is ethyl, propyl, or butyl. In certain embodiments, $R^5$ is haloalkyl, e.g., —CHF$_2$, —CHCl$_2$, —CH$_2$CHF$_2$, —CH$_2$CHCl$_2$. In certain embodiments, $R^5$ is perhaloalkyl, e.g., —CF$_2$CF$_3$, —CCl$_3$. In certain embodiments, $R^5$ is hydroxyalkyl, e.g., —CH$_2$OH, —CH$_2$CH$_2$OH, —CH$_2$$OR^f$, —CH$_2$CH$_2$$OR^f$. In certain embodiments, $R^5$ is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N($R^f$)$_2$, —CH2CH2N($R^f$)$_2$.

In certain embodiments, $R^5$ is optionally substituted alkenyl, e.g., optionally substituted $C_{2-6}$ alkenyl. In certain embodiments, $R^5$ is unsubstituted alkenyl, e.g., unsubstituted $C_{2-6}$ alkenyl. In certain embodiments, $R^5$ is vinyl, allyl, or prenyl. In certain embodiments, $R^5$ is optionally substituted alkynyl, e.g., optionally substituted $C_{2-6}$ alkynyl. In certain embodiments, $R^5$ is unsubstituted alkynyl, e.g., unsubstituted $C_{2-6}$ alkynyl.

In certain embodiments, $R^5$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^5$ is unsubstituted carbocyclyl, e.g., unsubstituted $C_{3-6}$ carbocyclyl. In some embodiments, $R^5$ is cyclopropyl, cyclobutyl, cyclopentyl, or cyclohexyl. In certain embodiments, $R^5$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^5$ is unsubstituted heterocyclyl. e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^5$ is optionally substituted aryl, e.g., optionally substituted phenyl. In certain embodiments, $R^5$ is unsubstituted aryl, e.g., unsubstituted phenyl. In certain embodiments, $R^5$ is optionally substituted heteroaryl, e.g., optionally substituted 5-6 membered heteroaryl, or optionally substituted 9-10 membered bicyclic heteroaryl. In certain embodiments, $R^5$ is unsubstituted heteroaryl, e.g., unsubstituted 5-6 membered heteroaryl, or unsubstituted 9-10 membered bicyclic heteroaryl. In certain embodiments, $R^5$ is optionally substituted aralkyl, e.g., optionally substituted benzyl. In certain embodiments, $R^5$ is optionally substituted heteroaralkyl, e.g., methyl substituted with an optionally substituted 5-6 membered heteroaryl ring. In certain embodiments, $R^5$ is unsubstituted aralkyl, e.g., unsubstituted benzyl. In certain embodiments, $R^5$ is unsubstituted heteroaralkyl, e.g., methyl substituted with an unsubstituted 5-6 membered heteroaryl ring.

In certain embodiments, $R^5$ is optionally substituted acyl, e.g., —CHO, —CO$_2$H, or —C(=O)NH$_2$. In certain embodiments, $R^5$ is —C(=O)$R^f$, —C(=O)$OR^f$, —C(=O)NH($R^f$), or —C(=O)N($R^f$)$_2$. In certain embodiments, $R^5$ is —C(=O)$R^f$, and $R^f$ is optionally substituted alkyl, e.g., —C(=O)Me. In certain embodiments, $R^5$ is —C(=O)$R^f$, and $R^f$ is optionally substituted alkenyl. In certain embodiments, $R^5$ is —C(=O)$R^f$, and $R^f$ is optionally substituted carbocyclyl, heterocyclyl, aryl, or heteroaryl. In certain embodiments, $R^5$ is —C(=O)$OR^f$, and $R^f$ is optionally substituted alkyl. In certain embodiments, $R^3$ is —C(=O)$OR^f$, and $R^f$ is optionally substituted alkenyl. In certain embodiments, $R^5$ is —C(=O)$OR^f$, and $R^f$ is optionally substituted carbocyclyl, heterocyclyl, aryl, or heteroaryl. In certain embodiments, $R^5$ is —C(=O)N($R^f$)$_2$, and at least one $R^f$ is optionally substituted alkyl. In certain embodiments, $R^5$ is —C(=O)NH$R^f$, and $R^f$ is optionally substituted alkyl. In certain embodiments, $R^5$ is —C(=O)NH$R^f$, and $R^f$ is optionally substituted alkenyl. In certain embodiments, $R^5$ is —C(=O)NH$R^f$, and $R^f$ is optionally substituted carbocyclyl, heterocyclyl, aryl, or heteroaryl.

In certain embodiments, $R^5$ is —$OR^f$, e.g., —OH. In certain embodiments, $R^5$ is —$OR^f$, and $R^f$ is optionally substituted alkyl. In certain embodiments, $R^5$ is —$OR^f$, and $R^f$ is unsubstituted $C_{1-6}$ alkyl. In certain embodiments, $R^5$ is —$OR^f$, and $R^f$ is optionally substituted alkenyl. In certain embodiments, $R^5$ is —$OR^f$, and $R^f$ is optionally substituted carbocyclyl, optionally substituted heterocyclyl, optionally substituted aryl optionally substituted heteroaryl. In certain embodiments, $R^5$ is —$OR^f$, and $R^f$ is unsubstituted carbocyclyl, unsubstituted heterocyclyl, unsubstituted aryl unsubstituted heteroaryl. In certain embodiments, $R^5$ is —$OR^f$, and $R^f$ is optionally substituted acyl, e.g., $R^5$ is —OC(=O)$R^f$, —OC(=O)$OR^f$, or —OC(=O)N($R^f$)$_1$. In certain embodiments, $R^5$ is —$OR^f$, and $R^f$ is an oxygen protecting group.

In certain embodiments, $R^5$ is —$SR^f$, e.g., —SH. In certain embodiments, $R^5$ is —$SR^f$, and $R^f$ is optionally substituted alkyl. In certain, embodiments, $R^5$ is —$SR^f$, and $R^f$ is unsubstituted $C_{1-6}$ alkyl. In certain embodiments, $R^5$ is —$SR^f$, and $R^f$ is optionally substituted carbocyclyl, optionally substituted heterocyclyl, optionally substituted aryl optionally substituted heteroaryl. In certain embodiments, $R^5$ is —$SR^f$, and $R^f$ is unsubstituted carbocyclyl, unsubstituted heterocyclyl, unsubstituted aryl unsubstituted heteroaryl. In certain embodiments, $R^5$ is —$SR^f$, and $R^f$ is a sulfur protecting group.

In certain embodiments, $R^5$ is —N($R^f$)$_2$, e.g., —NH$R^f$. In certain embodiments, $R^5$ is —NH($R^f$), and $R^f$ is optionally substituted alkyl. In certain embodiments, $R^5$ is —N($R^f$)$_2$, and at least one $R^f$ is optionally substituted alkyl. In certain embodiments, $R^5$ is —NH($R^f$), and $R^f$ is unsubstituted alkyl. In certain embodiments, $R^5$ is —N($R^f$)$_1$, and at least one $R^f$ is unsubstituted alkyl. In certain embodiments, $R^5$ is —NH$R^f$, and $R^f$ is optionally substituted carbocyclyl, optionally substituted heterocyclyl, optionally substituted aryl, or optionally substituted heteroaryl. In certain embodiments, $R^5$ is —NH$R^f$, and $R^f$ is unsubstituted carbocyclyl, unsubstituted heterocyclyl, unsubstituted aryl, or unsubstituted heteroaryl. In certain embodiments, $R^5$ is —NH$R^f$, and $R^f$ is optionally substituted acyl, e.g., $R^5$ is —NHC(=O)$R^f$, —NHC(=O)O$R^f$, or —NHC(O)NH$R^f$. In certain embodiments, $R^5$ is —N($R^f$)$_2$, and at least one $R^f$ is a nitrogen protecting group. In certain embodiments, $R^5$ is —N($R^f$)$_2$, and both $R^f$ are joined to form an optionally substituted heterocyclic or optionally substituted heteroaryl ring. In certain embodiments, $R^5$ is —N($R^f$)$_1$, and both $R^f$ are joined to form an unsubstituted heterocyclic or unsubstituted heteroaryl ring.

In some embodiments, $X^1$ is $CR^5$, and $R^B$ and $R^5$ are the same. In some embodiments, $X^1$ is $CR^5$, and $R^B$ and $R^5$ are different. In certain embodiments, $X^1$ is $CR^5$, and both $R^B$ and $R^5$ are hydrogen. In certain embodiments, $X^1$ is $CR^5$, and both $R^B$ and $R^5$ are optionally substituted halogen. In certain embodiments, $X^1$ is $CR^5$, and both $R^B$ and $R^5$ are optionally substituted alkyl. In certain embodiments, $X^1$ is $CR^5$, and both $R^B$ and $R^5$ are optionally substituted $C_{1-6}$ alkyl. In certain embodiments, $X^1$ is $CR^5$, and both $R^B$ and $R^5$ are unsubstituted $C_{1-6}$ alkyl. In certain embodiments, $X^1$ is $CR^5$, and both $R^B$ and $R^5$ are methyl.

Ring C and $R^C$

As generally defined herein, Ring C is aryl or heteroaryl. For compounds of Formula (I), Ring C is substituted with at least one —CN group, and may be further substituted by 1, 2, 3, or 4 $R^C$. For compounds of Formula (II), Ring C may be substituted by 1, 2, 3, or 4 $R^C$. As generally defined herein, c is 0, 1, 2, 3, or 4. In certain embodiments, c is 0. In certain embodiments, c is 1. In certain embodiments, c is 2. In certain embodiments, c is 3. In certain embodiments, c is 4. In certain embodiments, c is 0, 1, 2, or 3. In certain embodiments, c is 0, 1, or 2. In certain embodiments, c is 0 or 1. In certain embodiments, c is 1, 2, 3, or 4. In certain embodiments, c is 2, 3, or 4. In certain embodiments, c is 3 or 4.

In certain embodiments, Ring C is aryl. In certain embodiments, Ring C is monocyclic aryl. In certain embodiments, Ring C is phenyl. In certain embodiments, Ring C is bicyclic aryl. In certain embodiments, Ring C is naphthyl.

In certain embodiments, Ring C is heteroaryl. In certain embodiments, Ring C is monocyclic heteroaryl. In certain embodiments, Ring C is 5-membered heteroaryl. In some embodiments, Ring C is pyrrolyl, furanyl, or thiophenyl. In some embodiments, Ring C is imidazolyl, pyrazolyl, oxazolyl, isoxazolyl, thiazolyl, and isothiazolyl. In some embodiments, Ring C is triazolyl, oxadiazolyl, thiadiazolyl, or tetrazolyl. In certain embodiments, Ring C is 6-membered heteroaryl. In some embodiments, Ring C is pyridinyl. In some embodiments, Ring C is pyridazinyl, pyrimidinyl, and pyrazinyl. In certain embodiments, Ring C is bicyclic heteroaryl. In certain embodiments, Ring C is 9- to 10-membered bicyclic heteroaryl. In some embodiments, Ring C is indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, or purinyl. In some embodiments, Ring C is naphthyridinyl, pteridinyl, quinolinyl, isoquinolinyl, cinnolinyl, quinoxalinyl, phthalazinyl, or quinazolinyl.

In certain embodiments, Ring C is of formula:

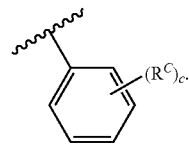

In certain embodiments, Ring C is of formula:

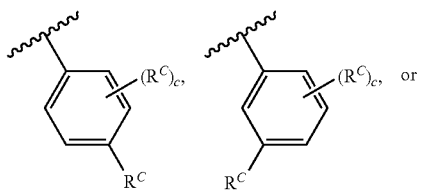

In certain embodiments, Ring C is of formula:

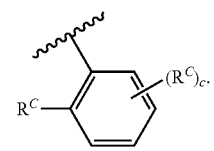

In certain embodiments, Ring C is of formula:

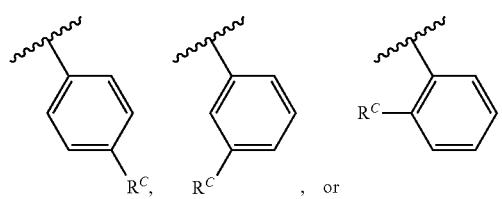

In certain embodiments, Ring C is of formula:

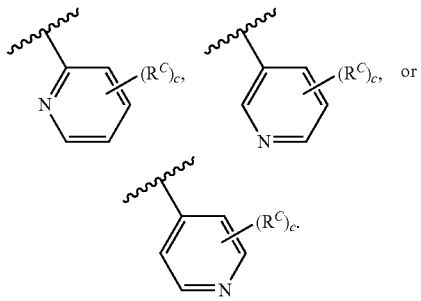

In certain embodiments, Ring C is of formula:

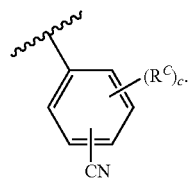

In certain embodiments, Ring C is of formula:

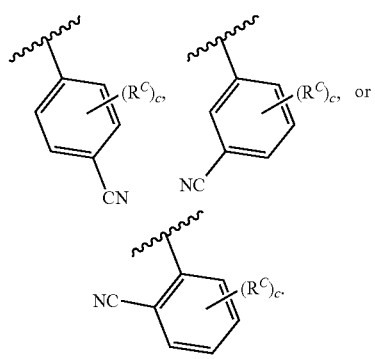

In certain embodiments, Ring C is of formula:

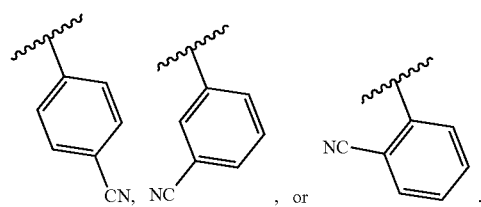

In certain embodiments, Ring C is of formula:

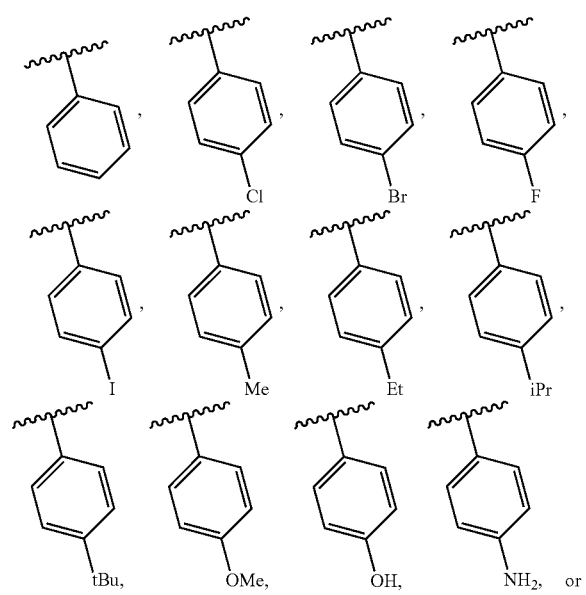

-continued

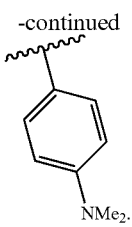

In certain embodiments, Ring C is of formula:

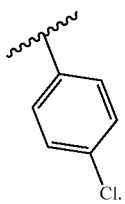

In certain embodiments, Ring C is of formula:

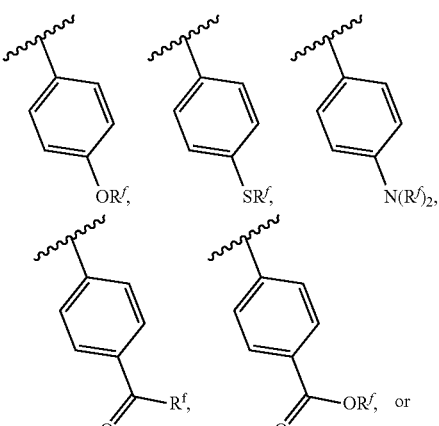

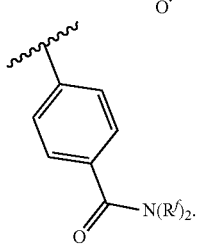

As generally defined herein, $R^C$ is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^f$, —$SR^f$, —$N(R^f)_2$, —$NO_2$, or —CN.

In certain embodiments, $R^C$ is halogen. In certain embodiments, $R^C$ is —F. In certain embodiments, $R^C$ is —Cl, —$^C$r, or —I. In certain embodiments, $R^C$ is —$NO_2$. In certain embodiments, $R^C$ is —CN.

In certain embodiments, $R^C$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^C$ is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, $R^C$ is methyl. In certain embodiments, $R^C$ is ethyl, propyl, or butyl. In certain embodiments, $R^C$ is haloalkyl, e.g., —$CHF_2$, —$CHCl_2$, —$CH_2CHF_2$, —$CH_2CHCl_2$. In certain embodiments, $R^C$ is perhaloalkyl, e.g., —$CF_3$, —$CF_2CF_3$, —$CCl_3$. In certain embodiments, $R^C$ is hydroxyalkyl, e.g., —$CH_2OH$, —$CH_2CH_2OH$, —$CH_2OR^f$, —$CH_2CH_2OR^f$. In certain embodiments, $R^C$ is aminoalkyl, e.g., —$CH_2NH_2$, —$CH_2CH_2NH_2$, —$CH_2NMe_2$, —$CH_2CH_2NMe_2$, —$CH_2N(R^f)_2$, —$CH2CH2N(R^f)_2$.

In certain embodiments, $R^C$ is optionally substituted alkenyl, e.g., optionally substituted $C_{2-6}$ alkenyl. In certain embodiments, $R^C$ is unsubstituted alkenyl, e.g., unsubstituted $C_{2-6}$ alkenyl. In certain embodiments, $R^C$ is vinyl, allyl, or prenyl. In certain embodiments, $R^C$ is optionally substituted alkynyl, e.g., optionally substituted $C_{2-6}$ alkynyl. In certain embodiments, $R^C$ is unsubstituted alkynyl, e.g., unsubstituted $C_{2-6}$ alkynyl.

In certain embodiments, $R^C$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, $R^C$ is unsubstituted carbocyclyl, e.g., unsubstituted $C_{3-6}$ carbocyclyl. In some embodiments, $R^C$ is cyclopropyl, cyclobutyl, cyclopentyl, or cyclohexyl. In certain embodiments, $R^C$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, $R^C$ is unsubstituted heterocyclyl. e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, $R^C$ is optionally substituted aryl, e.g., optionally substituted phenyl. In certain embodiments, $R^C$ is unsubstituted aryl, e.g., unsubstituted phenyl. In certain embodiments, $R^C$ is optionally substituted heteroaryl, e.g., optionally substituted 5-6 membered heteroaryl, or optionally substituted 9-10 membered bicyclic heteroaryl. In certain embodiments, $R^C$ is unsubstituted heteroaryl, e.g., unsubstituted 5-6 membered heteroaryl, or unsubstituted 9-10 membered bicyclic heteroaryl. In certain embodiments, $R^C$ is optionally substituted aralkyl, e.g., optionally substituted benzyl. In certain embodiments, $R^C$ is optionally substituted heteroaralkyl, e.g., methyl substituted with an optionally substituted 5-6 Membered heteroaryl ring. In certain embodiments, $R^C$ is unsubstituted aralkyl, e.g., unsubstituted benzyl. In certain embodiments, $R^C$ is unsubstituted heteroaralkyl, e.g., methyl substituted with an unsubstituted 5-6 membered heteroaryl ring.

In certain embodiments, $R^C$ is optionally substituted acyl, e.g., —CHO, —$CO_2H$, or —C(=O)$NH_2$. In certain embodiments, $R^C$ is —C(=O)$R^f$, —C(=O)$OR^f$, —C(=O)NH($R^f$), or —C(=O)N($R^f$)$_2$. In certain embodiments, $R^C$ is —C(=O)$R^f$, and $R^f$ is optionally substituted alkyl, e.g., —C(=O)Me. In certain embodiments, $R^C$ is —C(=O)$R^f$, and $R^f$ is optionally substituted alkenyl. In certain embodiments, $R^C$ is —C(=O)$R^f$, and $R^f$ is optionally substituted carbocyclyl, heterocyclyl, aryl, or heteroaryl. In certain embodiments, $R^C$ is —C(=O)$OR^f$, and $R^f$ is optionally substituted alkyl. In certain embodiments, $R^C$ is —C(=O)$OR^f$, and $R^f$ is optionally substituted alkenyl. In certain embodiments, $R^C$ is —C(=O)$OR^f$, and $R^f$ is optionally substituted carbocyclyl, heterocyclyl, aryl, or heteroaryl. In certain embodiments, $R^C$ is —C(=O)N($R^f$)$_2$, and at least one $R^f$ is optionally substituted alkyl. In certain embodiments, $R^C$ is —C(=O)NH$R^f$, and $R^f$ is optionally substituted alkyl. In certain embodiments, $R^C$ is —C(=O)NH$R^f$, and $R^f$ is optionally substituted alkenyl. In certain embodiments, $R^C$ is —C(=O)NH$R^f$, and $R^f$ is optionally substituted carbocyclyl, heterocyclyl, aryl, or heteroaryl.

In certain embodiments, $R^C$ is optionally substituted sulfonyl, e.g., —S(=O)$_2$OH. In certain embodiments, $R^C$ is —S(=O)$_2R^f$, —S(=O)$_2OR^f$, —S(=O)$_2$NH($R^f$), or —S(=O)$_2$N($R^f$)$_2$. In certain embodiments, $R^C$ is —S(=O)$_2R^f$, and $R^f$ is optionally substituted alkyl, e.g., —S(=O)$_2$Me. In certain embodiments, $R^C$ is —S(=O)$_2R^f$, and $R^f$ is optionally substituted carbocyclyl, heterocyclyl, aryl, or heteroaryl. In certain embodiments, $R^C$ is —S(=O)$_2OR^f$, and $R^f$ is optionally substituted alkyl. In certain embodiments, $R^C$ is —S(=O)$_2OR^f$, and $R^f$ is optionally substituted aryl. In certain embodiments, $R^C$ is —S(=O)$_2$N($R^f$)$_2$, and at least one $R^f$ is optionally substituted alkyl. In certain embodiments, $R^C$ is —S(=O)$_2$NH$R^f$, and $R^f$ is optionally substituted carbocyclyl, heterocyclyl, aryl, or heteroaryl.

In certain embodiments, $R^C$ is —$OR^f$, e.g., —OH. In certain embodiments, $R^C$ is —$OR^f$, and $R^f$ is optionally substituted alkyl. In certain embodiments, $R^C$ is —$OR^f$, and $R^f$ is unsubstituted $C_{1-6}$ alkyl. In certain embodiments, $R^C$ is —$OR^f$, and $R^f$ is optionally substituted alkenyl. In certain embodiments, $R^C$ is —$OR^f$, and $R^f$ is optionally substituted carbocyclyl, optionally substituted heterocyclyl, optionally substituted aryl optionally substituted heteroaryl. In certain embodiments, $R^C$ is —$OR^f$, and $R^f$ is unsubstituted carbocyclyl, unsubstituted heterocyclyl, unsubstituted aryl unsubstituted heteroaryl. In certain embodiments, $R^C$ is —$OR^f$, and $R^f$ is optionally substituted acyl, e.g., $R^C$ is —OC(=O)$R^f$, —OC(=O)$OR^f$, or —OC(=O)N($R^f$)$_2$. In certain embodiments, $R^C$ is —$OR^f$, and $R^f$ is an oxygen protecting group.

In certain embodiments, $R^C$ is —$SR^f$, e.g., —SH. In certain embodiments, $R^C$ is —$SR^f$, and $R^f$ is optionally substituted alkyl. In certain embodiments, $R^C$ is —$SR^f$, and $R^f$ is unsubstituted $C_{1-6}$ alkyl. In certain embodiments, $R^C$ is —$SR^f$, and $R^f$ is optionally substituted carbocyclyl, optionally substituted heterocyclyl, optionally substituted aryl optionally substituted heteroaryl. In certain embodiments, $R^C$ is —$SR^f$, and $R^f$ is unsubstituted carbocyclyl, unsubstituted heterocyclyl, unsubstituted aryl unsubstituted heteroaryl. In certain embodiments, $R^C$ is —$SR^f$, and $R^f$ is a sulfur protecting group.

In certain embodiments, $R^C$ is —N($R^f$)$_2$, e.g., —$NH_2$, —NH$R^f$. In certain embodiments, $R^C$ is —NH($R^f$), and $R^f$ is optionally substituted alkyl. In certain embodiments, $R^C$ is —N($R^f$)$_2$, and at least one $R^f$ is optionally substituted alkyl. In certain embodiments, $R^C$ is —NH($R^f$), and $R^f$ is unsubstituted alkyl. In certain embodiments, $R^C$ is —N($R^f$)$_2$, and at least one $R^f$ is unsubstituted alkyl. In certain embodiments, $R^C$ is —NH$R^f$, and $R^f$ is optionally substituted carbocyclyl, optionally substituted heterocyclyl, optionally substituted aryl, or optionally substituted heteroaryl. In certain embodiments, $R^C$ is —NH$R^f$, and $R^f$ is unsubstituted carbocyclyl, unsubstituted heterocyclyl, unsubstituted aryl, or unsubstituted heteroaryl. In certain embodiments, $R^C$ is —NH$R^f$, and $R^f$ is optionally substituted acyl, e.g., $R^C$ is —NHC(=O)$R^f$, —NHC(=O)$OR^f$, or —NHC(=O)NH$R^f$. In certain embodiments, $R^C$ is —N($R^f$)$_2$, and at least one $R^f$ is a nitrogen protecting group. In certain embodiments, $R^C$ is —N($R^f$)$_2$, and both $R^f$ are joined to form an optionally substituted heterocyclic or optionally substituted heteroaryl ring. In certain embodiments, $R^C$ is —N($R^f$)$_2$, and both $R^f$ are joined to form an unsubstituted heterocyclic or unsubstituted heteroaryl ring.

In certain embodiments, an $R^C$ attached para to the diazepine is halogen. In certain embodiments, an $R^C$ attached para to the diazepine is —F. In certain embodiments, an $R^C$ attached para to the diazepine is —Cl, —Br, or —I. In certain embodiments, an $R^C$ attached para to the diazepine is —NO$_2$. In certain embodiments, an $R^C$ attached para to the diazepine is —CN.

In certain embodiments, an $R^C$ attached para to the diazepine is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, an $R^C$ attached para to the diazepine is unsubstituted alkyl, e.g., unsubstituted $C_{1-6}$ alkyl, unsubstituted $C_{1-2}$ alkyl, unsubstituted $C_{2-3}$ alkyl, unsubstituted $C_{3-4}$ alkyl, unsubstituted $C_{4-5}$ alkyl, or unsubstituted $C_{5-6}$ alkyl. In certain embodiments, an $R^C$ attached para to the diazepine is methyl. In certain embodiments, an $R^C$ attached para to the diazepine is ethyl, propyl, or butyl. In certain embodiments, an $R^C$ attached para to the diazepine is haloalkyl, e.g., —CHF$_2$, —CHCl$_2$, —CH$_2$CHF$_2$, —CH$_2$CHCl$_2$. In certain embodiments, an $R^C$ attached para to the diazepine is perhaloalkyl, e.g., —CF$_3$, —CF$_2$CF$_3$, —CCl$_3$. In certain embodiments, an $R^C$ attached para to the diazepine is hydroxyalkyl, e.g., —CH$_2$OH, —CH$_2$CH$_2$OH, —CH$_2$O$R^f$, —CH$_2$CH$_2$O$R^f$. In certain embodiments, an $R^C$ attached para to the diazepine is aminoalkyl, e.g., —CH$_2$NH$_2$, —CH$_2$CH$_2$NH$_2$, —CH$_2$NMe$_2$, —CH$_2$CH$_2$NMe$_2$, —CH$_2$N($R^f$)$_2$, —CH2CH2N($R^f$)$_2$.

In certain embodiments, an $R^C$ attached para to the diazepine is optionally substituted alkenyl, e.g., optionally substituted $C_{2-6}$ alkenyl. In certain embodiments, an $R^C$ attached para to the diazepine is unsubstituted alkenyl, e.g., unsubstituted $C_{2-6}$ alkenyl. In certain embodiments, an $R^C$ attached para to the diazepine is vinyl, allyl, or prenyl. In certain embodiments, an $R^C$ attached para to the diazepine is optionally substituted alkynyl, e.g., optionally substituted $C_{2-6}$ alkynyl. In certain embodiments, an $R^C$ attached para to the diazepine is unsubstituted alkynyl, e.g., unsubstituted $C_{2-6}$ alkynyl.

In certain embodiments, an $R^C$ attached para to the diazepine is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments, an $R^C$ attached para to the diazepine is unsubstituted carbocyclyl, e.g., unsubstituted $C_{3-6}$ carbocyclyl. In some embodiments, an $R^C$ attached para to the diazepine is cyclopropyl, cyclobutyl, cyclopentyl, or cyclohexyl. In certain embodiments, an $R^C$ attached para to the diazepine is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, an $R^C$ attached para to the diazepine is unsubstituted heterocyclyl, e.g., unsubstituted 3-6 membered heterocyclyl, unsubstituted 3-4 membered heterocyclyl, unsubstituted 4-5 membered heterocyclyl, or unsubstituted 5-6 membered heterocyclyl.

In certain embodiments, an $R^C$ attached para to the diazepine is optionally substituted aryl, e.g., optionally substituted phenyl. In certain embodiments, an $R^C$ attached para to the diazepine is unsubstituted aryl, e.g., unsubstituted phenyl. In certain embodiments, an $R^C$ attached para to the diazepine is optionally substituted heteroaryl, e.g., optionally substituted 5-6 membered heteroaryl, or optionally substituted 9-10 membered bicyclic heteroaryl. In certain embodiments, an $R^C$ attached para to the diazepine is unsubstituted heteroaryl, e.g., unsubstituted 5-6 membered heteroaryl, or unsubstituted 9-10 membered bicyclic heteroaryl. In certain embodiments, an $R^C$ attached para to the diazepine is optionally substituted aralkyl, e.g., optionally substituted benzyl. In certain embodiments, an $R^C$ attached para to the diazepine is optionally substituted heteroaralkyl, e.g., methyl substituted with an optionally substituted 5-6 membered heteroaryl ring. In certain embodiments, an $R^C$ attached para to the diazepine is unsubstituted aralkyl, e.g., unsubstituted benzyl. In certain embodiments, an $R^C$ attached para to the diazepine is unsubstituted heteroaralkyl, e.g., methyl substituted with an unsubstituted 5-6 membered heteroaryl ring.

In certain embodiments, an $R^C$ attached para to the diazepine is optionally substituted acyl, e.g., —CHO, —CO$_2$H, or —C(=O)NH$_2$. In certain embodiments, an $R^C$ attached para to the diazepine is —C(=O)R$^1$, —C(=O)O$R^f$, —C(=O)NH($R^f$), or —C(=O)N($R^f$)$_2$. In certain embodiments, an $R^C$ attached para to the diazepine is —C(=O)$R^f$, and $R^f$ is optionally substituted alkyl, e.g., —C(=O)Me. In certain embodiments, an $R^C$ attached para to the diazepine is —C(=O)$R^f$, and $R^f$ is optionally substituted alkenyl. In certain embodiments, an $R^C$ attached para to the diazepine is —C(=O)$R^f$, and $R^f$ is optionally substituted carbocyclyl, heterocyclyl, aryl, or heteroaryl. In certain embodiments, an $R^C$ attached para to the diazepine is —C(=O)O$R^f$, and $R^f$ is optionally substituted alkyl. In certain embodiments, an $R^C$ attached para to the diazepine is —C(=O)O$R^f$, and $R^f$ is optionally substituted alkenyl. In certain embodiments, an $R^C$ attached para to the diazepine is —C(=O)O$R^f$, and $R^f$ is optionally substituted carbocyclyl, heterocyclyl, aryl, or heteroaryl. In certain embodiments, an $R^C$ attached para to the diazepine is —C(=O)N($R^f$)$_2$, and at least one $R^f$ is optionally substituted alkyl. In certain embodiments, an $R^C$ attached para to the diazepine is —C(=O)NH$R^f$, and $R^f$ is optionally substituted alkyl. In certain embodiments, an $R^C$ attached para to the diazepine is —C(=O)NH$R^f$, and $R^f$ is optionally substituted alkenyl. In certain embodiments, an $R^C$ attached para to the diazepine is —C(=O)NH$R^f$, and $R^f$ is optionally substituted carbocyclyl, heterocyclyl, aryl, or heteroaryl.

In certain embodiments, an $R^C$ attached para to the diazepine is —O$R^f$, e.g., —OH. In certain embodiments, an $R^C$ attached para to the diazepine is —O$R^f$, and $R^f$ is optionally substituted alkyl. In certain embodiments, an $R^C$ attached para to the diazepine is —O$R^f$, and $R^f$ is unsubstituted $C_{1-6}$ alkyl. In certain embodiments, an $R^C$ attached para to the diazepine is —O$R^f$, and $R^f$ is optionally substituted alkenyl. In certain embodiments, an $R^C$ attached para to the diazepine is —O$R^f$, and $R^f$ is optionally substituted carbocyclyl, optionally substituted heterocyclyl, optionally substituted aryl optionally substituted heteroaryl. In certain embodiments, an $R^C$ attached para to the diazepine is —O$R^f$, and $R^f$ is unsubstituted carbocyclyl, unsubstituted heterocyclyl, unsubstituted aryl unsubstituted heteroaryl. In certain embodiments, an $R^C$ attached para to the diazepine is —O$R^f$, and $R^f$ is optionally substituted acyl, e.g., an $R^C$ attached para to the diazepine is —OC(=O)$R^f$, —OC(=O)O$R^f$, or —OC(=O)N($R^f$)$_2$. In certain embodiments, an $R^C$ attached para to the diazepine is —O$R^f$, and $R^f$ is an oxygen protecting group.

In certain embodiments, an R$^C$ attached para to the diazepine is optionally substituted sulfonyl, e.g., —S(=O)$_2$OH. In certain embodiments, an R$^C$ attached para to the diazepine is —S(=O)$_2$R$^f$, —S(=O)$_2$OR$^f$, —S(=O)$_2$NH(R$^f$), or —S(=O)$_2$N(R$^f$)$_2$. In certain embodiments, an R$^C$ attached para to the diazepine is —S(=O)$_2$R$^f$, and R$^f$ is optionally substituted alkyl, e.g., —S(=O)$_2$Me. In certain embodiments, an R$^C$ attached para to the diazepine is —S(=O)$_2$R$^f$, and R$^f$ is optionally substituted carbocyclyl, heterocyclyl, aryl, or heteroaryl. In certain embodiments, an R$^C$ attached para to the diazepine is —S(=O)$_2$OR$^f$, and R$^f$ is optionally substituted alkyl. In certain embodiments, an R$^C$ attached para to the diazepine is —S(=O)$_2$OR$^f$, and R$^f$ is optionally substituted aryl. In certain embodiments, an R$^C$ attached para to the diazepine is —S(=O)$_2$N(R$^f$)$_2$, and at least one R$^f$ is optionally substituted alkyl. In certain embodiments, an R$^C$ attached para to the diazepine is —S(=O)$_2$NHR$^f$, and R$^f$ is optionally substituted carbocyclyl, heterocyclyl, aryl, or heteroaryl.

In certain embodiments, an R$^C$ attached para to the diazepine is —SR$^f$, e.g., —SH. In certain embodiments, an R$^C$ attached para to the diazepine is —SR$^f$, and R$^f$ is optionally substituted alkyl. In certain embodiments, an R$^C$ attached para to the diazepine is —SR$^f$, and R$^f$ is unsubstituted C$_{1-6}$ alkyl. In certain embodiments, an R$^C$ attached para to the diazepine is —SR$^f$, and R$^f$ is optionally substituted carbocyclyl, optionally substituted heterocyclyl, optionally substituted aryl optionally substituted heteroaryl. In certain embodiments, an R$^C$ attached para to the diazepine is —SR$^f$, and R$^f$ is unsubstituted carbocyclyl, unsubstituted heterocyclyl, unsubstituted aryl unsubstituted heteroaryl. In certain embodiments, an R$^C$ attached para to the diazepine is —SR$^f$, and R$^f$ is a sulfur protecting group.

In certain embodiments, an R$^C$ attached para to the diazepine is —N(R$^f$)$_2$, e.g., —NH$_2$, —NHR$^f$. In certain embodiments, an R$^C$ attached, para to the diazepine is —NH(R$^f$), and R$^f$ is optionally substituted alkyl. In certain embodiments, an R$^C$ attached para to the diazepine is —N(R$^f$)$_2$, and at least one R$^f$ is optionally substituted alkyl. In certain embodiments, an R$^C$ attached para to the diazepine is —NH(R$^f$), and R$^f$ is unsubstituted alkyl. In certain embodiments, an R$^C$ attached para to the diazepine is —N(R$^f$)$_2$, and at least one R$^f$ is unsubstituted alkyl. In certain embodiments, an R$^C$ attached para to the diazepine is —NHR$^f$, and R$^f$ is optionally substituted carbocyclyl, optionally substituted heterocyclyl, optionally substituted aryl, or optionally substituted heteroaryl. In certain embodiments, an R$^C$ attached para to the diazepine is —NHR$^f$, and R$^f$ is unsubstituted carbocyclyl, unsubstituted heterocyclyl, unsubstituted aryl, or unsubstituted heteroaryl. In certain embodiments, an R$^C$ attached para to the diazepine is —NHR$^f$, and R$^f$ is optionally substituted acyl, e.g., an R$^C$ attached para to the diazepine is —NHC(=O)R$^f$, —NHC(=O)OR$^f$, or —NHC(=O)NHR$^f$. In certain embodiments, an R$^C$ attached para to the diazepine is —N(R$^f$)$_2$, and at least one R$^f$ is a nitrogen protecting group. In certain embodiments, an R$^C$ attached para to the diazepine is —N(R$^f$)$_2$, and both R$^f$ are joined to form an optionally substituted heterocyclic or optionally substituted heteroaryl ring. In certain embodiments, an R$^C$ attached para to the diazepine is —N(R$^f$)$_2$, and both R$^f$ are joined to form an unsubstituted heterocyclic or unsubstituted heteroaryl ring.

In certain embodiments, the compound of Formula (I) is a compound listed in Table 1.

TABLE 1

Exemplary compounds of Formula (I)

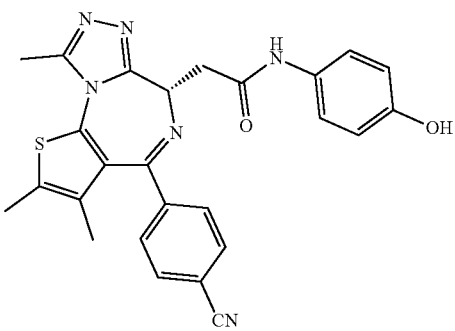 [SMILES: Cc1sc2c(c1C)C(c1ccc(C#N)cc1)=N[C@@H](CC(=O)Nc1ccc(O)cc1)c1nnc(C)n1-2]

101

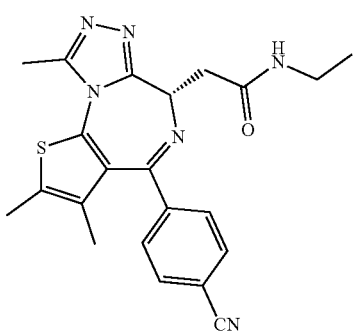 [SMILES: CCNC(=O)C[C@@H]1N=C(c2ccc(C#N)cc2)c2c(sc(C)c2C)-n2c(C)nnc21]

102

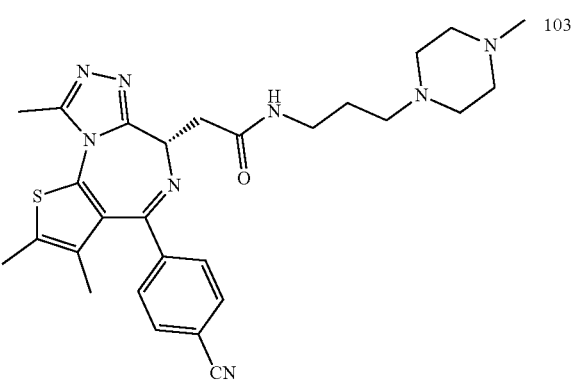

103

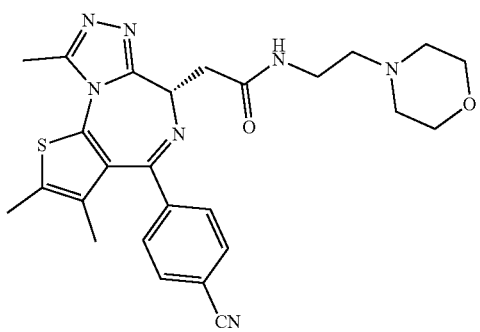 [SMILES: Cc1sc2c(c1C)C(c1ccc(C#N)cc1)=N[C@@H](CC(=O)NCCN1CCOCC1)c1nnc(C)n1-2]

104

TABLE 1-continued
Exemplary compounds of Formula (I)
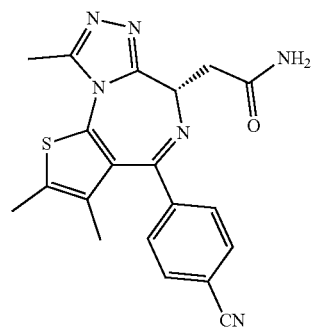 [SMILES: Cc1sc2c(c1C)C(c1ccc(C#N)cc1)=N[C@@H](CC(N)=O)c1nnc(C)n1-2] 105
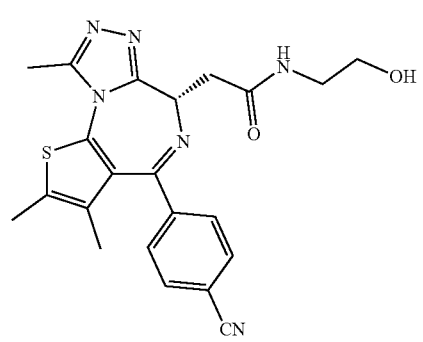 [SMILES: Cc1sc2c(c1C)C(c1ccc(C#N)cc1)=N[C@@H](CC(=O)NCCO)c1nnc(C)n1-2] 106
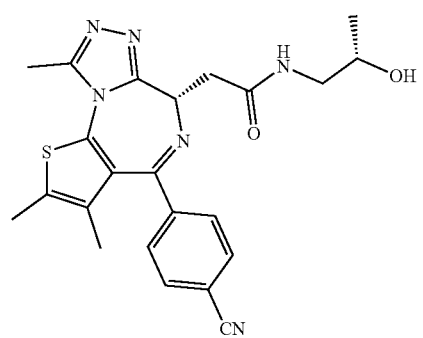 [SMILES: Cc1sc2c(c1C)C(c1ccc(C#N)cc1)=N[C@@H](CC(=O)NC[C@H](C)O)c1nnc(C)n1-2] 107
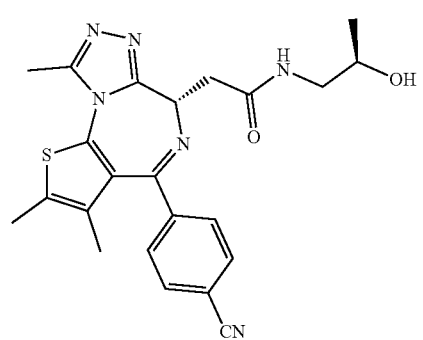 [SMILES: Cc1sc2c(c1C)C(c1ccc(C#N)cc1)=N[C@@H](CC(=O)NC[C@@H](C)O)c1nnc(C)n1-2] 108
TABLE 1-continued
Exemplary compounds of Formula (I)
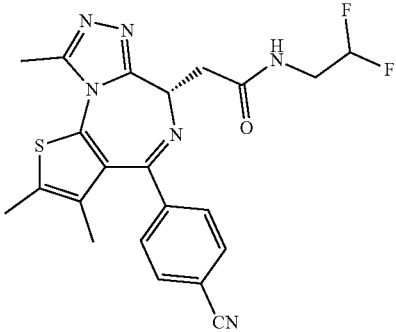 [SMILES: Cc1sc2c(c1C)C(c1ccc(C#N)cc1)=N[C@@H](CC(=O)NCC(F)F)c1nnc(C)n1-2] 109
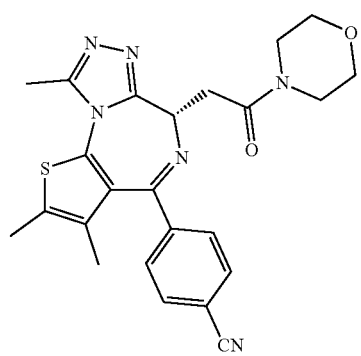 [SMILES: Cc1sc2c(c1C)C(c1ccc(C#N)cc1)=N[C@@H](CC(=O)N1CCOCC1)c1nnc(C)n1-2] 110
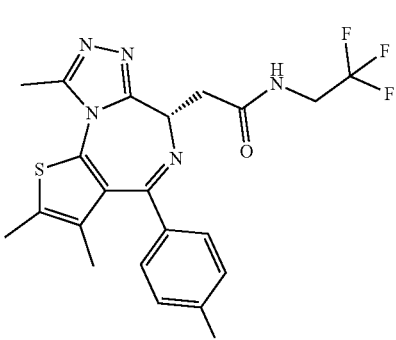 111
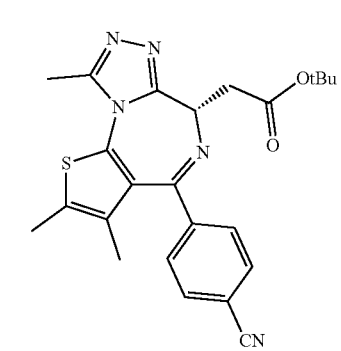 [SMILES: Cc1sc2c(c1C)C(c1ccc(C#N)cc1)=N[C@@H](CC(=O)OC(C)(C)C)c1nnc(C)n1-2] 100

TABLE 1-continued
Exemplary compounds of Formula (I)
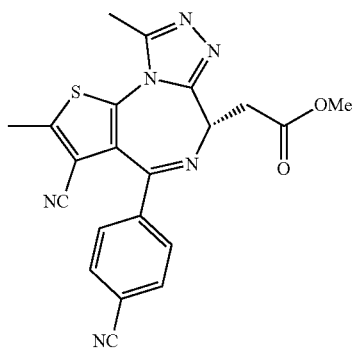 [SMILES: COC(=O)C[C@@H]1N=C(c2ccc(C#N)cc2)c2c(sc(C)c2C#N)-n2c(C)nnc21]
In certain embodiments, the compound of Formula (II) is a compound listed in Table 2.
TABLE 2
Exemplary compounds of Formula (II)
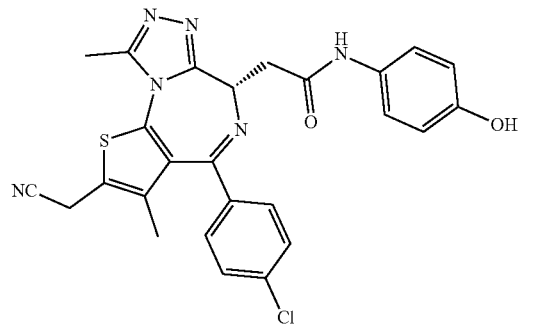 [SMILES: Cc1c(CC#N)sc2c1C(c1ccc(Cl)cc1)=N[C@@H](CC(=O)Nc1ccc(O)cc1)c1nnc(C)n1-2]
201
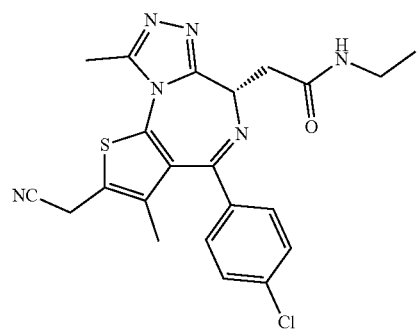 [SMILES: CCNC(=O)C[C@@H]1N=C(c2ccc(Cl)cc2)c2c(sc(CC#N)c2C)-n2c(C)nnc21]
202
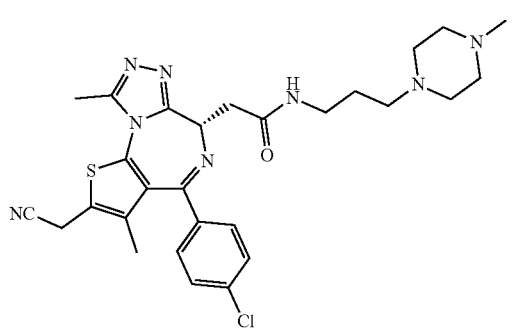 [SMILES: Cc1c(CC#N)sc2c1C(c1ccc(Cl)cc1)=N[C@@H](CC(=O)NCCCN1CCN(C)CC1)c1nnc(C)n1-2]
203
TABLE 2-continued
Exemplary compounds of Formula (II)
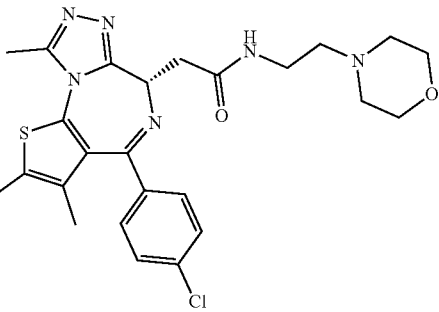
204
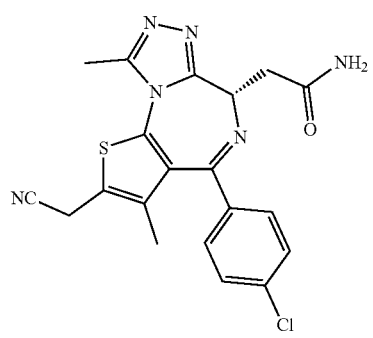 [SMILES: Cc1c(CC#N)sc2c1C(c1ccc(Cl)cc1)=N[C@@H](CC(N)=O)c1nnc(C)n1-2]
205
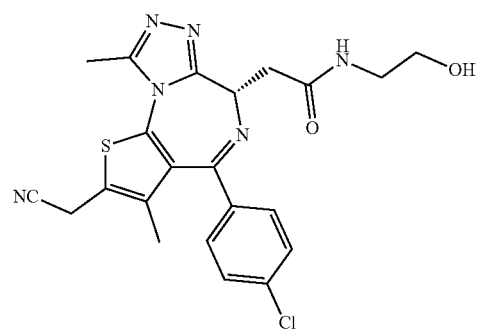 [SMILES: Cc1c(CC#N)sc2c1C(c1ccc(Cl)cc1)=N[C@@H](CC(=O)NCCO)c1nnc(C)n1-2]
206
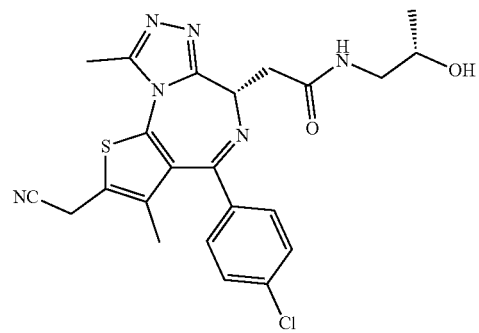 [SMILES: Cc1c(CC#N)sc2c1C(c1ccc(Cl)cc1)=N[C@@H](CC(=O)NC[C@H](C)O)c1nnc(C)n1-2]
207

TABLE 2-continued
Exemplary compounds of Formula (II)
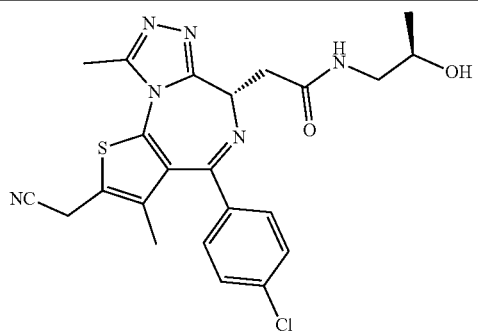
208
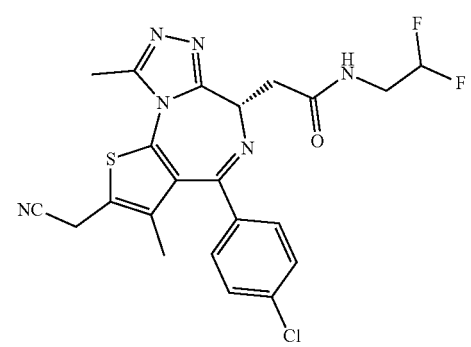 [SMILES: Cc1c(CC#N)sc2c1C(c1ccc(Cl)cc1)=N[C@@H](CC(=O)NCC(F)F)c1nnc(C)n1-2]
209
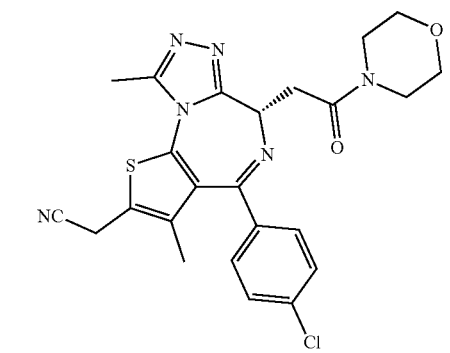 [SMILES: Cc1c(CC#N)sc2c1C(c1ccc(Cl)cc1)=N[C@@H](CC(=O)N1CCOCC1)c1nnc(C)n1-2]
210
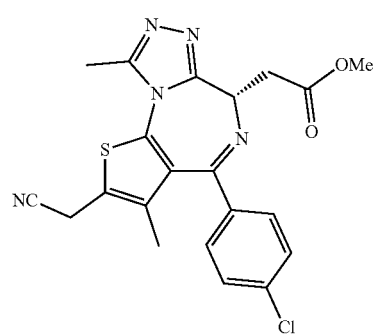 [SMILES: COC(=O)C[C@@H]1N=C(c2ccc(Cl)cc2)c2c(sc(CC#N)c2C)-n2c(C)nnc21]
200
TABLE 2-continued
Exemplary compounds of Formula (II)
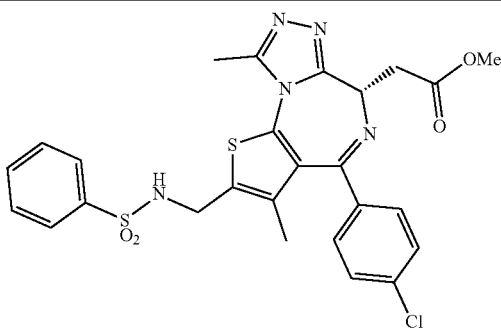
300
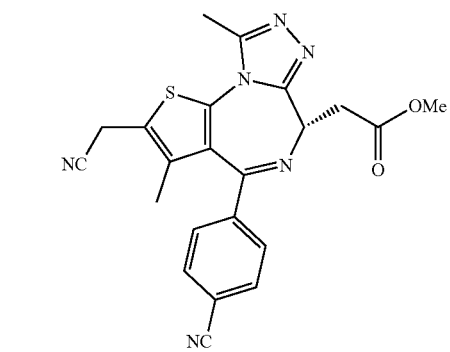 [SMILES: COC(=O)C[C@@H]1N=C(c2ccc(C#N)cc2)c2c(sc(CC#N)c2C)-n2c(C)nnc21]
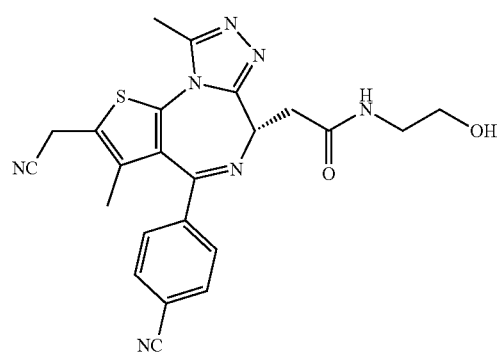 [SMILES: Cc1c(CC#N)sc2c1C(c1ccc(C#N)cc1)=N[C@@H](CC(=O)NCCO)c1nnc(C)n1-2]
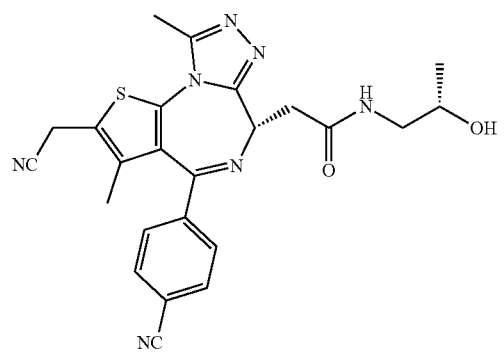 [SMILES: Cc1c(CC#N)sc2c1C(c1ccc(C#N)cc1)=N[C@@H](CC(=O)NC[C@H](C)O)c1nnc(C)n1-2]

TABLE 2-continued
Exemplary compounds of Formula (II)
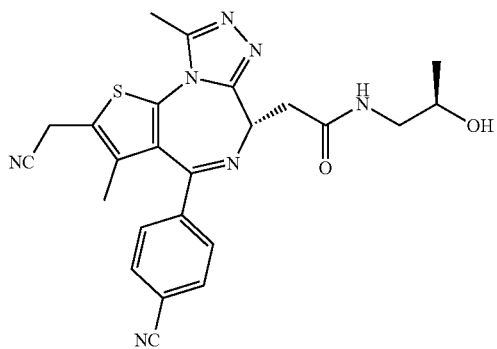 [SMILES: Cc1c(CC#N)sc2c1C(c1ccc(C#N)cc1)=N[C@@H](CC(=O)NC[C@@H](C)O)c1nnc(C)n1-2]
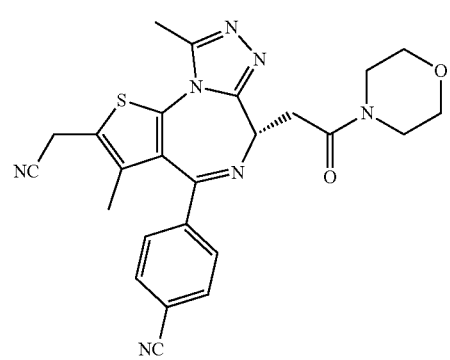 [SMILES: Cc1c(CC#N)sc2c1C(c1ccc(C#N)cc1)=N[C@@H](CC(=O)N1CCOCC1)c1nnc(C)n1-2]
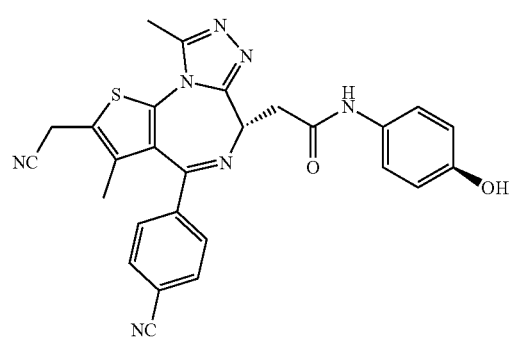
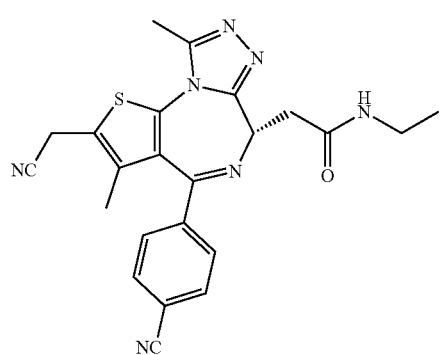 [SMILES: CCNC(=O)C[C@@H]1N=C(c2ccc(C#N)cc2)c2c(sc(CC#N)c2C)-n2c(C)nnc21]
TABLE 2-continued
Exemplary compounds of Formula (II)
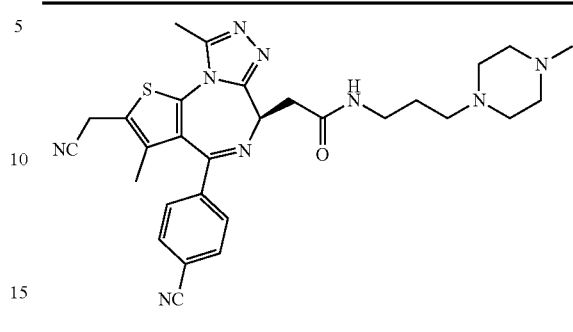
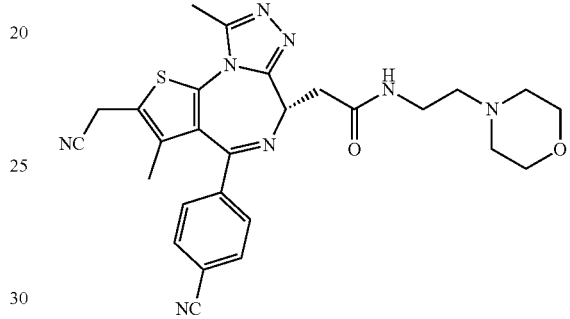
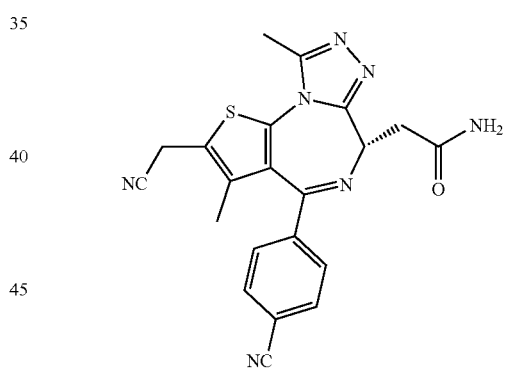
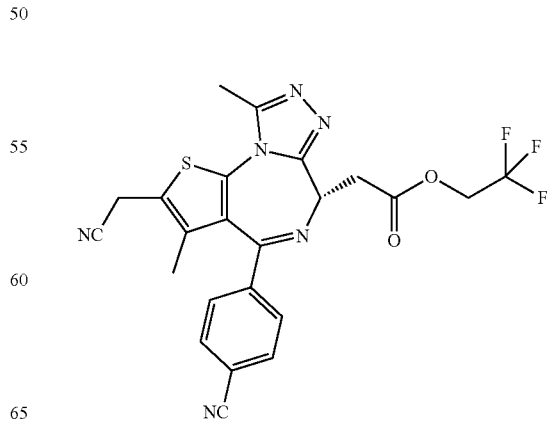

TABLE 2-continued

Exemplary compounds of Formula (II)

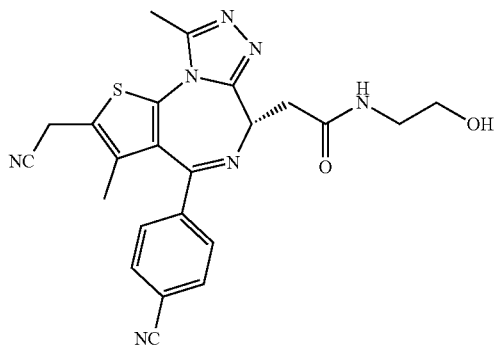 [SMILES: Cc1c(CC#N)sc2c1C(c1ccc(C#N)cc1)=N[C@@H](CC(=O)NCCO)c1nnc(C)n1-2]

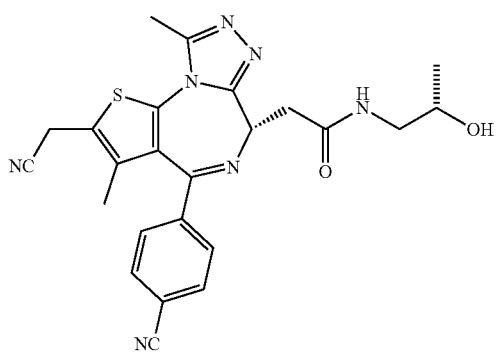 [SMILES: Cc1c(CC#N)sc2c1C(c1ccc(C#N)cc1)=N[C@@H](CC(=O)NC[C@H](C)O)c1nnc(C)n1-2]

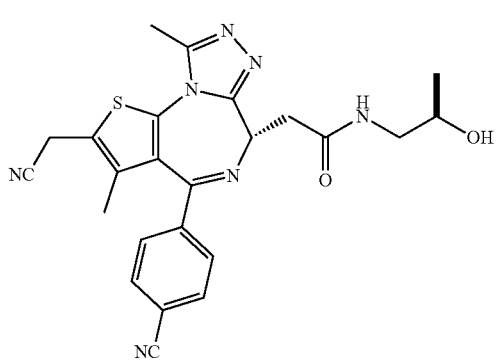 [SMILES: Cc1c(CC#N)sc2c1C(c1ccc(C#N)cc1)=N[C@@H](CC(=O)NC[C@@H](C)O)c1nnc(C)n1-2]

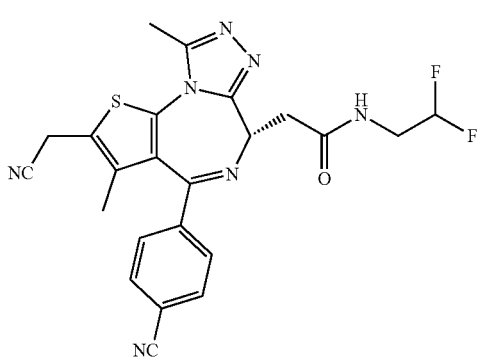 [SMILES: Cc1c(CC#N)sc2c1C(c1ccc(C#N)cc1)=N[C@@H](CC(=O)NCC(F)F)c1nnc(C)n1-2]

In certain embodiments, the compound of Formula (I) is a compound of Formula (I-A-1):

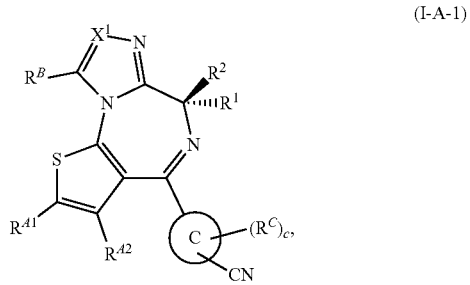

(I-A-1)

or a pharmaceutically acceptable salt, stereoisomer, tautomer, solvate, hydrate, polymorph, co-crystal, or prodrug thereof.

In certain embodiments, the compound of Formula (I) is a compound of Formula (I-A-2):

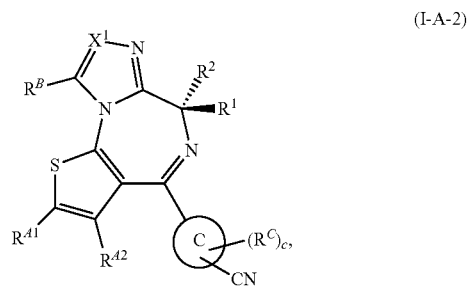

(I-A-2)

or a pharmaceutically acceptable salt, stereoisomer, tautomer, solvate, hydrate, polymorph, co-crystal, or prodrug thereof.

In certain embodiments, the compound of Formula (I) is a compound of Formula (I-B-1):

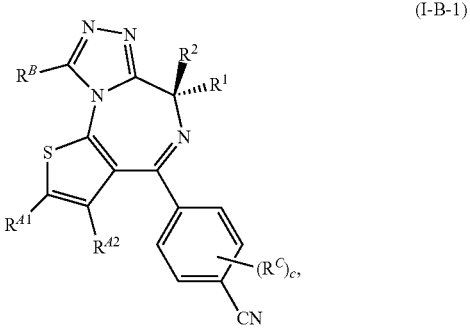

(I-B-1)

or a pharmaceutically acceptable salt, stereoisomer, tautomer, solvate, hydrate, polymorph, co-crystal, or prodrug thereof.

In certain embodiments, the compound of Formula (I) is a compound of Formula (I-B-2):

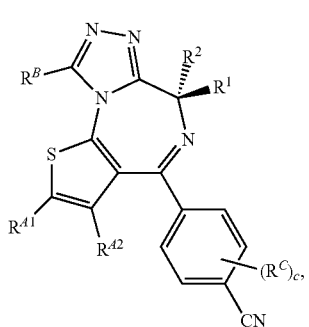

(I-B-2)

or a pharmaceutically acceptable salt, stereoisomer, tautomer, solvate, hydrate, polymorph, co-crystal, or prodrug thereof.

In certain embodiments, the compound of Formula (I) is a compound of Formula (I-B-3):

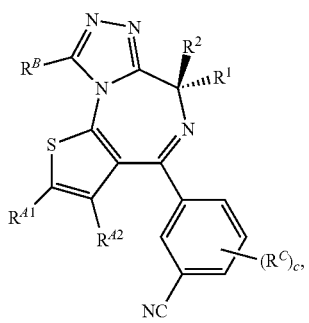

(I-B-3)

or a pharmaceutically acceptable salt, stereoisomer, tautomer, solvate, hydrate, polymorph, co-crystal, or prodrug thereof.

In certain embodiments, the compound of Formula (I) is a compound of Formula (I-B-4):

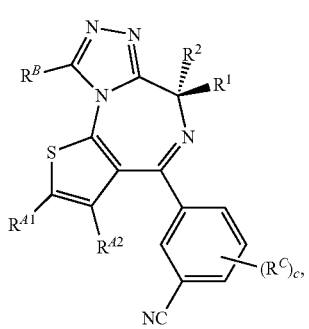

(I-B-4)

or a pharmaceutically acceptable salt, stereoisomer, tautomer, solvate, hydrate, polymorph, co-crystal, or prodrug thereof.

In certain embodiments, the compound of Formula (I) is a compound of Formula (I-B-5):

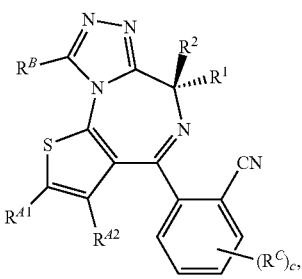

(I-B-5)

or a pharmaceutically acceptable salt, stereoisomer, tautomer, solvate, hydrate, polymorph, co-crystal, or prodrug thereof.

In certain embodiments, the compound of Formula (I) is a compound of Formula (I-B-6):

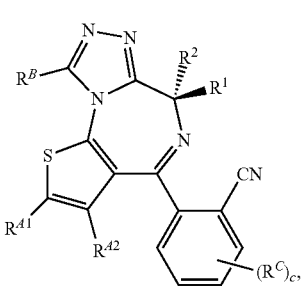

(I-B-6)

or a pharmaceutically acceptable salt, stereoisomer, tautomer, solvate, hydrate, polymorph; co-crystal, or prodrug thereof.

In certain embodiments, the compound of Formula (I) is a compound of Formula (I-C-1):

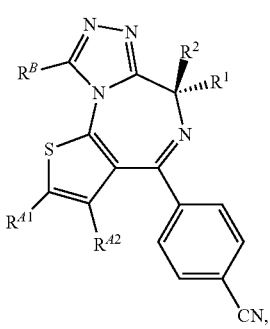

(I-C-1)

or a pharmaceutically acceptable salt, stereoisomer, tautomer, solvate, hydrate, polymorph, co-crystal, or prodrug thereof.

In certain embodiments, the compound of Formula (I) is a compound of Formula (I-C-2):

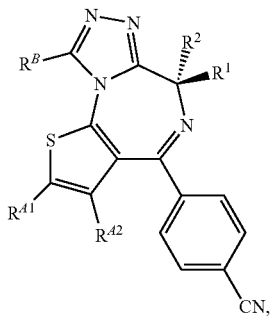
(I-C-2)

or a pharmaceutically acceptable salt, stereoisomer, tautomer, solvate, hydrate, polymorph, co-crystal, or prodrug thereof.

In certain embodiments, the compound of Formula (I) is a compound of Formula (I-C-3):

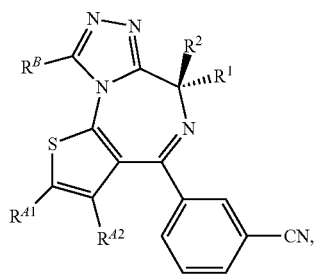
(I-C-3)

or a pharmaceutically acceptable salt, stereoisomer, tautomer, solvate, hydrate, polymorph, co-crystal, or prodrug thereof.

In certain embodiments, the compound of Formula (I) is a compound of Formula (I-C-3):

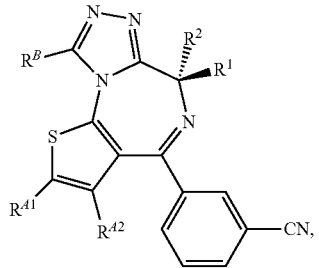
(I-C-3)

or a pharmaceutically acceptable salt, stereoisomer, tautomer, solvate, hydrate, polymorph, co-crystal, or prodrug thereof.

In certain embodiments, the compound of Formula (I) is a compound of Formula (I-C-5):

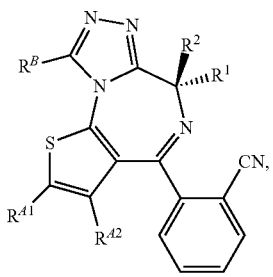
(I-C-5)

or a pharmaceutically acceptable salt, stereoisomer, tautomer, solvate, hydrate, polymorph, co-crystal, or prodrug thereof.

In certain embodiments, the compound of Formula (I) is a compound of Formula (I-C-6):

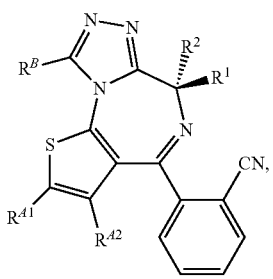
(I-C-6)

or a pharmaceutically acceptable salt, stereoisomer, tautomer, solvate, hydrate, polymorph, co-crystal, or prodrug thereof.

In certain embodiments, the compound of Formula (I) is a compound of Formula (I-D-1):

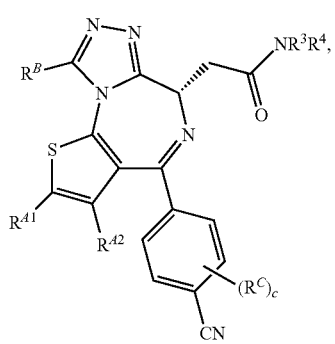
(I-D-1)

or a pharmaceutically acceptable salt, stereoisomer, tautomer, solvate, hydrate, polymorph, co-crystal, or prodrug thereof.

In certain embodiments, the compound of Formula (I) is a compound of Formula (I-D-2):

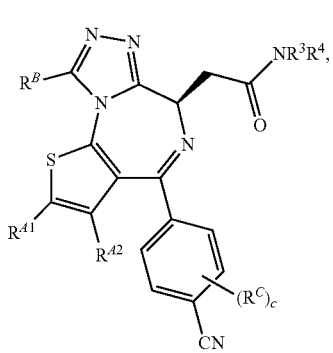

(I-D-2)

or a pharmaceutically acceptable salt, stereoisomer, tautomer, solvate, hydrate, polymorph, co-crystal, or prodrug thereof.

In certain embodiments, the compound of Formula (I) is a compound of Formula (I-D-3):

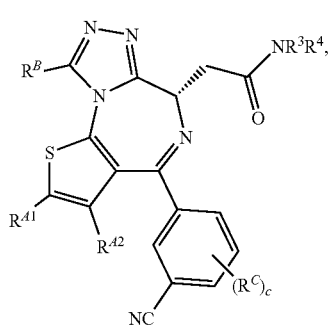

(I-D-3)

or a pharmaceutically acceptable salt, stereoisomer, tautomer, solvate, hydrate, polymorph, co-crystal, or prodrug thereof.

In certain embodiments, the compound of Formula (I) is a compound of Formula (I-D-4):

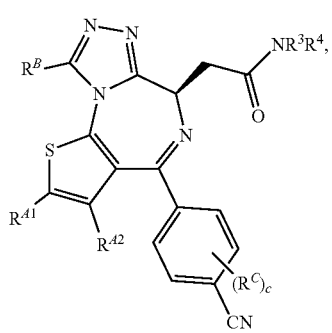

(I-D-4)

or a pharmaceutically acceptable salt, stereoisomer, tautomer, solvate, hydrate, polymorph, co-crystal, or prodrug thereof.

In certain embodiments, the compound of Formula (I) is a compound of Formula (I-D-5):

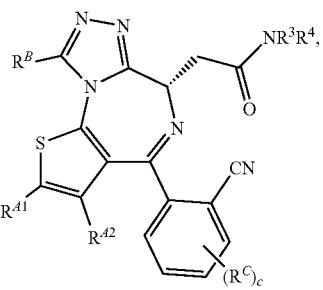

(I-D-5)

or a pharmaceutically acceptable salt, stereoisomer, tautomer, solvate, hydrate, polymorph, co-crystal, or prodrug thereof.

In certain embodiments, the compound of Formula (I) is a compound of Formula (I-D-6):

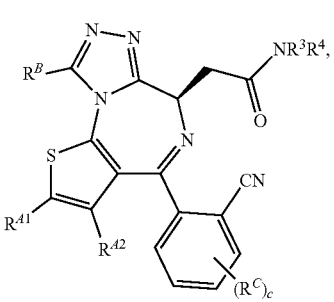

(I-D-6)

or a pharmaceutically acceptable salt, stereoisomer, tautomer, solvate, hydrate, polymorph, co-crystal, or prodrug thereof.

In certain embodiments, the compound of Formula (I) is a compound of Formula (I-E-1):

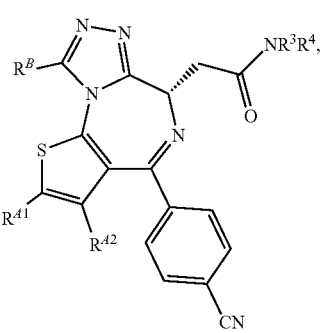

(I-E-1)

or a pharmaceutically acceptable salt, stereoisomer, tautomer, solvate, hydrate, polymorph, co-crystal, or prodrug thereof.

In certain embodiments, the compound of Formula (I) is a compound of Formula (I-E-2):

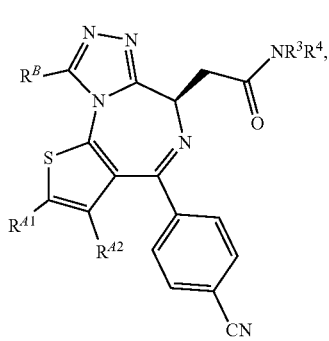

(I-E-2)

or a pharmaceutically acceptable salt, stereoisomer, tautomer, solvate, hydrate, polymorph, co-crystal, or prodrug thereof.

In certain embodiments, the compound of Formula (I) is a compound of Formula (I-E-3):

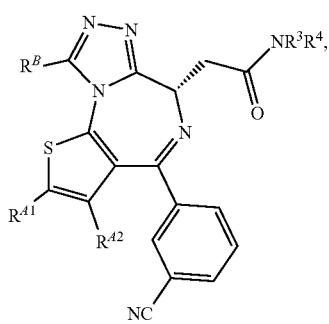

(I-E-3)

or a pharmaceutically acceptable salt, stereoisomer, tautomer, solvate, hydrate, polymorph, co-crystal, or prodrug thereof.

In certain embodiments, the compound of Formula (I) is a compound of Formula (I-E-4):

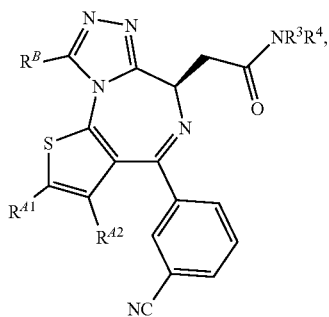

(I-E-4)

or a pharmaceutically acceptable salt, stereoisomer, tautomer, solvate, hydrate, polymorph, co-crystal, or prodrug thereof.

In certain embodiments, the compound of Formula (I) is a compound of Formula (I-E-5):

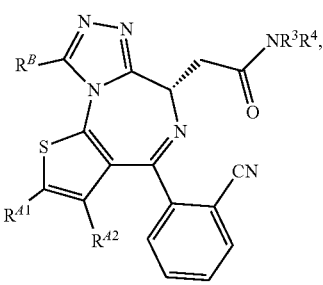

(I-E-5)

or a pharmaceutically acceptable salt, stereoisomer, tautomer, solvate, hydrate, polymorph, co-crystal, or prodrug thereof.

In certain embodiments, the compound of Formula (I) is a compound of Formula (I-E-6):

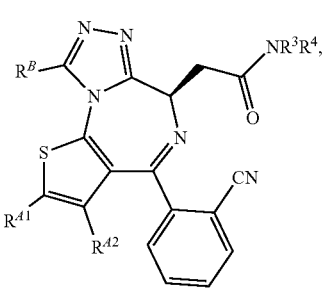

(I-E-6)

or a pharmaceutically acceptable salt, stereoisomer, tautomer, solvate, hydrate, polymorph, co-crystal, or prodrug thereof.

In certain embodiments, the compound of Formula (I) is a compound of Formula (I-F-1):

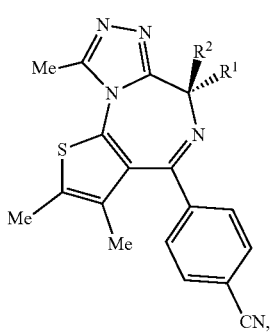

(I-F-1)

or a pharmaceutically acceptable salt, stereoisomer, tautomer, solvate, hydrate, polymorph, co-crystal, or prodrug thereof.

In certain embodiments, the compound of Formula (I) is a compound of Formula (I-F-2):

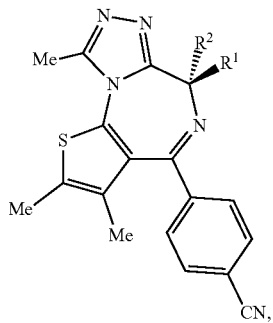

(I-F-2)

or a pharmaceutically acceptable salt, stereoisomer, tautomer, solvate, hydrate, polymorph, co-crystal, or prodrug thereof.

In certain embodiments, the compound of Formula (I) is a compound of Formula (I-F-3):

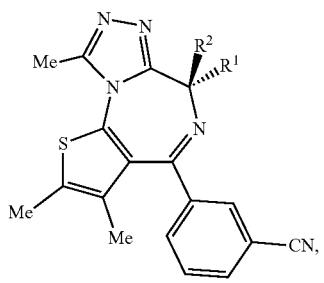

(I-F-3)

or a pharmaceutically acceptable salt, stereoisomer, tautomer, solvate, hydrate, polymorph, co-crystal, or prodrug thereof.

In certain embodiments, the compound of Formula (I) is a compound of Formula (I-F-3):

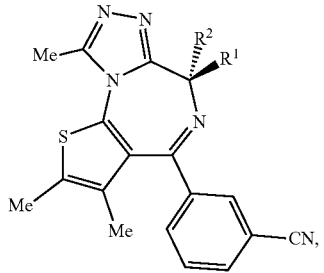

(I-F-3)

or a pharmaceutically acceptable salt, stereoisomer, tautomer, solvate, hydrate, polymorph, co-crystal, or prodrug thereof.

In certain embodiments, the compound of Formula (I) is a compound of Formula (I-F-5):

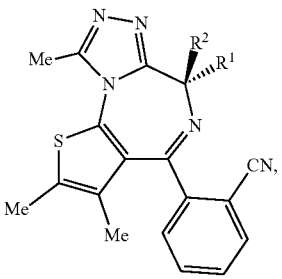

(I-F-5)

or a pharmaceutically acceptable salt, stereoisomer, tautomer, solvate, hydrate, polymorph, co-crystal, or prodrug thereof.

In certain embodiments, the compound of Formula (I) is a compound of Formula (I-F-6):

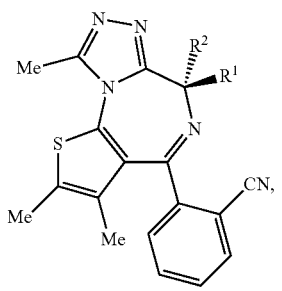

(I-F-6)

or a pharmaceutically acceptable salt, stereoisomer, tautomer, solvate, hydrate, polymorph, co-crystal, or prodrug thereof.

In certain embodiments, the compound of Formula (I) is a compound of Formula (I-G-1):

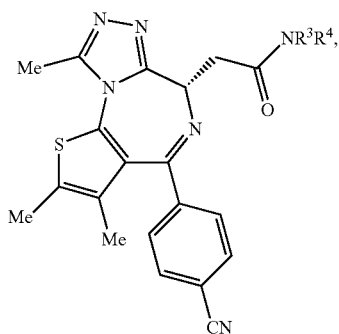

(I-G-1)

or a pharmaceutically acceptable salt, stereoisomer, tautomer, solvate, hydrate, polymorph, co-crystal, or prodrug thereof.

In certain embodiments, the compound of Formula (I) is a compound of Formula (I-G-2):

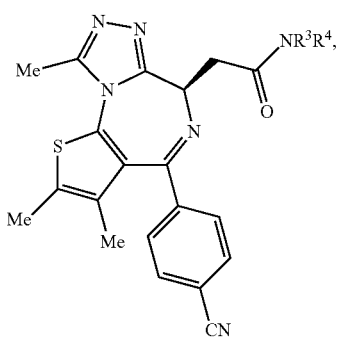

(I-G-2)

or a pharmaceutically acceptable salt, stereoisomer, tautomer, solvate, hydrate, polymorph, co-crystal, or prodrug thereof.

In certain embodiments, the compound of Formula (I) is a compound of Formula (I-G-3):

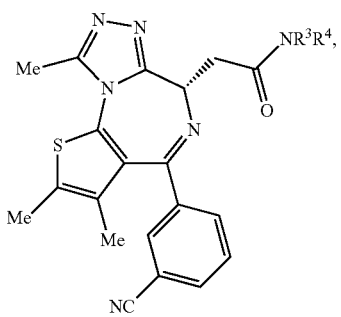

(I-G-3)

or a pharmaceutically acceptable salt, stereoisomer, tautomer, solvate, hydrate, polymorph, co-crystal, or prodrug thereof.

In certain embodiments, the compound of Formula (I) is a compound of Formula (I-G-4):

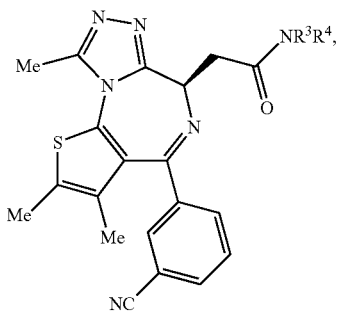

(I-G-4)

or a pharmaceutically acceptable salt, stereoisomer, tautomer, solvate, hydrate, polymorph, co-crystal, or prodrug thereof.

In certain embodiments, the compound of Formula (I) is a compound of Formula (I-G-5):

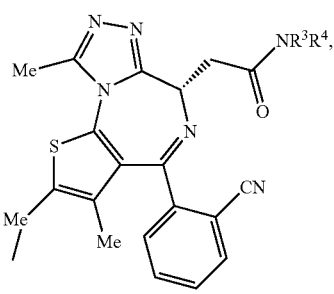

(I-G-5)

or a pharmaceutically acceptable salt, stereoisomer, tautomer, solvate, hydrate, polymorph, co-crystal, or prodrug thereof.

In certain embodiments, the compound of Formula (I) is a compound of Formula (I-G-6):

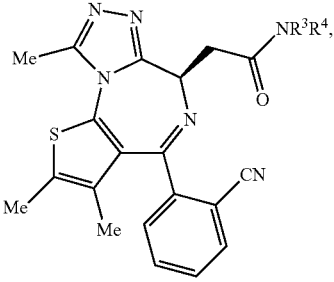

(I-G-6)

or a pharmaceutically acceptable salt, stereoisomer, tautomer, solvate, hydrate, polymorph, co-crystal, or prodrug thereof.

In certain embodiments, the compound of Formula (II) is a compound of Formula (II-A-1):

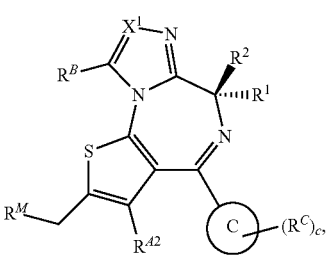

(II-A-1)

or a pharmaceutically acceptable salt, stereoisomer, tautomer, solvate, hydrate, polymorph, co-crystal, or prodrug thereof.

In certain embodiments, the compound of Formula (II) is a compound of Formula (II-A-2):

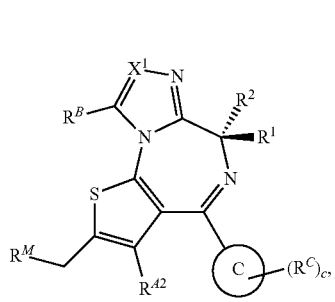

(II-A-2)

or a pharmaceutically acceptable salt, stereoisomer, tautomer, solvate, hydrate, polymorph, co-crystal, or prodrug thereof.

In certain embodiments, the compound of Formula (II) is a compound of Formula (II-B-1):

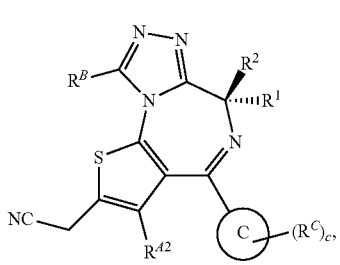

(II-B-1)

or a pharmaceutically acceptable salt, stereoisomer, tautomer, solvate, hydrate, polymorph, co-crystal, or prodrug thereof.

In certain embodiments, the compound of Formula (II) is a compound of Formula (II-B-2):

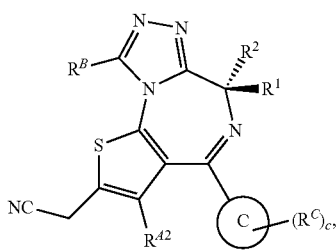

(II-B-2)

or a pharmaceutically acceptable salt, stereoisomer, tautomer, solvate, hydrate, polymorph, co-crystal, or prodrug thereof.

In certain embodiments, the compound of Formula (II) is a compound of Formula (II-C-1):

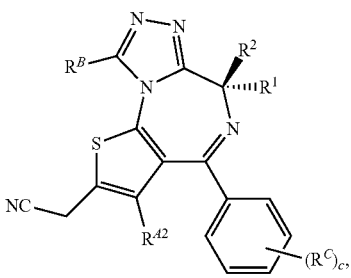

(II-C-1)

or a pharmaceutically acceptable salt, stereoisomer, tautomer, solvate, hydrate, polymorph, co-crystal, or prodrug thereof.

In certain embodiments, the compound of Formula (II) is a compound of Formula (II-C-2):

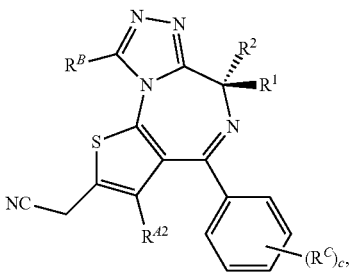

(II-C-2)

or a pharmaceutically acceptable salt, stereoisomer, tautomer, solvate, hydrate, polymorph, co-crystal, or prodrug thereof.

In certain embodiments, the compound of Formula (II) is a compound of Formula (II-D-1):

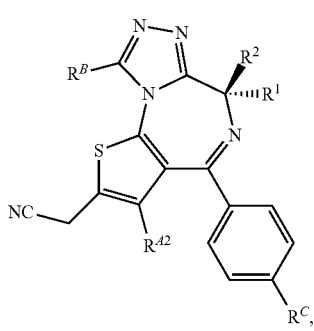

(II-D-1)

or a pharmaceutically acceptable salt, stereoisomer, tautomer, solvate, hydrate, polymorph, co-crystal, or prodrug thereof.

In certain embodiments, the compound of Formula (II) is a compound of Formula (II-D-2):

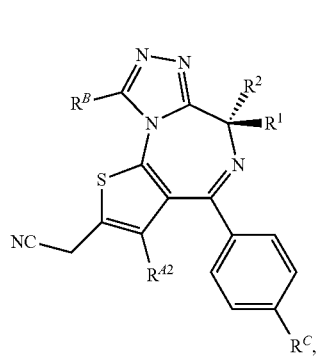

(II-D-2)

or a pharmaceutically acceptable salt, stereoisomer, tautomer, solvate, hydrate, polymorph, co-crystal, or prodrug thereof.

In certain embodiments, the compound of Formula (II) is a compound of Formula (II-E-1):

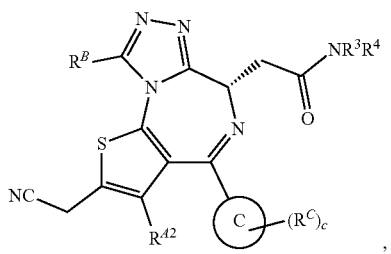

(II-E-1)

or a pharmaceutically acceptable salt, stereoisomer, tautomer, solvate, hydrate, polymorph, co-crystal, or prodrug thereof.

In certain embodiments, the compound of Formula (II) is a compound of Formula (II-E-2):

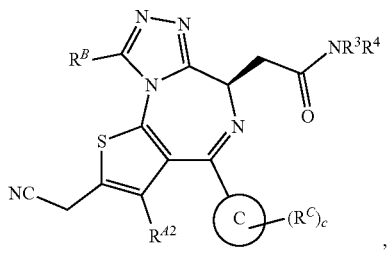

(II-E-2)

or a pharmaceutically acceptable salt, stereoisomer, tautomer, solvate, hydrate, polymorph, co-crystal, or prodrug thereof.

In certain embodiments, the compound of Formula (II) is a compound of Formula (II-F-1):

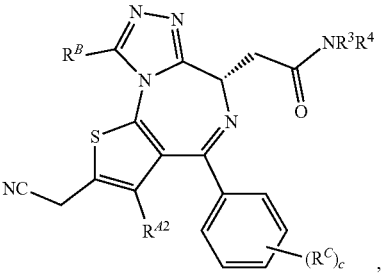

(II-F-1)

or a pharmaceutically acceptable salt, stereoisomer, tautomer, solvate, hydrate, polymorph, co-crystal, or prodrug thereof.

In certain embodiments, the compound of Formula (II) is a compound of Formula (II-F-2):

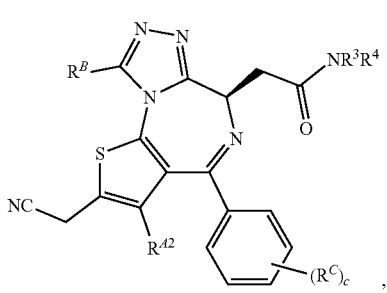

(II-F-2)

or a pharmaceutically acceptable salt, stereoisomer, tautomer, solvate, hydrate, polymorph, co-crystal, or prodrug thereof.

In certain embodiments, the compound of Formula (II) is a compound of Formula (II-G-1):

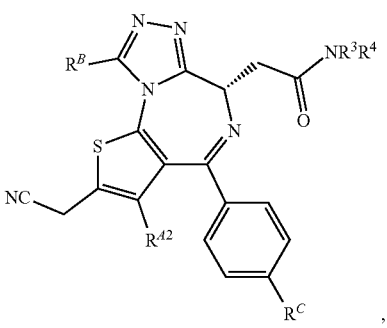

(II-G-1)

or a pharmaceutically acceptable-salt, stereoisomer, tautomer, solvate, hydrate, polymorph, co-crystal, or prodrug thereof.

In certain embodiments, the compound of Formula (II) is a compound of Formula (II-G-2):

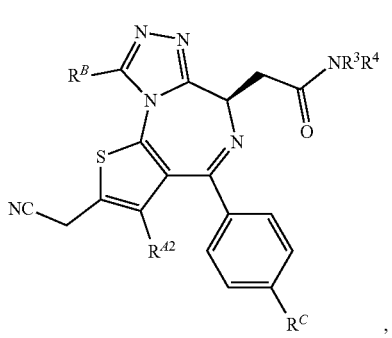

(II-G-2)

or a pharmaceutically acceptable salt, stereoisomer, tautomer, solvate, hydrate, polymorph, co-crystal, or prodrug thereof.

In certain embodiments, the compound of Formula (II) is a compound of Formula (II-H-1):

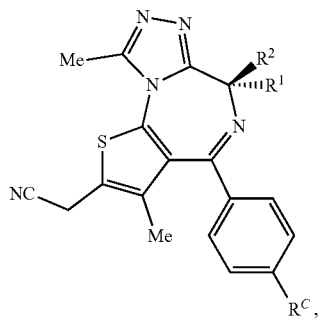

(II-H-1)

or a pharmaceutically acceptable salt, stereoisomer, tautomer, solvate, hydrate, polymorph, co-crystal, or prodrug thereof.

In certain embodiments, the compound of Formula (II) is a compound of Formula (II-H-2):

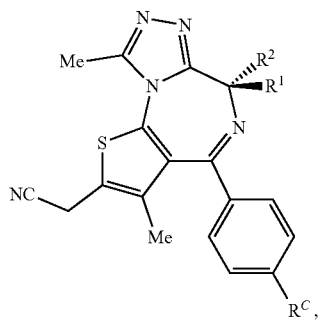

(II-H-2)

or a pharmaceutically acceptable salt, stereoisomer, tautomer, solvate, hydrate, polymorph, co-crystal, or prodrug thereof.

In certain embodiments, the compound of Formula (II) is a compound of Formula (II-J-1):

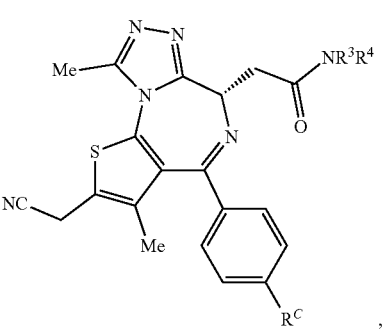

(II-J-1)

or a pharmaceutically acceptable salt, stereoisomer, tautomer, solvate, hydrate, polymorph, co-crystal, or prodrug thereof.

In certain embodiments, the compound of Formula (II) is a compound of Formula (II-J-2):

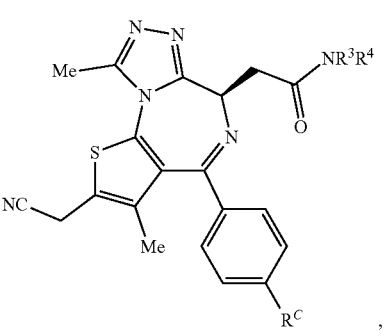

(II-J-2)

or a pharmaceutically acceptable salt, stereoisomer, tautomer, solvate, hydrate, polymorph, co-crystal, or prodrug thereof.

In certain embodiments, a compound of Formula (I) or (II) has improved metabolic stability relative to a known bromodomain inhibitor (e.g., JQ1). In certain embodiments, a compound of Formula (I) or (II) has decreased lipophilicity relative to a known bromodomain inhibitor (e.g., JQ1). In certain embodiments, a compound of Formula (1) or (II) has improved pharmacokinetic parameters relative to a known bromodomain inhibitor (e.g., JQ1). In some embodiments, the compound has a higher clearance. In some embodiments, the compound has a lower clearance. In some embodiments, the compound has a higher volume distribution (e.g., steady-state volume distribution). In some embodiments, the compound has a lower volume distribution (e.g., steady-state volume distribution). In some embodiments, the compound has a longer half-life (e.g., terminal $t_{1/2}$). In some embodiments, the compound has a lower half-life (e.g., terminal $t_{1/2}$). In some embodiments, the compound has a higher integral area under the concentration-time curve (e.g., $AUC_{last}$, $AUC_{0-\infty}$). In some embodiments, the compound has a lower integral area under the concentration-time curve (e.g., $AUC_{last}$, $AUC_{0-\infty}$). In some embodiments, the compound has a higher time to maximum concentration. In some embodiments, the compound has a lower time to maximum concentration. In some embodiments, the compound has a higher maximum concentration (e.g., maximum plasma concentration). In some embodiments, the compound has a lower maximum concentration (e.g., maximum plasma concentration). In some embodiments, the compound has a higher bioavailability. In some embodiments, the compound has a lower bioavailability.

Pharmaceutical-Compositions and Administration

The present disclosure provides pharmaceutical compositions comprising a compound described herein (e.g., a compound of Formula (I) or (II)), or a pharmaceutically acceptable salt, solvate, hydrate, polymorph, co-crystal, tautomer, stereoisomer, isotopically labeled derivative, or prodrug thereof), and optionally a pharmaceutically acceptable excipient. In certain embodiments, the pharmaceutical composition described herein comprises a compound of Formula (I) or (II), or a pharmaceutically acceptable salt thereof, and optionally a pharmaceutically acceptable excipient. In certain embodiments, the pharmaceutical composition described herein comprises a compound of Formula (I) or (II), or a pharmaceutically acceptable salt thereof, and a pharmaceutically acceptable excipient.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating and/or preventing a disease (e.g., a disease described herein) in a subject in need thereof. In certain embodiments, the effective amount is an amount effective for treating a disease in a subject in need thereof. In certain embodiments, the effective amount is an amount effective for preventing a disease in a subject in need thereof. In certain embodiments, the effective amount is an amount effective for reducing the risk of developing a disease in a subject in need thereof. In certain embodiments, the effective amount is an amount effective for male contraception (e.g., effective for inhibiting sperm formation) in a subject in need thereof. In certain embodiments, the effective amount is an amount effective for inhibiting the replication of a virus. In certain embodiments, the effective amount is an amount effective for killing a virus. In certain embodiments, the effective amount is an amount effective for inhibiting the activity (e.g., aberrant activity, such as increased activity) of a bromodomain-containing protein in a subject or cell. In certain embodiments, the effective amount is an amount effective for inhibiting the activity (e.g., aberrant activity, such as increased activity) of a bromodomain in a subject or cell. In certain embodiments, the effective amount is an amount effective for inhibiting the binding of a bromodomain of a bromodomain-containing protein to an acetyl-lysine residue of a second protein (e.g., a histone) in a subject or cell. In certain embodiments, the effective amount is an amount effective for modulating (e.g., inhibiting) transcriptional elongation in a subject or cell. In certain embodiments, the effective amount is an amount effective for modulating (e.g., down-regulating or inhibiting) the expression (e.g., transcription) of a gene that is regulated by a bromodomain-containing protein in a subject or cell. In certain embodiments, the effective amount is an amount effective for inducing apoptosis of a cell. In certain embodiments, the effective amount is an amount effective for inducing apoptosis in a subject. In certain embodiments, the effective amount is an amount effective for inducing G1 arrest in a subject or cell. An effective amount of a compound may vary from about 0.001 mg/kg to about 1000 mg/kg in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In certain embodiments, the effective amount is an amount effective for inhibiting the activity of a bromodomain-containing protein, the activity of a bromodomain, the binding of a bromodomain of a bromodomain-containing protein to an acetyl-lysine residue of a second protein (e.g., a histone), the transcriptional elongation, and/or the expression (e.g., transcription) of a gene that is regulated by a bromodomain-containing protein, for inducing or increasing apoptosis, or for inducing or increasing G1 arrest by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting the activity of a bromodomain-containing protein, the binding of a bromodomain of a bromodomain-containing protein to an acetyl-lysine residue of a second protein (e.g., a histone), and/or the expression (e.g., transcription) of a gene that is regulated by a bromodomain-containing protein by at most about 90%, at most about 80%, at most about 70%, at most about 60%, at most about 50%, at most about 40%, at most about 30%, at most about 20%, or at most about 10%. Combinations of the ranges described herein (e.g., at least about 20% and at most about 50%) are also within the scope of the disclosure. In certain embodiments, the activity of a bromodomain-containing protein, the binding of a bromodomain of a bromodomain-containing protein to an acetyl-lysine residue of a second protein (e.g., a histone), and/or the expression (e.g., transcription) of a gene that is regulated by a bromodomain-containing protein are inhibited by a percentage or a range of percentage described herein by an effective amount of a compound described herein.

In certain embodiments, the gene regulated by a bromodomain-containing protein is a gene regulated by a bromo and extra terminal protein (BET). In certain embodiments, the gene regulated by a bromodomain-containing protein is BRD2. In certain embodiments, the gene regulated by a bromodomain-containing protein is BRD2(1). In certain embodiments, the gene regulated by a bromodomain-containing protein is BRD2(2). In certain embodiments, the gene regulated by a bromodomain-containing protein is BRD3. In certain embodiments, the gene regulated by a bromodomain-containing protein is BRD3(1). In certain embodiments, the gene regulated by a bromodomain-containing protein is BRD3(2). In certain embodiments, the gene regulated by a bromodomain-containing protein is BRD4. In certain embodiments, the gene regulated by a bromodomain-containing protein is BRD4(1). In certain embodiments, the gene regulated by a bromodomain-containing protein is BRD4(2). In certain embodiments, the gene regulated by a bromodomain-containing protein is BRDT. In certain embodiments, the gene regulated by a bromodomain-containing protein is BRDT(1). In certain embodiments, the gene regulated by a bromodomain-containing protein is BRDT(2). In certain embodiments, the gene regulated by a bromodomain-containing protein is a gene regulated by a TBP (TATA box binding protein)-associated factor protein (TAF). In certain embodiments, the gene regulated by a bromodomain-containing protein is TAF1. In certain embodiments, the gene regulated by a bromodomain-containing protein is TAF1L. In certain embodiments, the gene regulated by a bromodomain-containing protein is a gene regulated by a CREB-binding protein (CBP). In certain embodiments, the gene regulated by a bromodomain-containing protein is a gene regulated by an E1A binding protein p300 (EP300).

Pharmaceutical compositions described herein can be prepared by any method known in the art of pharmacology. In general, such preparatory methods include the steps of bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij© 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol; glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behenate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, be in the form of eye drops including, for example, a 0.1-a 0.1/1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations). An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is, the lifetime of the subject, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds described herein may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic and/or prophylactic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk of developing a disease in a subject in need thereof, in inhibiting the replication of a virus, in killing a virus, in inhibiting the activity of a bromodomain-containing protein in a subject or cell, in inhibiting the activity of a bromodomain in a subject or cell, in inhibiting the binding of a bromodomain of a bromodomain-containing protein to an acetyl-lysine residue of a second protein (e.g., a histone) in a subject or cell, in modulating (e.g., inhibiting) the transcription elongation, in modulating (e.g., inhibiting) the expression (e.g., transcription) of a gene that is regulated by a bromodomain-containing protein in a subject or cell, in inducing apoptosis of a cell, in inducing apoptosis in a subject, or in inducing G1 arrest in a subject or cell), bioavailability, and/or safety, reduce drug resistance, reduce and/or modify their metabolism, inhibit their excretion, and/or modify their distribution within the body of a subject. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain, embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) utilized in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-leukemia agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine I 131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), or a combination thereof. In certain embodiments, the additional pharmaceutical agent is an anti-viral agent. In certain embodiments, the additional pharmaceutical agent is a binder of a bromodomain-containing protein. In certain embodiments, the additional pharmaceutical agent is a binder of a bromodomain. In certain embodiments, the additional pharmaceutical agent is a binder or inhibitor of a bromodomain-containing protein. In certain embodiments, the additional pharmaceutical agent is an binder or inhibitor of a bromodomain. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy), viral agent. In certain embodiments, the additional pharmaceutical agent is a binder of a bromodomain-containing protein. In certain embodiments, the additional pharmaceutical agent is a binder of a bromodomain. In certain embodiments, the additional pharmaceutical agent is a binder or inhibitor of a bromodomain-containing protein. In certain embodiments, the additional pharmaceutical agent is an binder or inhibitor of a bromodomain. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, or prodrug thereof, or a pharmaceutical composition thereof. In certain embodiments, the kits are useful for treating and/or preventing a disease described herein in a subject in need thereof. In certain embodiments, the kits are useful for treating a disease described herein in a subject in need thereof. In certain embodiments, the kits are useful for preventing a disease described herein in a subject in need thereof. In certain embodiments, the kits are useful for reducing the risk of developing a disease described herein in a subject in need thereof. In certain embodiments, the kits are useful for male contraception. In certain embodiments, the kits are useful for inhibiting sperm formation. In certain embodiments, the kits are useful for in inhibiting the replication of a virus. In certain embodiments, the kits are useful for killing a virus. In certain embodiments, the kits are useful for inhibiting the activity (e.g., aberrant activity, such as increased activity) of a bromodomain-containing protein in a subject or cell. In certain embodiments, the kits are useful for inhibiting the activity (e.g., aberrant activity, such as increased activity) of a bromodomain in a subject or cell. In certain embodiments, the kits are useful for inhibiting the binding of a bromodomain of a bromodomain-containing protein to an acetyl-lysine residue of a second protein (e.g., a histone) in a subject or cell. In certain embodiments, the kits are useful for modulating (e.g., inhibiting) the transcriptional elongation in a subject or cell. In certain embodiments, the kits are useful for modulating (e.g., down-regulating or inhibiting) the expression (e.g., transcription) of a gene that is regulated by a bromodomain-containing protein in a subject or cell. In certain embodiments, the kits are useful for inducing apoptosis of a cell. In certain embodiments, the kits are useful for inducing apoptosis in a subject. In certain embodiments, the kits, are useful for inducing G1 arrest in a subject or cell.

In certain embodiments, the kits are useful for screening a library of compounds to identify a compound that is useful in a method of the disclosure.

In certain embodiments, a kit described herein further includes instructions for using the kit, such as instructions for using the kit in a method of the disclosure (e.g., instructions for administering a compound or pharmaceutical composition described herein to a subject). A kit described herein may also include information as required by a regulatory agency such as the U.S. Food and Drug Administration (FDA). In certain embodiments, the information included in the kits is prescribing information. In certain embodiments, the kits and instructions provide for treating and/or preventing a disease described herein in a subject in need thereof. In certain embodiments, the kits and instructions provide for treating a disease described herein in a subject in need thereof. In certain embodiments, the kits and instructions provide for preventing a disease described herein in a subject in need thereof. In certain embodiments, the kits and instructions provide for reducing the risk of developing a disease described herein in a subject in need thereof. In certain embodiments, the kits and instructions provide for male contraception. In certain embodiments, the kits and instructions provide for inhibiting the replication of a virus. In certain embodiments, the kits and instructions provide for killing a virus. In certain embodiments, the kits and instructions provide for inhibiting the activity (e.g., aberrant activity, such as increased activity) of a bromodomain-containing protein in a subject or cell. In certain embodiments, the kits and instructions provide for inhibiting the activity (e.g., aberrant activity, such as increased activity) of a bromodomain in a subject or cell. In certain embodiments, the kits and instructions provide for inhibiting the binding of a bromodomain of a bromodomain-containing protein to an acetyl-lysine residue of a second protein (e.g., a histone) in a subject or cell. In certain embodiments, the kits and instructions provide for modulating (e.g., inhibiting) the transcriptional elongation. In certain embodiments, the kits and instructions provide for modulating (e.g., down-regulating or inhibiting) the expression (e.g., transcription) of a gene that is regulated by a bromodomain-containing protein in a subject or cell. In certain embodiments, the kits and instructions provide for inducing apoptosis of an in vitro cell. In certain embodiments, the kits and instructions provide for inducing apoptosis of a cell in a subject. In certain embodiments, the kits and instructions provide for inducing G1 arrest in a subject or cell. In certain embodiments, the kits and instructions provide for screening a library of compounds to identify a compound that is useful in a method of the disclosure. A kit described herein may include one or more additional pharmaceutical agents described herein as a separate composition.

Methods of Treatment and Uses

The present disclosure provides methods for the treatment of a wide range of diseases, such as diseases associated with bromodomains, diseases associated with the activity (e.g., aberrant activity) of bromodomains, diseases associated with bromodomain-containing proteins, and disease associated with the activity (e.g., aberrant activity) of bromodomain-containing proteins. Exemplary diseases include, but are not limited to, proliferative diseases, cardiovascular diseases, viral infections, fibrotic diseases, neurological diseases, metabolic diseases, endocrine diseases, and radiation poisoning. Also provided by the present disclosure are methods for male contraception. The present disclosure also provides methods of inhibiting sperm formation. The present disclosure further provides methods of inhibiting the activity (e.g., aberrant activity, such as increased activity) of a bromodomain or bromodomain-containing protein, methods of inhibiting the binding of a bromodomain of a bromodomain-containing protein to an acetyl-lysine residue of a second protein (e.g., a histone), methods of modulating (e.g., inhibiting) the transcriptional elongation, methods of modulating (e.g., down-regulating or inhibiting) the expression (e.g., transcription) of a gene that is regulated by a bromodomain-containing protein, methods of inducing apoptosis, and methods of inducing G1 arrest.

Gene regulation is fundamentally governed by reversible, non-covalent assembly of macromolecules. Signal transduction to RNA polymerase requires higher-ordered protein complexes, spatially regulated by assembly factors capable of interpreting the post-translational modification states of chromatin. Epigenetic readers are structurally diverse proteins, and each of the epigenetic readers possesses one or more evolutionarily conserved effector modules, which recognize covalent modifications of proteins (e.g., histones) or DNA. The ε-N-acetylation of lysine residues (Kac) on histone tails is associated with an open chromatin architecture and transcriptional activation. Context-specific molecular recognition of acetyl-lysine is principally mediated by bromodomains.

Bromodomain-containing proteins are of substantial biological interest, as components of transcription factor complexes (e.g., TBP (TATA box binding protein)-associated factor 1 (TAF1), CREB-binding protein (CBP or CREBBP), P300/CBP-associated factor (PCAF), and Gen5) and determinants of epigenetic memory. There are 41 human proteins containing a total of 57 diverse bromodomains. Despite large sequence variations, all bromodomains share a conserved fold comprising a left-handed bundle of four alpha helices ($\alpha_Z$, $\alpha_A$, $\alpha_B$, and $\alpha_C$), linked by diverse loop regions (ZA and BC loops) that determine substrate specificity. Co-crystal structures with peptidic substrates showed that the acetyl-lysine is recognized by a central hydrophobic cavity and is anchored by a hydrogen bond with an asparagine residue present in most bromodomains. The bromo and extra-terminal (BET) family (e.g., BRD2, BRD3, BRD4 and BRDT) shares a common domain architecture comprising two N-terminal bromodomains that exhibit a high degree of sequence conservation, and a more divergent C-terminal recruitment domain.

Recent research has established a compelling rationale for targeting BRD4 in cancer. BRD4 functions to facilitate cell cycle progression, and knock-down in cultured cancer cell lines prompts G1 arrest. BRD4 is an important mediator of transcriptional elongation, functioning to recruit the positive transcription elongation factor complex (P-TEFb). Cyclin dependent kinase-9, a core component of P-TEFb, is a validated target in chronic lymphocytic leukemia, and has recently been linked to c-Myc dependent transcription. Bromodomains present in BRD4 recruit P-TEFb to mitotic chromosomes resulting in increased expression of growth promoting genes. BRD4 remains bound to transcriptional start sites of genes expressed during M/G1 but has not been found present at start sites that are expressed later in the cell cycle. Knockdown of BRD4 in proliferating cells has been shown to lead to G1 arrest and apoptosis by decreasing expression levels of genes important for mitotic progression and survival.

Importantly, BRD4 has recently been identified as a component of a recurrent t(15;19) chromosomal translocation in an aggressive form of human squamous cell carcinoma. Such translocations express the tandem N-terminal bromodomains of BRD4 as an in-frame chimera with the nuclear protein in testis (NUT) protein, genetically defining the NUT midline carcinoma (NMC). Functional studies in patient-derived NMC cell lines have validated the essential role of the BRD4-NUT oncoprotein in maintaining the characteristic proliferation advantage and differentiation block of this malignancy. Notably, RNA silencing of BRD4-NUT gene expression arrests proliferation and prompts squamous differentiation with a marked increase in cytokeratin expression. A bromodomain may also down-regulates Myc and other transcriptional factors, such as interleukin 7 receptor (IL7R). These observations underscore the utility and therapeutic potential of a binder or inhibitor of bromodomain-containing proteins.

In another aspect, the present disclosure provides methods of inhibiting the activity of a bromodomain-containing protein in a subject.

In another aspect, the present disclosure provides methods of inhibiting the activity of a bromodomain-containing protein in a biological sample (e.g., a cell).

In certain embodiments, the bromodomain-containing protein is a bromodomain-containing protein described herein (e.g., a BET protein, such as BRD2, BRD3, BRD4, or BRDT). In certain embodiments, the activity of a bromodomain-containing protein in a subject or a biological sample (e.g., a cell) is inhibited by the described methods. In certain embodiments, the activity of a bromodomain-containing protein in a subject or a biological sample (e.g., a cell) is inhibited by the described methods by at least about 1%, at least about 3%, at least about 10%, at least about 20%, at least about 30%, at least about 40%, at least about 50%, at least about 60%, at least about 70%, at least about 80%, at least about 90%, at least about 95%, or at least about 98%. In certain embodiments, the activity of a bromodomain-containing protein in a subject or a biological sample (e.g., a cell) is inhibited by the described methods by at most about 90%, at most about 80%, at most about 70%, at most about 60%, at most about 50%, at most about 40%, at most about 30%, at most about 20%, at most about 10%, at most about 3%, or at most about 1%. Combinations of the above-referenced ranges (e.g., at least about 10% and at most about 50%) are also within the scope of the disclosure. Other ranges are also possible. In some embodiments, the activity of a bromodomain-containing protein in a subject or a biological sample (e.g., a cell) is selectively inhibited by the described methods. In some embodiments, the activity of a bromodomain-containing protein in a subject or a biological sample (e.g., a cell) is selectively inhibited by the described methods, compared to the activity of a kinase (e.g., a MAP kinase, a mitotic spindle kinase, a polo kinase). In other embodiments, the activity of a bromodomain-containing protein in a subject or a biological sample (e.g., a cell) is non-selectively inhibited by the described methods. In certain embodiments, the cytokine level and/or histamine release are reduced by the described methods.

In certain embodiments, the activity of a bromodomain-containing protein is an aberrant activity of the bromodomain-containing protein. In certain embodiments, the activity of a bromodomain-containing protein is an increased activity of the bromodomain-containing protein. In certain embodiments, the activity of a bromodomain-containing protein is reduced by a method of the disclosure.

In certain embodiments, the subject is an animal. The animal may be of either sex and may be at any stage of development. In certain embodiments, the subject is a male. In certain embodiments, the subject is a female. In certain embodiments, the subject described herein is a human. In certain embodiments, the subject described herein is a human male. In certain embodiments, the subject described herein is a human female. In certain embodiments, the subject is a human diagnosed as having a disease described herein. In certain embodiments, the subject is a human diagnosed as being at a higher-than-normal risk of developing a disease described herein. In certain embodiments, the subject is a human suspected of having a disease described herein. In certain embodiments, the subject is a non-human animal. In certain embodiments, the subject is a fish. In certain embodiments, the subject is a mammal. In certain embodiments, the subject is a non-human mammal. In certain embodiments, the subject is a human or non-human mammal. In certain embodiments, the subject is a domesticated animal, such as a dog, cat, cow, pig, horse, sheep, or goat. In certain embodiments, the subject is a companion animal such as a dog or cat. In certain embodiments, the subject is a livestock animal such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs).

In certain embodiments, a cell described herein is in vitro. In certain embodiments, a cell is ex vivo. In certain embodiments, a cell is in vivo.

In another aspect, the present disclosure provides methods of inhibiting the activity of a bromodomain in a subject.

In another aspect, the present disclosure provides methods of inhibiting the activity of a bromodomain in a biological sample (e.g., a cell).

In certain embodiments, the activity of a bromodomain is an aberrant activity of the bromodomain. In certain embodiments, the activity of a bromodomain is an increased activity of the bromodomain. In certain embodiments, the activity of a bromodomain is reduced by a method of the disclosure.

Another aspect of the present disclosure relates to methods of inhibiting the binding of a bromodomain of a bromodomain-containing protein to an acetyl-lysine residue of a second protein (e.g., a histone) in a subject.

Another aspect of the present disclosure relates to methods of inhibiting the binding of a bromodomain of a bromodomain-containing protein to an acetyl-lysine residue of a second protein (e.g., a histone) in a biological sample (e.g., a cell).

In certain embodiments, the second protein is a protein with an acetyl-lysine residue. In certain embodiments, the second protein is not a bromodomain-containing protein. In certain embodiments, the second protein is a histone. In certain embodiments, the histone is selected from the group consisting of H1, H2A, H2B, H3, H4, and H5. In certain embodiments, the binding of a bromodomain of the bromodomain-containing protein to an acetyl-lysine residue of the second protein (e.g., a histone) is inhibited by the described methods.

In another aspect, the present disclosure provides methods of modulating (e.g., inhibiting) the transcription elongation. In certain embodiments, the transcription elongation is modulated (e.g., inhibited) by the described methods.

In another aspect, the present disclosure provides methods of modulating the expression (e.g., transcription) of a gene that is regulated by a bromodomain-containing protein in a subject.

In another aspect, the present disclosure provides methods of modulating the expression (e.g., transcription) of a gene that is regulated by a bromodomain-containing protein in a biological sample (e.g., a cell).

In certain embodiments, the present disclosure provides methods of down-regulating or inhibiting the expression (e.g., transcription) of a gene that is regulated by a bromodomain-containing protein in a subject or biological sample (e.g., a cell). Without wishing to be bound by any particular theory, the compounds and pharmaceutical compositions described herein may be able to interfere with the binding of a bromodomain-containing protein to a transcriptional start site of the gene. In certain embodiments, the compounds and pharmaceutical compositions described herein interfere with the recognition of acetyl-lysine by a bromodomain or bromodomain-containing protein during the expression (e.g., transcription) of the gene. In certain embodiments, the compounds and pharmaceutical compositions described herein interfere with the anchoring of a bromodomain-containing protein to an acetylated chromatin (e.g., a bromodomain of the bromodomain-containing protein being anchored to an acetyl-lysine of the acetylated chromatin) during the expression (e.g., transcription) of the gene. In certain embodiments, the expression (e.g., transcription) of a gene that is regulated by a bromodomain-containing protein in a subject or biological sample (e.g., a cell) is modulated by the described methods. In certain embodiments, the expression (e.g., transcription) of a gene that is regulated by a bromodomain-containing protein in a subject or biological sample (e.g., a cell) is down-regulated or inhibited by the described methods. In certain embodiments, the gene that is regulated by a bromodomain-containing protein is an oncogene.

Another aspect of the present disclosure relates to methods of treating a disease in a subject in need thereof.
associated with a bromodomain-containing protein. In certain embodiments, the disease is associated with the activity of a bromodomain-containing protein. In certain embodiments, the disease is associated with the aberrant activity or increased activity of a bromodomain-containing protein.

In certain embodiments, the disease is associated with a bromodomain (e.g., a bromodomain of a bromodomain-containing protein). In certain embodiments, the disease is associated with the activity of a bromodomain. In certain embodiments, the disease is associated with the aberrant activity or increased activity of a bromodomain. In certain embodiments, the disease is associated with the function (e.g., dysfunction) of a bromodomain.

In certain embodiments, the disease described herein is driven by a transcriptional activator. In certain embodiments, the transcriptional activator is Myc. In certain embodiments, the disease is associated with a NUT rearrangement. In certain embodiments, the disease is associated with aberrant Myc function. In certain embodiments, the disease is associated with the interleukin 7 receptor (IL7R).

In certain embodiments, the disease is a proliferative disease (e.g., a proliferative disease described herein). In certain embodiments, the disease is cancer (e.g., a cancer described herein). In certain embodiments, the disease is lung cancer. In certain embodiments, the disease is multiple myeloma. In certain embodiments, the disease is neuroblastoma. In certain embodiments, the disease is colon cancer. In certain embodiments, the disease is testicular cancer. In certain embodiments, the disease is ovarian cancer. In certain embodiments, the disease is lung cancer (e.g., small-cell lung cancer or non-small-cell lung cancer). In certain embodiments, the disease is NUT midline carcinoma (e.g., BRD3 NUT midline carcinoma or BRD4 NUT midline carcinoma). In certain embodiments, the disease is leukemia. In certain embodiments, the disease is mixed-lineage leukemia (MLL). In certain embodiments, the disease is acute myelocytic leukemia (AML), biphenotypic B myelomonocytic leukemia, or erythroleukemia. In certain embodiments, the disease is selected from the group consisting of Burkitt's lymphoma, breast cancer, colon cancer, neuroblastoma, glial blastoma multiforme, chronic lymphocytic leukemia, and squamous cell carcinoma.

In certain embodiments, the disease is a benign neoplasm (e.g., a benign neoplasm described herein).

In certain embodiments, the disease is an inflammatory disease (e.g., an inflammatory disease described herein). In certain embodiments, the disease is a disease that involves an inflammatory response to an infection with a bacterium, virus, fungus, parasite, and/or protozoon. In certain embodiments, the disease is selected from the group consisting of osteoarthritis, acute gout, multiple sclerosis, an inflammatory bowel disease (e.g., Crohn's disease and ulcerative colitis), neuroinflammation, asthma, a chronic obstructive airways disease, pneumonitis, myositis, eczema, dermatitis, acne, cellulitis, an occlusive disease, thrombosis, alopecia, nephritis, vasculitis, retinitis, uveitis, scleritis, sclerosing cholangitis, hypophysitis, thyroiditis, septic shock, systemic inflammatory response syndrome (SIRS), toxic shock syndrome, acute lung injury, ARDS (adult respiratory distress syndrome), acute renal failure, burns, pancreatitis (e.g., acute pancreatitis), post-surgical syndromes, sarcoidosis, Herxheimer reactions, encephalitis, myelitis, meningitis, and malaria. In certain embodiments, the disease is acute or chronic pancreatitis. In certain embodiments, the disease is burns. In certain embodiments, the disease is an inflammatory bowel disease. In certain embodiments, the disease is neuroinflammation. In certain embodiments, the disease is sepsis or sepsis syndrome. In certain embodiments, the disease is graft-versus-host disease (GVHD).

In certain embodiments, the disease is an autoimmune disease (e.g., an autoimmune disease described herein). In certain embodiments, the disease is rheumatoid arthritis. In certain embodiments, the disease is psoriasis, systemic lupus erythematosus, vitiligo, a bullous skin disease.

In certain embodiments, the disease is a cardiovascular disease. In certain embodiments, the disease is atherogenesis or atherosclerosis. In certain embodiments, the disease is arterial stent occlusion, heart failure (e.g., congestive heart failure), a coronary arterial disease, myocarditis, pericarditis, a cardiac valvular disease, stenosis, restenosis, in-stent-stenosis, angina pectoris, myocardial infarction, acute coronary syndromes, coronary artery bypass grafting, a cardiopulmonary bypass procedure, endotoxemia, ischemia-reperfusion injury, cerebrovascular ischemia (stroke), renal reperfusion injury, embolism (e.g., pulmonary, renal, hepatic, gastro-intestinal, or peripheral limb embolism), or myocardial ischemia.

In certain embodiments, the disease is a viral infection. In certain embodiments, the disease is an infection caused by DNA virus. In certain embodiments, the disease is an infection caused by a dsDNA virus. In certain embodiments, the disease is an infection caused by an ssDNA virus. In certain embodiments, the disease is an infection caused by an RNA virus. In certain embodiments, the disease is an infection caused by a dsRNA virus. In certain embodiments, the disease is an infection caused by a (+)ssRNA virus. In certain embodiments, the disease is an infection caused by a (−)ssRNA virus. In certain embodiments, the disease is an infection caused by a reverse transcribing (RT) virus. In certain embodiments, the disease is an infection caused by an ssRNA-RT virus. In certain embodiments, the disease is an infection caused by a dsDNA-RT virus. In certain embodiments, the disease is an infection caused by human immunodeficiency virus (HIV). In certain embodiments, the disease is an infection caused by acquired immunodeficiency syndrome (AIDS). In certain embodiments, the disease is an infection caused by human papillomavirus (HPV). In certain embodiments, the disease is an infection caused by hepatitis C virus (HCV). In certain embodiments, the disease is an infection caused by a herpes virus (e.g., herpes simplex virus (HSV)). In certain embodiments, the disease is an infection caused by Ebola virus. In certain embodiments, the disease is an infection caused by severe acute respiratory syndrome (SARS). In certain embodiments, the disease is an infection caused by influenza virus. In certain embodiments, the disease is an infection caused by an influenza virus. In certain embodiments, the disease is an infection caused by an influenza A virus. In certain embodiments, the disease is human flu (e.g., human flu caused by H1N1, H2N2, H3N2, H5N1, H7N7, H1N2, H9N2, H7N2, H7N3, or H10N7 virus). In certain embodiments, the disease is bird flu (e.g., bird flu caused by H5N1 or H7N9 virus). In certain embodiments, the disease is swine influenza (e.g., swine influenza caused by H1N1, H1N2, H2N1, H3N1, H3N2, H2N3, or influenza C virus). In certain embodiments, the disease is equine influenza (e.g., equine influenza caused by H7N7 or H3N8 virus). In certain embodiments, the disease is canine influenza (e.g., canine influenza caused by H3N8 virus). In certain embodiments, the disease is an infection caused by an influenza B virus. In certain embodiments, the disease is an infection caused by an influenza C virus. In certain embodiments, the disease is Dengue fever, Dengue hemorrhagic fever (DHF), Dengue shock syndrome (DSS), hepatitis A, hepatitis B, hepatitis D, hepatitis E, hepatitis F, infection caused by Coxsackie A virus, infection caused by Coxsackie B virus, fulminant viral hepatitis, viral myocarditis, infection caused by parainfluenza virus, infection caused by an RS virus (RSV) (e.g., RSV bronchiolitis, RSV pneumonia, especially an infant and childhood infection caused by RSV and RSV pneumonia in the patients with cardiopulmonary disorders), infection caused by measles virus, infection caused by vesicular stomatitis virus, infection caused by rabies virus, Japanese encephalitis, infection caused by Junin virus, infection caused by human cytomegalovirus, infection caused by varicellovirus, infection caused by cytomegalovirus, infection caused by muromegalovirus, infection caused by proboscivirus, infection caused by roscolovirus, infection caused by lymphocryptovirus, infection caused by macavirus, infection caused by percavirus, infection caused by rhadinovirus, infection caused by poliovirus, infection caused by Marburg virus, infection caused by Lassa fever virus, Venezuelan equine encephalitis, infection caused by Rift Valley Fever virus, infection caused by Korean hemorrhagic fever virus, infection caused by Crimean-Congo hemorrhagic fever virus, encephalitis, Saint Louise encephalitis, Kyasanur Forest disease, Murray Valley encephalitis, tick-borne encephalitis, West Nile encephalitis, yellow fever, infection caused by adenovirus, infection caused by poxvirus, or a viral infection in subjects with immune disorders.

In certain embodiments, the disease is a fibrotic condition. In certain embodiments, the disease is selected from the group consisting of renal fibrosis, post-operative stricture, keloid formation, hepatic cirrhosis, biliary cirrhosis, and cardiac fibrosis. In certain embodiments, the disease is scleroderma. In certain embodiments, the disease is idiopathic pulmonary fibrosis.

In certain embodiments, the disease is an endocrine disease. In certain embodiments, the disease is Addison's disease.

In certain embodiments, the disease is a neurological disease (e.g., Alzheimer's disease).

In certain embodiments, the disease is a metabolic disease. In certain embodiments, the disease is diabetes. In certain embodiments, the disease is type 1 diabetes. In certain embodiments, the disease is Type II diabetes or gestational diabetes. In certain embodiments, the disease is obesity. In certain embodiments, the disease is fatty liver (NASH or otherwise), cachexia, hypercholesterolemia, or a disorder of lipid metabolism via the regulation of apolipoprotein A1 (APOA1).

In certain embodiments, the disease is radiation poisoning. In certain embodiments, the disease is radiation injury.

In certain embodiments, the disease is acute rejection of transplanted organs or multi-organ dysfunction syndrome.

In still another aspect, the present disclosure provides methods of preventing a disease described herein in a subject in need thereof.

disclosure provides methods of reducing the risk of developing a disease described herein in a subject in need thereof.

disclosure provides methods for male contraception in a male subject in need thereof.

In yet another aspect, the present disclosure provides methods of inhibiting sperm formation in a subject in need thereof.

Another aspect of the present disclosure relates to methods of inhibiting the replication of a virus. In certain embodiments, the replication of the virus is inhibited by the described methods.

in vitro. In certain embodiments, the virus is In certain embodiments, the virus described herein is present ex vivo. In certain embodiments, the virus is in vivo.

Another aspect of the present disclosure relates to methods of killing a virus. In certain embodiments, the virus is killed by the described methods.

Another aspect of the disclosure relates to methods of inhibiting the interaction between a bromodomain-containing protein and an immunoglobulin (Ig) regulatory element in a subject.

Another aspect of the disclosure relates to methods of inhibiting the interaction between a bromodomain-containing protein and an immunoglobulin (Ig) regulatory element in a biological sample (e.g., a cell).

Another aspect of the disclosure relates to methods of inducing apoptosis (e.g., apoptosis of a cancer cell) in a cell of a subject.

Another aspect of the disclosure relates to methods of inducing apoptosis in a cell of a biological sample (e.g., an in vitro cell, a cancer cell).

Another aspect of the disclosure relates to methods of method for inducing G1 arrest in a cell of a subject.

Another aspect of the disclosure relates to methods of method for inducing G1 arrest in a cell of a biological sample.

In certain embodiments, the methods of the disclosure include administering to a subject in need thereof an effective amount of a compound or pharmaceutical composition described herein. In certain embodiments, the methods of the disclosure include administering to a subject in need thereof a therapeutically effective amount of a compound or pharmaceutical composition described herein. In certain embodiments, the methods of the disclosure include administering to a subject in need thereof a prophylactically effective amount of a compound or pharmaceutical composition described herein. In certain embodiments, the methods of the disclosure include contacting a biological sample (e.g., a cell) with an effective amount of a compound or pharmaceutical composition described herein. In certain embodiments, the methods of the disclosure include contacting a virus with an effective amount of a compound or pharmaceutical composition described herein.

In another aspect, the present disclosure provides the compounds described herein for use in a method of the disclosure, or use in the manufacture of a medicament for use in a method or treatment described herein.

In still another aspect, the present disclosure provides the pharmaceutical compositions described herein for use in a method of the disclosure, or use in the manufacture of a medicament for use in a method or treatment described herein.

Methods of Screening a Library of Compounds

Another aspect of the disclosure relates to methods of screening a library of compounds, and pharmaceutical acceptable salts thereof, to identify a compound, or a pharmaceutical acceptable salt thereof, that is useful in the methods of the disclosure. In certain embodiments, the methods of screening a library include obtaining at least two different compounds described herein; and performing at least one assay using the different compounds described herein. In certain embodiments, at least one assay is useful in identifying a compound that is useful in the described methods.

Typically, the methods of screening a library of compounds involve at least one assay. In certain embodiments, the assay is performed to detect one or more characteristics associated with the treatment and/or prevention of a disease described herein, with the inhibition of the activity of a bromodomain-containing protein, with the inhibition of the activity of a bromodomain, with the inhibition of the binding of a bromodomain to an acetyl-lysine residue of a second protein (e.g., a histone), with the modulation (e.g., inhibition) of the transcriptional elongation, with the modulation (e.g., inhibition) of the expression (e.g., transcription) of a gene that is regulated by a bromodomain-containing protein, with the induction of apoptosis, and/or with the induction of G1 arrest. The characteristics may be desired characteristics (e.g., a disease having been treated, a disease having been prevented, the risk of developing a disease having been reduced, the replication of a virus having been inhibited, a virus having been killed, the activity of a bromodomain-containing protein having been inhibited, the activity of a bromodomain, the binding of a bromodomain to an acetyl-lysine residue of a second protein (e.g., a histone) having been inhibited, the transcriptional elongation having been modulated (e.g., having been inhibited), the expression (e.g., transcription) of a gene that is regulated by a bromodomain-containing protein having been modulated (e.g., having been inhibited), the apoptosis having been induced, or the G1 arrest having been induced). The characteristics may be undesired characteristics (e.g., a disease having not been treated, a disease having not been prevented, the risk of developing a disease having not been reduced, the replication of a virus having not been inhibited, a virus not having been killed, the activity of a bromodomain-containing protein having not been inhibited, the activity of a bromodomain having not been inhibited, the binding of a bromodomain to an acetyl-lysine residue of a second protein (e.g., a histone) having not been inhibited, the transcriptional elongation having not been modulated (e.g., having not been inhibited), the expression (e.g., transcription) of a gene that is regulated by a bromodomain-containing protein having not been modulated (e.g., having not been inhibited), the apoptosis having not been induced, or the G1 arrest having not been induced). The assay may be an immunoassay, such as a sandwich-type assay, competitive binding assay, one-step direct test, two-step test, or blot assay. The step of performing at least one assay may be performed robotically or manually. In certain embodiments, the assay comprises (a) contacting a library of compounds with a bromodomain-containing protein; and (b) detecting the binding of the library of compounds to the bromodomain-containing protein. In certain embodiments, the assay comprises detecting the specific binding of the library of compounds to the bromodomain-containing protein. In certain embodiments, the assay comprises detecting the specific binding of the library of compounds to a bromodomain of the bromodomain-containing protein. In certain embodiments, the detected binding of the library of compounds to the bromodomain-containing protein is useful in identifying the compound that is useful in the methods of the disclosure. In certain embodiments, the step of detecting the binding comprises using differential scanning fluorimetry (DSF), isothermal titration calorimetry (ITC), and/or an amplified luminescence proximity homogeneous assay (ALPHA). The step of performing at least one assay may be performed in a cell (e.g., a cancer cell) in vitro, ex vivo, or in vivo. In certain embodiments, the step of performing at least one assay is performed in a cell (e.g., a cancer cell) in vitro. In certain embodiments, the assay comprises (a) contacting a library of compounds with a cell; and (b) detecting a decrease in cell proliferation, an increase in cell death, and/or an increase in cell differentiation. In certain embodiments, the cell death is apoptotic cell death. In certain embodiments, the cell differentiation is identified by detecting an increase in cytokeratin expression. In certain embodiments, the step of performing at least one assay further comprises detecting a reduction in transcriptional elongation.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

Example I. Preparation of the Compounds

Exemplary Preparation of Compounds of Formula (I)

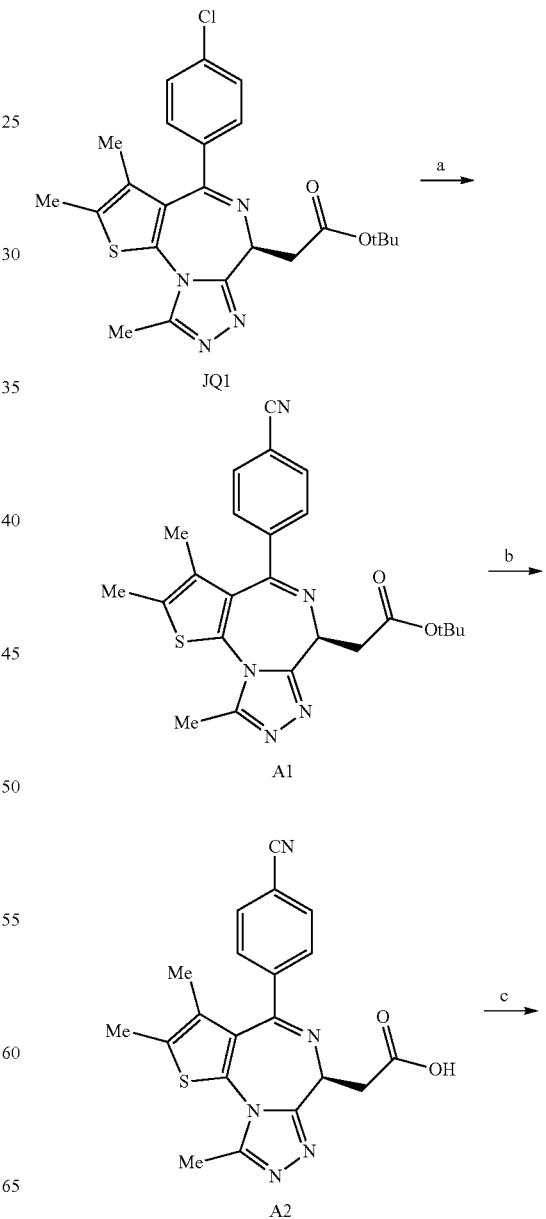

131
-continued

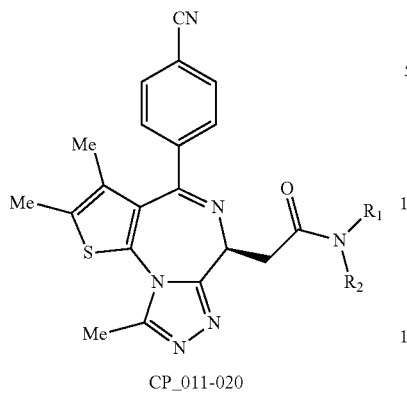

CP_011-020 a) Zn(CN)$_2$, Pd$_2$(dba)$_3$, dppf, Zn, DMA; b) TFA, CH$_2$Cl$_2$; c) NHR$_1$R$_2$, HATU, iPr$_2$NEt, DMF Intermediate A1

Pd$_2$(dba)$_3$ (16.3 mg, 0.04 eq), dppf (19.3 mg, 0.08 eq), Zn(CN)$_2$ (61.6 mg, 1.2 eq), and Zn (7 mg, 0.24 eq) was added to the solution of JQ1 (200 mg) in 4 mL DMA. The mixture was purged with argon and stirred at 140° C. overnight. After cooling to rt, the mixture was diluted with EtOAc, washed with 2N NH$_3$.H$_2$O and brine, dried over Na$_2$SO$_4$, filtered and concentrated under reduced pressure. The residue was purified by flash chromatography to give Intermediate A1 (80 mg, 41%).

Intermediate A2

Intermediate A1 (80 mg) was dissolved in 1:1 CH$_2$Cl$_2$/TFA. The mixture was stirred at room temperature for 1 hour. The volatile was removed under reduced pressure. The residue was purified by RP-HPLC to give Intermediate A2 (40 mg, 57%).

CP_011-020 (Compound 110)

HATU (95 mg, 5 eq) was added to the solution of compound 2 (19 mg) in DMF (0.5 mL). The mixture was stirred for 10 mins before NHR$_1$R$_2$ (5 eq) and iPr$_2$Net (61 µL, 5 eq) was added. The mixture was stirred for 2 hours before quenched with H$_2$O. The mixture was diluted with EtOAc, washed with H$_2$O and brine, dried over Na$_2$SO$_4$, filtered and concentrated under reduced pressure. The residue was purified RP-HPLC to give CP_011-020 (Compound 110) (55-75%). $^1$H NMR (400 MHz, CD$_3$OD, 25° C.) δ 7.79 (d, J=8.0 Hz, 2H), 7.66 (d, J=8.0 Hz, 2H), 4.80 (t, J=6.8 Hz, 1H), 3.82-3.64 (m, 10H), 2.77 (s, 3H), 2.48 (s, 3H), 1.71 (s, 3H). $^{13}$C NMR (100 MHz, CD$_3$OD, 25° C.) δ 169.3, 163.6, 142.0, 132.6, 132.1, 132.0, 130.5, 130.4, 129.3, 117.8, 113.9, 66.3, 54.1, 45.9, 42.0, 34.4, 13.0, 11.6, 10.2. LC-MS for C$_{24}$H$_{24}$N$_6$O$_2$S [M+H]$^+$: 461.1 m/z.

132
Exemplary Preparation of Compounds of Formula (II)

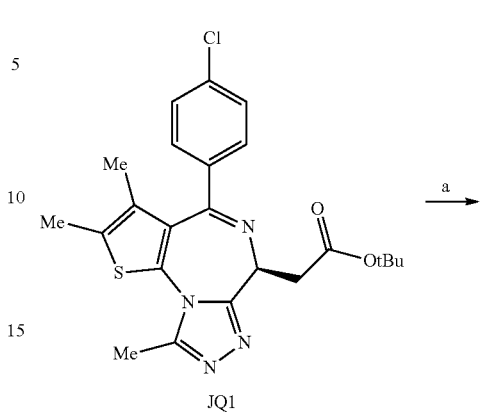

JQ1

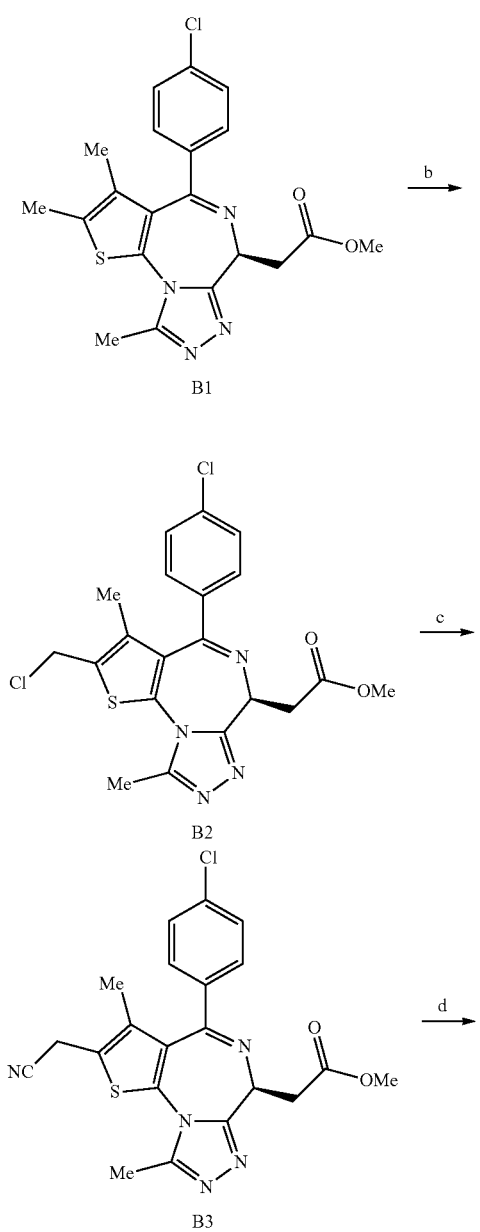

B1

B2

B3

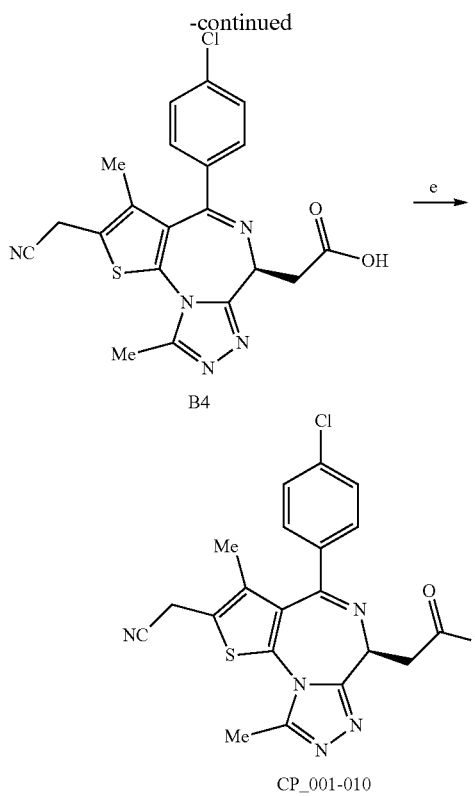

B4

CP_001-010 a) MeOH, H₂SO₄; b) SO₂Cl₂, CH₂Cl₂; c) KCN, DMF; d) LiOH, THF/H₂O; e) HATU, NHR₁R₂, iPr₂NEt, DMF

Intermediate B1

Concentrated $H_2SO_4$ (5 drops, cat.) was added slowly to the solution of JQ1 (1 g) in MeOH (10 mL). The mixture was refluxed overnight. After cooling to room temperature, the volatile was removed under reduced pressure. The residue was purified by flash chromatography to give Intermediate B1 (817 mg, 90%).

Intermediate B2

$SO_2Cl_2$ (74 μL, 3 eq) was added to the solution of Intermediate B1 (124 mg) in $CH_2Cl_2$ (3 mL) at 0° C. The mixture was stirred at room temperature for 4 hours. The reaction was quenched with $H_2O$. The aqueous layer was extracted with $CH_2Cl_2$ twice. The combined organic layer was dried over $Na_2SO_4$, filtered and concentrated under reduced pressure. The residue was purified by flash chromatography to give Intermediate B2 (45 mg, 34%).

Intermediate B3

KCN (40 mg, 2 eq) was added to the solution of Intermediate B2 (135 mg) in DMF (3 mL). The mixture was stirred at 90° C. for 4 hours. After cooling to room temperature, the mixture was diluted with EtOAc, washed with $H_2O$ and brine, dried over $Na_2SO_4$, filtered and concentrated under reduced pressure. The residue was purified by flash chromatography to give Intermediate B3 (92 mg, 67%).

Intermediate B4

3M LiOH solution (1 mL) was added to the solution of Intermediate B3 (208 mg) in THF (4 mL). The mixture was stirred at rt for 2 hours. The mixture was acidified with 1N HCl, and extracted with EtOAc three times. The combined organic layers was washed with brine, dried over $Na_2SO_4$, filtered and concentrated under reduced pressure. The residue was purified by RP-HPLC to give Intermediate B4 (151 mg, 80%).

CP_001-010 (Compound 210)

HATU (95 mg, 5 eq) was added to the solution of Intermediate B4 (20 mg) in DMF (0.5 mL). The mixture was stirred for 10 mins before $NHR_1R_2$ (5 eq) and $iPr_2NEt$ (61 μL, 5 eq) was added. The mixture was stirred for 2 hours before quenched with $H_2O$. The mixture was diluted with EtOAc, washed with $H_2O$ and brine, dried over $Na_2SO_4$, filtered and concentrated under reduced pressure. The residue was purified RP-HPLC to give CP-001-010 (55-75%).
$^1H$ NMR (400 MHz, $CD_3OD$, 25° C.) δ 7.53 (d, J=8.8 Hz, 2H), 7.48 (d, J=8.8 Hz, 2H), 4.74 (t, J=6.8 Hz, 1H), 3.82-3.63 (m, 10H), 3.45-3.28 (m, 2H), 2.75 (s, 3H), 2.62 (s, 3H). $^{13}C$ NMR (100 MHz, $CD_3OD$, 25° C.) δ 169.4, 163.5, 137.1, 136.3, 136.1, 133.4, 130.1, 129.4, 128.9, 123.7, 116.0, 66.3, 54.0, 45.9, 42.0, 34.5, 15.7, 11.8, 10.2. LC-MS for $C_{24}H_{23}ClN_6O_2S$ $[M+H]^+$: 495.1 m/z.

Characterization of Selected Compounds

Compound 201

$^1H$ NMR (400 MHz, $CD_3OD$, 25° C.) δ 7.51 (d, J=8.4 Hz, 2H), 7.45 (d, J=8.4 Hz, 2H), 7.41 (d, J=8.8 Hz, 2H), 6.76 (d, J=8.8 Hz, 2H), 4.75 (dd, J=8.4, 5.6 Hz, 1H), 3.62 (dd, J=15.2, 8.8 Hz 1H), 3.51 (dd, J=15.2, 8.8 Hz 1H), 3.35 (m, 2H), 2.76 (s, 3H), 2.62 (s, 3H). $^{13}C$ NMR (100 MHz, $CD_3OD$, 25° C.) δ 169.2, 163.7, 154.1, 137.1, 136.4, 136.1, 133.3, 130.2, 130.1, 129.4, 128.8, 123.7, 121.9, 116.0, 114.8, 53.8, 37.8, 15.8, 11.8, 10.2. LC-MS for $C_{26}H_{21}ClN_6O_2S$ $[M+H]^+$: 517.1 m/z.

Compound 202

$^1H$ NMR (400 MHz, $CD_3OD$, 25° C.) δ 7.53 (d, J=8.4 Hz, 2H), 7.47 (d, J=8.4 Hz, 2H), 4.70 (dd, J=8.4, 5.6 Hz, 1H), 3.46-3.25 (m, 6H), 2.76 (s, 3H), 2.62 (s, 3H), 1.20 (t, J=7.6 Hz, 3H). $^{13}C$ NMR (100 MHz, $CD_3OD$, 25° C.) δ 170.9, 163.7, 154.1, 137.2, 136.5, 136.0, 133.2, 130.1, 129.5, 128.9, 123.7, 116.0, 53.8, 37.2, 34.0, 15.8, 13.5, 11.8, 10.2. LC-MS for $C_{22}H_{21}ClN_6OS$ $[M+H]^+$: 453.0 m/z.

Compound 203

$^1H$ NMR (400 MHz, $CD_3OD$, 25° C.) δ 7.54 (d, J=8.0 Hz, 2H), 7.48 (d, J=8.0 Hz, 2H), 4.70 (t, J=7.2 Hz, 1H), 3.55-3.41 (m, 12H), 3.22-3.18 (m, 4H), 2.96 (s, 3H), 2.75 (s, 3H), 2.60 (s, 3H), 2.01-1.94 (m, 2H). $^{13}C$ NMR (100 MHz, $CD_3OD$, 25° C.) δ 172.2, 163.7, 154.1, 137.2, 136.1, 136.0, 133.5, 130.1, 130.0, 129.1, 128.9, 123.5, 116.1, 54.1, 53.9, 50.7, 42.1, 37.3, 35.8, 24.5, 24.4, 15.8, 11.7, 10.2. LC-MS for $C_{28}H_{33}ClN_8OS$ $[M+H]^+$: 565.2 m/z.

Compound 204

$^1H$ NMR (400 MHz, $CD_3OD$, 25° C.) δ 7.42 (d, J=8.8 Hz, 2H), 7.37 (d, J=8.8 Hz, 2H), 4.58 (t, J=7.2 Hz, 1H), 3.95 (br, 2H), 3.75-3.0 (m, 14H), 2.62 (s, 3H), 2.48 (s, 3H). $^{13}C$ NMR (100 MHz, $CD_3OD$, 25° C.) δ 183.0, 172.8, 163.9, 137.2, 136.1, 135.9, 133.6, 130.1, 129.1, 128.9, 123.5, 116.1, 63.7, 58.0, 53.8, 52.0, 37.7, 33.6, 15.8, 11.7, 10.3. LC-MS for $C_{26}H_{28}ClN_7O_2S$ $[M+H]^+$: 538.1 m/z.

Compound 205

$^1H$ NMR (400 MHz, $CD_3OD$, 25° C.) δ 7.54 (d, J=8.4 Hz, 2H), 7.47 (d, J=8.4 Hz, 2H), 4.66 (dd, J=8.4, 5.6 Hz, 1H), 3.47-3.30 (m, 6H), 2.74 (s, 3H), 2.62 (s, 3H). $^{13}C$ NMR (100 MHz, $CD_3OD$, 25° C.) δ 170.9, 163.5, 154.1, 137.2, 136.5, 136.0, 133.2, 130.1, 129.5, 128.9, 123.7, 116.0, 53.7, 36.7, 15.8, 11.8, 10.2. LC-MS for $C_{20}H_{17}ClN_6OS$ $[M+H]^+$: 425.0 m/z.

Compound 206

$^1H$ NMR (400 MHz, $CD_3OD$, 25° C.) δ 7.42 (d, J=8.4 Hz, 2H), 7.35 (d, J=8.4 Hz, 2H), 4.56 (dd, J=8.8, 5.6 Hz, 1H), 3.55 (t, J=6 Hz, 1H), 3.39-3.22 (m, 6H), 2.62 (s, 3H), 2.49 (s, 3H). $^{13}C$ NMR (100 MHz, $CD_3OD$, 25° C.) δ 171.6, 163.6, 155.5, 137.1, 136.2, 136.1, 133.4, 130.1, 129.3, 128.8, 123.6, 116.0, 60.2, 53.9, 41.7, 37.3, 15.8, 11.8, 10.2. LC-MS for $C_{22}H_{21}ClN_6O_2S$ [M+H]$^+$: 469.1 m/z.

Compound 207

$^1$H NMR (400 MHz, CD$_3$OD, 25° C.) δ 7.42 (d, J=8.4 Hz, 2H), 7.35 (d, J=8.4 Hz, 2H), 4.57 (dd, J=8.8, 5.6 Hz, 1H), 3.78 (m, 1H), 3.40-3.05 (m, 6H), 2.63 (s, 3H), 2.49 (s, 3H), 1.09 (d, J=6.4 Hz, 3H). $^{13}$C NMR (100 MHz, CD$_3$OD, 25° C.) δ 171.5, 163.7, 137.1, 136.3, 136.0, 133.3, 130.2, 129.4, 128.9, 123.6, 116.0, 66.0, 53.9, 46.5, 37.2, 19.6, 15.8, 11.8, 10.2. LC-MS for $C_{23}H_{23}ClN_6O_2S$ [M+H]$^+$: 483.1 m/z.

Compound 208

$^1$H NMR (400 MHz, CD$_3$OD, 25° C.) δ 7.53 (d, J=8.4 Hz, 2H), 7.47 (d, J=8.4 Hz, 2H), 4.68 (dd, J=8.8, 5.6 Hz, 1H), 3.90 (m, 1H), 3.51-3.19 (m, 6H), 2.74 (s, 3H), 2.61 (s, 3H), 1.20 (d, J=6.4 Hz, 3H). $^{13}$C NMR (100 MHz, CD$_3$OD, 25° C.) δ 171.5, 163.7, 137.1, 136.2, 136.1, 133.4, 130.1, 129.3, 128.8, 123.6, 116.0, 65.9, 53.9, 46.5, 37.3, 19.6, 15.8, 11.8, 10.2. LC-MS for $C_{23}H_{23}ClN_6O_2S$ [M+H]$^+$: 483.0 m/z.

Compound 209

$^1$H NMR (400 MHz, CD$_3$OD, 25° C.) δ 7.53 (d, J=8.4 Hz, 2H), 7.43 (d, J=8.4 Hz, 2H), 5.96 (tt, J=56, 4.0 Hz, 1H), 4.68 (dd, J=8.8, 5.6 Hz, 1H), 3.55 (t, J=6 Hz, 1H), 3.77-3.27 (m, 6H), 2.75 (s, 3H), 2.62 (s, 3H). $^{13}$C NMR (100 MHz, CD$_3$OD, 25° C.) δ 172.0, 163.6, 155.5, 137.1, 136.3, 136.0, 133.3, 130.1, 129.4, 128.8, 123.6, 116.0, 114.1 (t, J=239 Hz), 53.8, 41.4 (t, J=27.4 Hz), 37.1, 15.8, 11.8, 10.2. LC-MS for $C_{22}H_{19}ClF_2N_6OS$ [M+H]$^+$: 489.0 m/z.

Compound 210

$^1$H NMR (400 MHz, CD$_3$OD, 25° C.) δ 7.53 (d, J=8.8 Hz, 2H), 7.48 (d, J=8.8 Hz, 2H), 4.74 (t, J=6.8 Hz, 1H), 3.82-3.63 (m, 10H), 3.45-3.28 (m, 2H), 2.75 (s, 3H), 2.62 (s, 3H). $^{13}$C NMR (100 MHz, CD$_3$OD, 25° C.) δ 169.4, 163.5, 137.1, 136.3, 136.1, 133.4, 130.1, 129.4, 128.9, 123.7, 116.0, 66.3, 54.0, 45.9, 42.0, 34.5, 15.7, 11.8, 10.2. LC-MS for $C_{24}H_{23}ClN_6O_2S$ [M+H]$^+$: 495.1 m/z.

Compound 101

$^1$H NMR (400 MHz, CD$_3$OD, 25° C.) δ 7.77 (d, J=8.4 Hz, 2H), 7.65 (d, J=8.4 Hz, 2H), 7.41 (d, J=8.8 Hz, 2H), 6.77 (d, J=8.8 Hz, 2H), 4.75 (dd, J=8.8, 5.6 Hz, 1H), 3.64 (dd, J=15.2, 8.8 Hz 1H), 3.51 (dd, J=15.2, 8.8 Hz 1H), 2.79 (s, 3H), 2.48 (s, 3H), 1.70 (s, 3H). $^{13}$C NMR (100 MHz, CD$_3$OD, 25° C.) δ 169.1, 164.8, 154.1, 141.9, 132.8, 132.1, 131.8, 130.6, 130.2, 129.3, 121.8, 117.8, 114.9, 113.9, 53.8, 37.8, 13.0, 11.6, 10.1. LC-MS for $C_{26}H_{22}N_6O_2S$ [M+H]$^+$: 483.1 m/z.

Compound 102

$^1$H NMR (400 MHz, CD$_3$OD, 25° C.) δ 7.81 (d, J=8.4 Hz, 2H), 7.69 (d, J=8.4 Hz, 2H), 4.87 (m, 1H), 3.48-3.28 (m, 4H), 2.94 (s, 3H), 2.52 (s, 3H), 1.73 (s, 3H), 1.21 (t, J=7.2 Hz, 3H). $^{13}$C NMR (100 MHz, CD$_3$OD, 25° C.) δ 165.3, 141.2, 137.2, 134.9, 132.1, 131.8, 131.1, 129.5, 128.9, 117.7, 114.3, 53.2, 34.0, 13.4, 12.8, 11.7, 9.8. LC-MS for $C_{22}H_{22}N_6OS$ [M+H]$^+$: 419.1 m/z.

Compound 103

$^1$H NMR (400 MHz, CD$_3$OD, 25° C.) δ 7.80 (d, J=8.0 Hz, 2H), 7.68 (d, J=8.0 Hz, 2H), 4.74 (m, 1H), 3.56-3.41 (m, 10H), 3.39-3.19 (m, 4H), 2.93 (s, 3H), 2.75 (s, 3H), 2.48 (s, 3H), 2.03-1.92 (m, 2H), 1.70 (s, 3H). $^{13}$C NMR (100 MHz, CD$_3$OD, 25° C.) δ 172.2, 164.9, 154.1, 142.0, 132.4, 132.1, 130.4, 130.1, 129.3, 128.9, 123.5, 117.8, 113.9, 54.2, 53.9, 50.8, 48.9, 42.1, 37.2, 35.6, 30.7, 24.4, 13.0, 11.5, 10.2. LC-MS for $C_{28}H_{34}N_8OS$ [M+H]$^+$: 531.2 m/z.

Compound 104

$^1$H NMR (400 MHz, CD$_3$OD, 25° C.) δ 7.81 (d, J=8.0 Hz, 2H), 7.68 (d, J=8.0 Hz, 2H), 4.73 (t, J=7.2 Hz, 1H), 4.09 (br, 2H), 3.90-3.15 (m, 12H), 2.74 (s, 3H), 2.48 (s, 3H), 1.70 (s, 3H). $^{13}$C NMR (100 MHz, CD$_3$OD, 25° C.) δ 172.8, 164.9, 142.0, 132.4, 132.1, 130.4, 130.1, 129.2, 117.8, 113.9, 63.7, 57.0, 53.7, 52.4, 51.9, 37.0, 33.5, 13.0, 11.5, 10.2. LC-MS for $C_{26}H_{29}N_7O_2S$ [M+H]$^+$: 504.2 m/z.

Compound 105

$^1$H NMR (400 MHz, CD$_3$OD, 25° C.) δ 7.80 (d, J=8.4 Hz, 2H), 7.71 (d, J=8.4 Hz, 2H), 4.83 (m, 1H), 3.54 (dd, J=15.6, 8.4 Hz, 1H), 3.40 (dd, J=15.6, 5.2 Hz, 1H), 2.91 (s, 3H), 2.51 (s, 3H), 1.72 (s, 3H). $^{13}$C NMR (100 MHz, CD$_3$OD, 25° C.) δ 165.2, 141.4, 134.4, 132.1, 131.6, 131.0, 129.5, 117.7, 114.2, 53.2, 36.1, 13.0, 11.7, 9.9. LC-MS for $C_{20}H_{18}N_6OS$ [M+H]$^+$: 391.1 m/z.

Compound 106

$^1$H NMR (400 MHz, CD$_3$OD, 25° C.) δ 7.79 (d, J=8.4 Hz, 2H), 7.68 (d, J=8.4 Hz, 2H), 4.75 (dd, J=8.8, 5.6 Hz, 1H), 3.69 (t, J=5.6 Hz, 1H), 3.53-3.32 (m, 4H), 2.78 (s, 3H), 2.48 (s, 3H), 1.70 (s, 3H). $^{13}$C NMR (100 MHz, CD$_3$OD, 25° C.) δ 171.4, 164.8, 141.9, 132.8, 132.1, 131.8, 130.5, 129.3, 117.8, 113.9, 60.2, 53.9, 41.7, 37.1, 13.0, 11.6, 10.1. LC-MS for $C_{22}H_{22}N_6O_2S$ [M+H]$^+$: 435.1 m/z.

Compound 107

$^1$H NMR (400 MHz, CD$_3$OD, 25° C.) δ 7.79 (d, J=8.4 Hz, 2H), 7.68 (d, J=8.4 Hz, 2H), 4.78 (dd, J=8.8, 5.6 Hz, 1H), 3.91 (m, 1H), 3.51 (dd, J=15.2, 8.8 Hz, 1H), 3.40-3.31 (m, 2H), 3.24 (dd, J=15.2, 7.2 Hz, 1H), 2.82 (s, 3H), 2.49 (s, 3H), 1.70 (s, 3H), 1.21 (d, J=6.4 Hz, 3H). $^{13}$C NMR (100 MHz, CD$_3$OD, 25° C.) δ 171.2, 164.9, 141.7, 133.3, 132.1, 131.3, 130.9, 130.7, 129.4, 117.8, 114.0, 66.0, 53.7, 46.5, 37.0, 19.6, 13.0, 11.6, 10.1. LC-MS for $C_{23}H_{24}N_6O_2S$ [M+H]$^+$: 449.1 m/z.

Compound 108

$^1$H NMR (400 MHz, CD$_3$OD, 25° C.) δ 7.79 (d, J=8.4 Hz, 2H), 7.69 (d, J=8.4 Hz, 2H), 4.80 (m, 1H), 3.91 (m, 1H), 3.57-3.26 (m, 4H), 2.85 (s, 3H), 2.50 (s, 3H), 1.70 (s, 3H), 1.22 (d, J=6.4 Hz, 3H). $^{13}$C NMR (100 MHz, CD$_3$OD, 25° C.) δ 171.1, 165.0, 141.6, 133.7, 132.0, 131.1, 130.9, 130.8, 129.4, 117.8, 114.0, 66.0, 53.6, 46.5, 36.9, 19.6, 13.0, 11.6, 10.0. LC-MS for $C_{23}H_{24}N_6O_2S$ [M+H]$^+$: 449.2 m/z.

Compound 109

$^1$H NMR (400 MHz, CD$_3$OD, 25° C.) δ 7.79 (d, J=8.0 Hz, 2H), 7.66 (d, J=8.0 Hz, 2H), 5.98 (tt, J=56, 3.6 Hz, 1H), 4.74 (dd, J=8.8, 4.8 Hz, 1H), 3.77-3.30 (m, 4H), 2.76 (s, 3H), 2.48 (s, 3H), 1.70 (s, 3H). $^{13}$C NMR (100 MHz, CD$_3$OD, 25° C.) δ 172.0, 164.6, 155.5, 142.0, 132.6, 132.1, 132.0, 130.5, 130.4, 129.2, 117.8, 116.4, 114.0 (t, J=239 Hz), 113.9, 53.8, 41.1 (t, J=26.5 Hz), 37.0, 13.0, 11.5, 10.1. LC-MS for $C_{22}H_{20}F_2N_6OS$ [M+H]$^+$: 455.1 m/z.

Compound 110

$^1$H NMR (400 MHz, CD$_3$OD, 25° C.) δ 7.79 (d, J=8.0 Hz, 2H), 7.66 (d, J=8.0 Hz, 2H), 4.80 (t, J=6.8 Hz, 1H), 3.82-3.64 (m, 10H), 2.77 (s, 3H), 2.48 (s, 3H), 1.71 (s, 3H). $^{13}$C NMR (100 MHz, CD$_3$OD, 25° C.) δ 169.3, 163.6, 142.0, 132.6, 132.1, 132.0, 130.5, 130.4, 129.3, 117.8, 113.9, 66.3, 54.1, 45.9, 42.0, 34.4, 13.0, 11.6, 10.2. LC-MS for $C_{24}H_{24}N_6O_2S$ [M+H]$^+$: 461.1 m/z.

Compound 111

$^1$H NMR (400 MHz, CD$_3$OD, 25° C.) δ 7.78 (d, J=8.4 Hz, 2H), 7.65 (d, J=8.4 Hz, 2H), 4.74 (dd, J=8.8, 4.8 Hz, 1H), 4.11-3.92 (m, 2H), 3.56 (dd, J=15.2, 9.2 Hz, 1H), 3.41 (dd, J=15.2, 4.8 Hz, 1H), 2.76 (s, 3H), 2.48 (s, 3H), 1.70 (s, 3H). $^{13}$C NMR (100 MHz, CD$_3$OD, 25° C.) δ 171.8, 164.6, 142.0, 132.6, 132.1, 132.0, 130.5, 130.4, 129.2, 125.9, 117.8, 113.9, 53.8, 40.1, 39.8, 37.0, 13.0, 11.5, 10.1. LC-MS for $C_{22}H_{19}F_3N_6OS$ [M+H]$^+$: 473.1 m/z.

Compound 100

$^1$H NMR (400 MHz, CDCl$_3$, 25° C.) δ 7.67 (d, J=8.4 Hz, 2H), 7.59 (d, J=8.4 Hz, 2H), 4.61 (t, J=6.8 Hz, 1H), 3.55 (m, 2H), 3.35 (m, 2H), 2.71 (s, 3H), 2.43 (s, 3H), 1.67 (s, 3H), 1.50 (s, 9H). $^{13}$C NMR (100 MHz, CDCl$_3$, 25° C.) δ 170.6, 163.3, 155.1, 142.1, 132.4, 132.3, 131.4, 130.5, 130.0, 129.1, 118.8, 114.1, 81.2, 54.1, 37.9, 28.2, 14.5, 13.2, 11.8, 0.0. LC-MS for C$_{20}$H$_{17}$N$_5$O$_2$S [M+H]$^+$: 392.1 m/z.

Example II. Selected Compounds and Biological Activity

The IC$_{50}$ of the compounds were determined by ALPHASCREENING assays for BRD4 and BRDT proteins. NMC797 cell line is a BRD4 dependent NUT midline carcinoma line. NMC797 showed high dependency on BRD4 inhibition, and the IC$_{50}$ was determined by ATPLITE assay.

Acetyl-Histone Binding Assay. Assays were performed as described previously with minor modifications from the manufacturer's protocol (PerkinElmer, USA). All reagents were diluted in 50 mM HEPES, 100 mM NaCl, 0.1% BSA, pH 7.4 supplemented with 0.05% CHAPS and allowed to equilibrate to room temperature prior to addition to plates. A 24-point 1:2 serial dilution of the ligands was prepared over the range of 150-0 μM and 4 μl transferred to low-volume 384-well plates (ProxiPlate™-384 Plus, PerkinElmer, USA), followed by 4 μl of HIS-tagged protein (BRD4/1, 250 nM, BRD4/2 and CREBBP, 2000 nM). Plates were sealed and incubated at room temperature for 30 minutes, before the addition of 4 μl of biotinylated peptide at equimolar concentration to the protein [peptide for BRD4(1) & BRD4 (2), and BRDT: H4K5acK8acK12acK16ac, H-SGRGK(Ac) GGK(Ac)GLGK(Ac)GGAK(Ac)RHRK(Biotin)-OH; peptide for CREBBP: H3K36ac, Biotin-KSAPATGGVK(Ac) KPHRYRPGT-OH (Cambridge Research Biochemicals, UK)]. Plates were sealed and incubated for a further 30 minutes, before the addition of 4 μl of streptavidin-coated donor beads (25 μg/ml) and 4 μl nickel chelate acceptor beads (25 μg/ml) under low light conditions. Plates were foil-sealed to protect from light, incubated at room temperature for 60 minutes and read on a PHERAstar FS plate reader (BMG Labtech, Germany) using an AlphaScreen 680 excitation/570 emission filter set. IC$_{50}$ values were calculated in Prism 5 (GraphPad Software, USA) after normalization against corresponding DMSO controls and are given as the final concentration of compound in the 20 μl reaction volume.

Cell Proliferation Assay. Cells were seeded into white, 384-well microtiter plates (Nunc) at 500 cells per well in a total volume of 50 μL media. The 797, TT, and TE10 cells were grown in DMEM containing 1% penicillin/streptomycin and 10% FBS. The Per403 cells were grown in DMEM containing 1% penicillin/streptomycin and 20% FBS. Compounds were delivered to microtiter assay plates by robotic pin transfer (PerkinElmer JANUS equipped with a V&P Scientific 100 nL pin tool). Following a 48 h incubation at 37° C., cells were lysed and wells were assessed for total ATP content using a commercial proliferation assay (Cell TITERGLO; Promega). Replicate measurements were analyzed with respect to dose and estimates of IC$_{50}$ were calculated by logistic regression (GRAPHPAD PRISM).

TABLE E1

IC$_{50}$ of exemplary compounds for BRDT(1), BRD4(1), and NMC797.

| Compound | IC$_{50}$ BRDT(1) (nM) | IC$_{50}$ BRD4(1) (nM) | IC$_{50}$ NMC797 (nM) |
|---|---|---|---|
| JQ1 | 77 | 29 | 21 |
| 100 | — | 97 | 185 |
| 101 | 120 | 79 | 133 |
| 102 | 458 | 120 | 275 |
| 103 | 120 | 50 | 333 |
| 104 | 216 | 53 | 183 |
| 105 | 565 | 174 | 366 |
| 106 | 105 | 33 | 328 |
| 107 | 187 | 61 | 107 |
| 108 | 133 | 52 | 258 |
| 109 | 142 | 37 | 70 |
| 110 | 197 | 89 | 116 |
| 111 | — | 117 | 125 |
| 200 | 132 | 48 | 52 |
| 201 | — | 175 | 1895 |
| 202 | — | 310 | 1134 |
| 203 | — | 134 | 6788 |
| 204 | — | 300 | 3464 |
| 205 | 612 | 206 | 903 |
| 206 | 642 | 197 | 9631 |
| 207 | — | 623 | 4249 |
| 208 | 1,197 | 415 | 6103 |
| 209 | — | 386 | 912 |
| 210 | 1,416 | 466 | 118 |
| 300 | 60 | 16 | 61 |

Pharmacokinetic parameters were determined by administration of a candidate bromodomain inhibitor to male CD1 mice. Intravenous doses were delivered at 5 mg/kg, and oral doses at 10 mg/kg (N=3). The results are listed in Table E2 and Table E3 for certain compounds described herein and for the known inhibitor JQ1. The compound half-life in mice as revealed by pharmacokinetic analyses of mean whole blood concentration with time after iIV injection at 5 mg/kg in male CD1 mice (n=3) for IV injection, and 10 mg/kg oral. The compound concentration in mouse blood was monitored over 24 hour time period to check the compound concentration in blood at 5 min, 30 mm, 1 h, 2 h, 6 h, 12, 24 h via a series bleeding.

TABLE E2

Average pharmacokinetic parameters for exemplary compounds (IV administration).

| Compound | CL (L/hr/kg) | V$_{SS}$ (L/kg) | Terminal t$_{1/2}$ (hr) | AUC$_{last}$ (hr · ng/mL) | AUC$_{INF}$ (hr · ng/mL) | MRT$_{INF}$ (hr) |
|---|---|---|---|---|---|---|
| JQ1 | 2.35 | 2.02 | 0.897 | 2130 | 2130 | 0.861 |
| 107 | 1.76 | 0.583 | 0.411 | 2916 | 2921 | 0.336 |
| 109 | 1.42 | 1.18 | 1.11 | 3505 | 3514 | 0.829 |
| 200 | 1.25 | 1.57 | 1.38 | 4001 | 4050 | 1.28 |

TABLE E3

Average pharmacokinetic parameters of exemplary compounds (oral administration).

| Compound | T$_{max}$ (hr) | C$_{max}$ (ng/mL) | Terminal t$_{1/2}$ (hr) | AUC$_{last}$ (hr · ng/mL) | AUC$_{INF}$ (hr · ng/mL) | F (%) |
|---|---|---|---|---|---|---|
| JQ1 | 0.250 | 1180 | 1.39 | 2040 | 2090 | 49.1 |
| 107 | 0.500 | 319 | 1.62 | 512 | 532 | 9.10 |
| 109 | 0.667 | 1208 | 1.69 | 3634 | 3781 | 53.8 |
| 200 | 0.500 | 1504 | 1.97 | 5522 | 6037 | 72.4 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:
1. A compound of Formula (I):

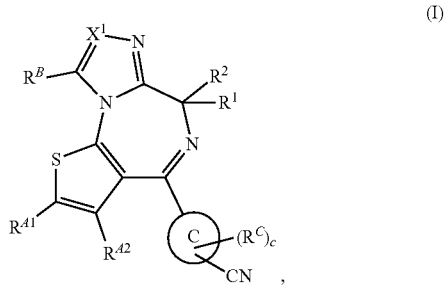

or a pharmaceutically acceptable salt, stereoisomer, or tautomer thereof, wherein:
  $R^{A1}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;
  $R^{A2}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;
  $X^1$ is N or $CR^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;
  $R^B$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;
  Ring C is of formula:

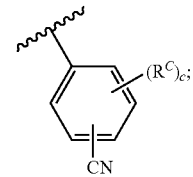

each occurrence of $R^C$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^f$, —$SR^f$, —$N(R^f)_2$, —$NO_2$, or —CN;
  c is 0, 1, 2, 3, or 4;

R¹ is
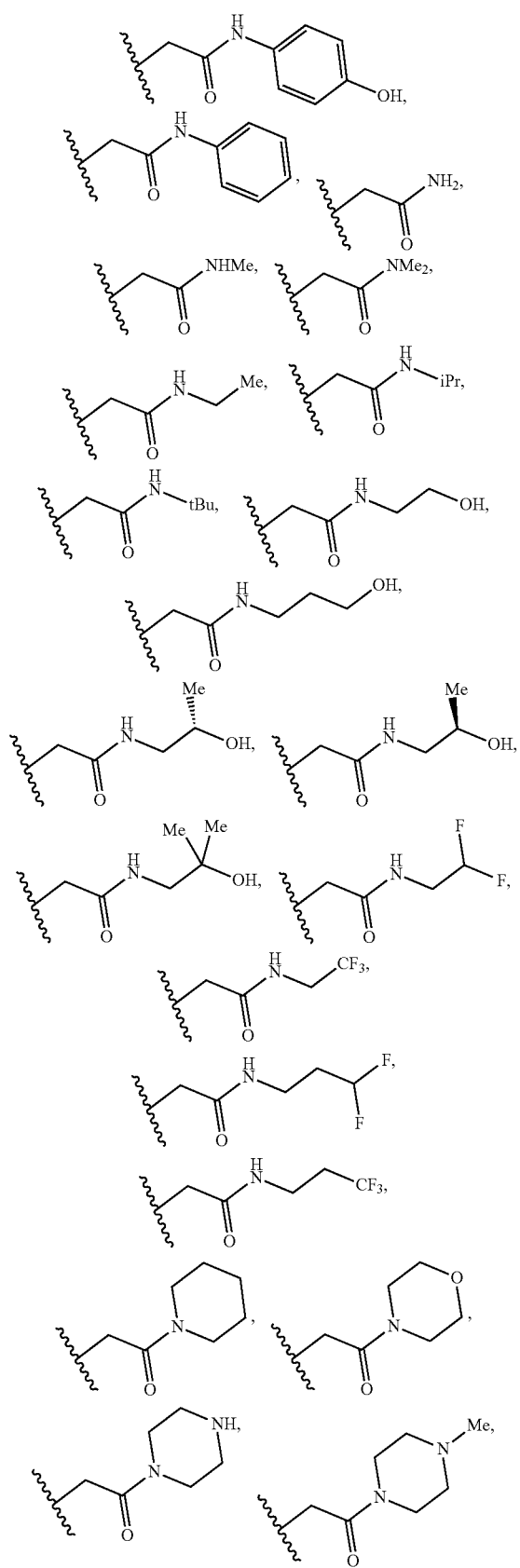
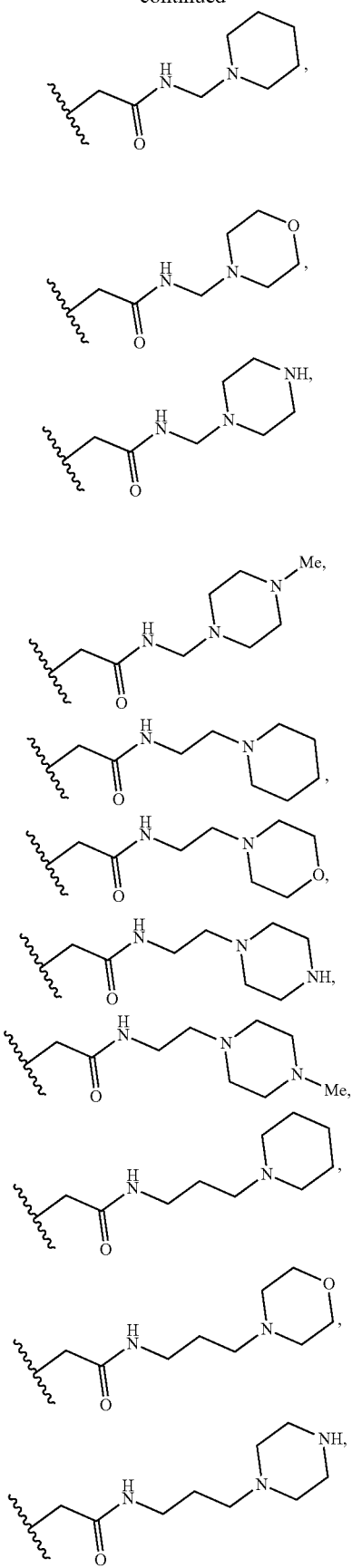

-continued

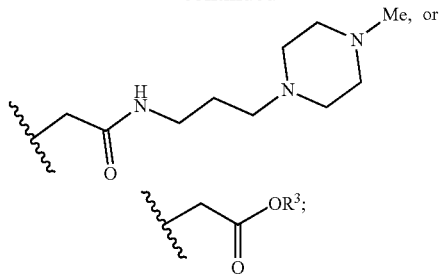

R² is hydrogen, halogen, or optionally substituted alkyl;

R³ is, optionally substituted alkyl, optionally substituted alkenyl, optionally substituted alkynyl, optionally substituted carbocyclyl, optionally substituted heterocyclyl, optionally substituted aryl, optionally substituted heteroaryl, or optionally substituted acyl, or an oxygen protecting group; and each occurrence of $R^f$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, a sulfur protecting group, or a nitrogen protecting group, or two $R^f$ are joined to form an optionally substituted heterocyclic or optionally substituted heteroaryl ring;

provided the compound is not:

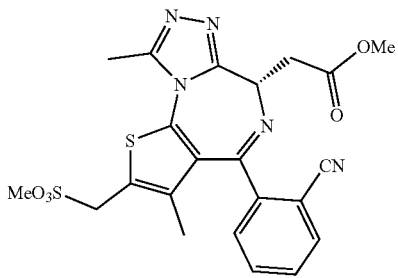

or a pharmaceutically acceptable salt, stereoisomer, or tautomer thereof;

wherein:

each oxygen protecting group is independently —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3^+$X$^-$, —P(O$R^{cc}$)$_2$, —P(O$R^{cc}$)$_3^+$X$^-$, —P(=O)($R^{aa}$)$_2$, —P(=O)(O$R^{cc}$)$_2$, or —P(=O)(N($R^{bb}$)$_2$)$_2$;

each sulfur protecting group is independently —$R^{aa}$, —N($R^{bb}$)$_2$, —C(=O)S$R^{aa}$, —C(=O)$R^{aa}$, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —SO$_2R^{aa}$, —Si($R^{aa}$)$_3$, —P($R^{cc}$)$_2$, —P($R^{cc}$)$_3^+$X$^-$, —P(O$R^{cc}$)$_2$, —P(O$R^{cc}$)$_3^+$X$^-$, —P(=O)($R^{aa}$)$_2$, —P(=O)(O$R^{cc}$)$_2$, or —P(=O)(N($R^{bb}$)$_2$)$_2$;

each nitrogen protecting group is independently —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, or 5-14 membered heteroaryl; wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups;

each instance of $R^{aa}$ is, independently, selected from the group consisting of $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from the group consisting of hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from the group consisting of hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from the group consisting of halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+$X$^-$, —N(O$R^{ee}$)$R^{ff}$, —SH, —S$R^{ee}$, —SS$R^{ee}$, —C(=O)$R^{ee}$, —CO$_2$H, —CO$_2R^{ee}$, —OC(=O)$R^{ee}$, —OCO$_2R^{ee}$, —C(=O)N($R^{ff}$)$_2$, —OC(=O)N($R^{ff}$)$_2$, —NR$^{ff}$C(=O)$R^{ee}$, —NR$^{ff}$CO$_2R^{ee}$, —NR$^{ff}$C(=O)N($R^{ff}$)$_2$, —C(=N$R^{ff}$)O$R^{ee}$, —OC(=N$R^{ff}$)$R^{ee}$, —OC (=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents are joined to form =O or =S;

each instance of R$^{ee}$ is, independently, selected from the group consisting of C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from the group consisting of hydrogen, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$alkynyl, C$_{3-10}$ carbocyclyl, 3-10 membered heterocyclyl, C$_{6-10}$ aryl, and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, selected from the group consisting of halogen, —CN, —NO$_2$, —N$_3$, —SO$_2$H, —SO$_3$H, —OH, —OC$_{1-6}$ alkyl, —ON(C$_{1-6}$ alkyl), —N(C$_{1-6}$ alkyl)$_2$, —N(C$_{1-6}$ alkyl)$_3$$^+$X$^-$, —NH(C$_{1-6}$ alkyl)$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl), —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, and 5-10 membered heteroaryl; or two geminal R$^{gg}$ substituents are joined to form =O or =S;

wherein X$^-$ is a counterion.

2. The compound of claim 1, wherein the compound is of Formula (I-A-1), (I-A-2), (I-B-1), or (I-C-1):

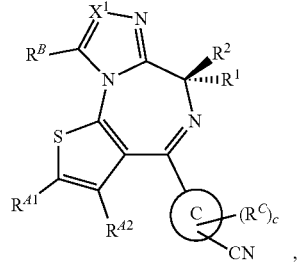

(I-A-1)

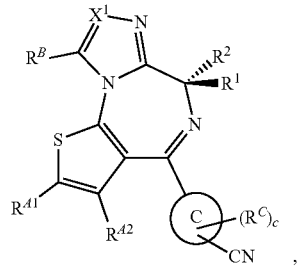

(I-A-2)

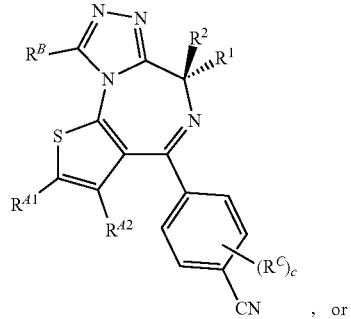

(I-B-1)

, or

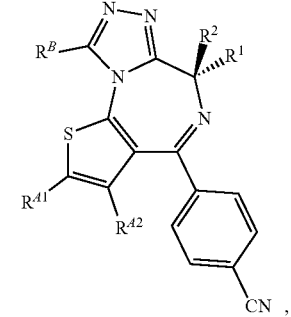

(I-C-1)

or a pharmaceutically acceptable salt, stereoisomer, or tautomer thereof.

3. The compound of claim 1, or a pharmaceutically acceptable salt, stereoisomer, or tautomer thereof, wherein Ring C is of formula:

147

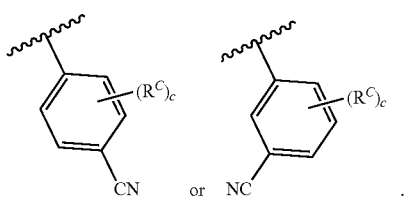

4. The compound of claim 1, or a pharmaceutically acceptable salt, stereoisomer, or tautomer thereof, wherein both $R^{A1}$ and $R^{A2}$ are hydrogen or optionally substituted $C_{1-6}$ alkyl.

5. The compound of claim 1, or a pharmaceutically acceptable salt, stereoisomer, or tautomer thereof, wherein $R^1$ is:

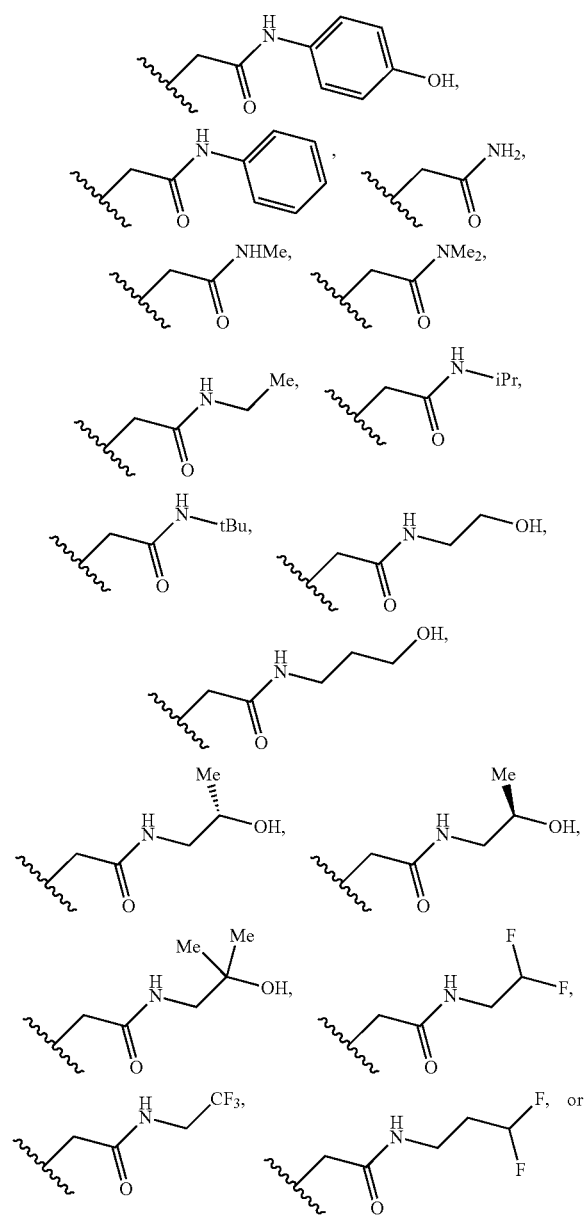

148

-continued

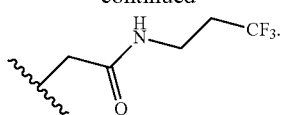

6. The compound of claim 1, or a pharmaceutically acceptable salt, stereoisomer, or tautomer thereof, wherein $R^1$ is:

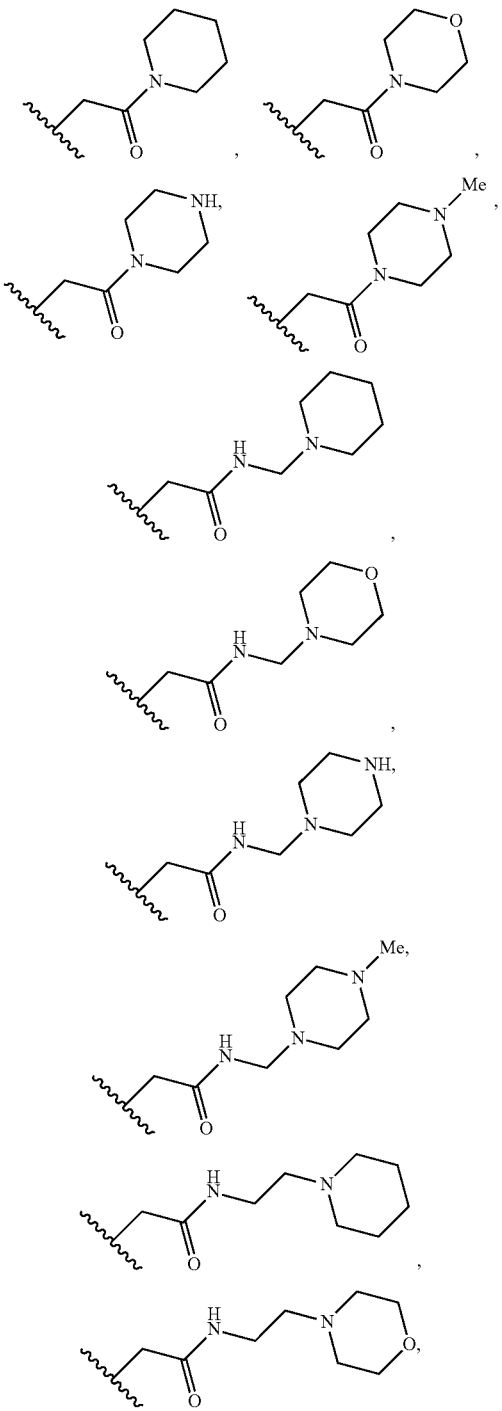

-continued

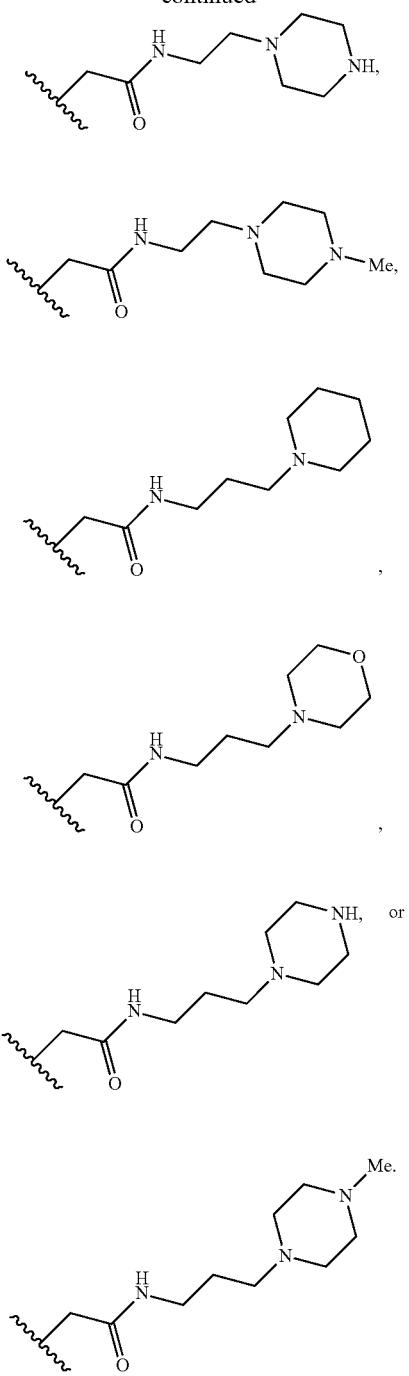

7. The compound of claim 1, or a pharmaceutically acceptable salt, stereoisomer, or tautomer thereof, wherein $R^2$ is hydrogen.

8. The compound of claim 1, or a pharmaceutically acceptable salt, stereoisomer, or tautomer thereof, wherein $X^1$ is N.

9. The compound of claim 1, or a pharmaceutically acceptable salt, stereoisomer, or tautomer thereof, wherein $R^B$ is hydrogen or optionally substituted $C_{1-6}$ alkyl.

10. The compound of claim 1, wherein the compound is of formula:

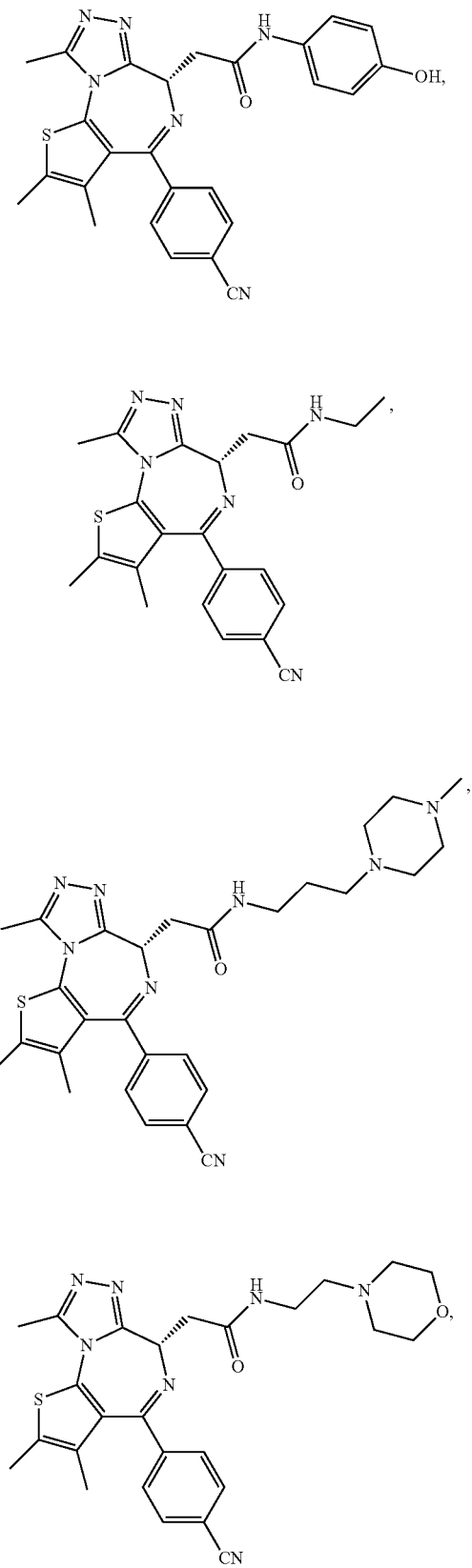

-continued
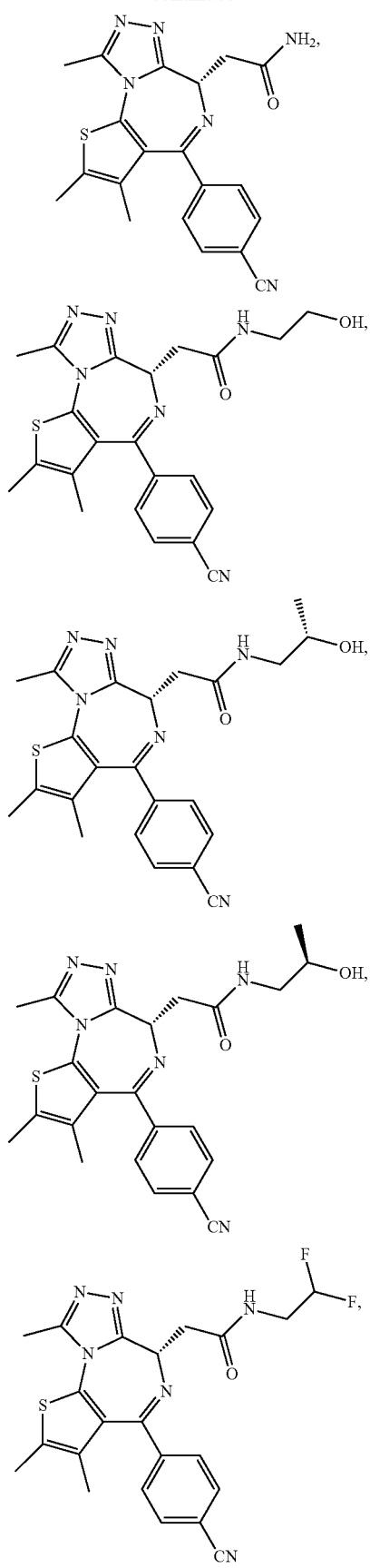
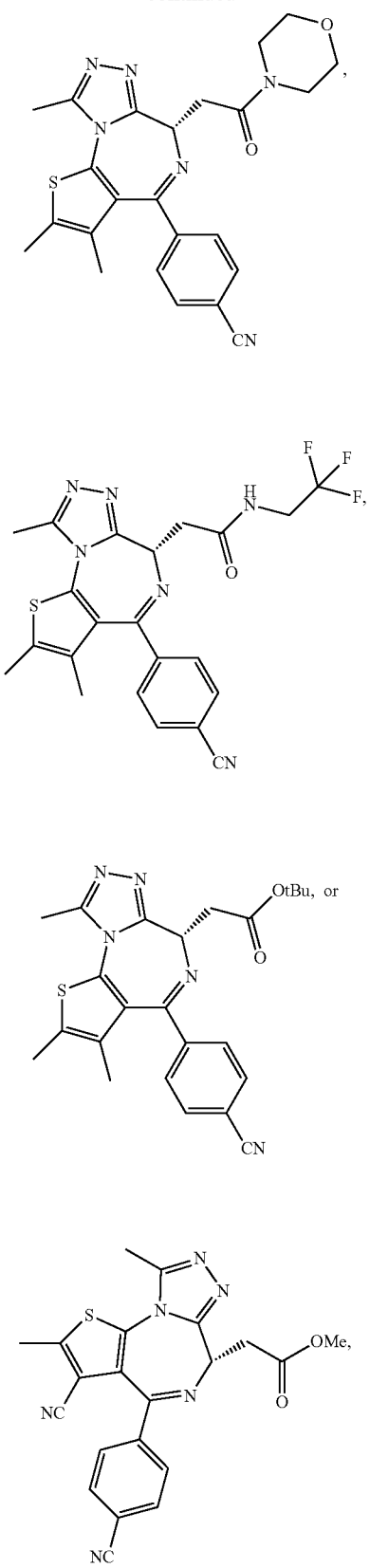
or a pharmaceutically acceptable salt, stereoisomer, or tautomer thereof.

11. A compound of Formula (II):

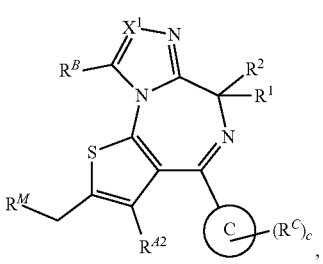

or a pharmaceutically acceptable salt, stereoisomer, or tautomer thereof, wherein:
  $R^M$ is —CN;
  $R^{A2}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;
  $X^1$ is N or $CR^5$, wherein $R^5$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;
  $R^B$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$OR^f$, —$SR^f$, —$N(R^f)_2$, —$NO_2$, or —CN;
  Ring C is phenyl;
  each occurrence of $R^C$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, —$OR^f$, —$SR^f$, —$N(R^f)_2$, —$NO_2$, or —CN;
  c is 0, 1, 2, 3, or 4;
  $R^1$ is hydrogen, halogen, optionally substituted alkyl, or —$(CH_2)_nL$, wherein n is 0, 1, 2, 3, or 4, and L is —$C(=O)R^3$, —$C(=O)OR^3$, or —$C(=O)NR^3R^4$;
  $R^2$ is hydrogen, halogen, or optionally substituted alkyl;
  each $R^3$ and $R^4$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group, or a nitrogen protecting group, or $R^3$ and $R^4$ are joined to form an optionally substituted heterocyclic or optionally substituted heteroaryl ring; and
  each occurrence of $R^f$ is independently, hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, optionally substituted sulfonyl, an oxygen protecting group, a sulfur protecting group, or a nitrogen protecting group, or two $R^f$ are joined to form an optionally substituted heterocyclic or optionally substituted heteroaryl ring;
wherein:
  each oxygen protecting group is independently —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, or —$P(=O)(N(R^{bb})_2)_2$;
  each sulfur protecting group is independently —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, or —$P(=O)(N(R^{bb})_2)_2$;
  each nitrogen protecting group is independently —OH, —$OR^{aa}$, —$N(R^{cc})_2$, —$C(=O)R^{aa}$, —$C(=O)N(R^{cc})_2$, —$CO_2R^{aa}$, —$SO_2R^{aa}$, —$C(=NR^{cc})R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, $C_{1-10}$ alkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, or 5-14 membered heteroaryl; wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups;
  each instance of $R^{aa}$ is, independently, selected from the group consisting of $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;
  each instance of $R^{bb}$ is, independently, selected from the group consisting of hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N(R^{cc})_2$, —$SO_2N(R^{cc})_2$, —$SO_2R^{cc}$, —$SO_2OR^{cc}$, —$SOR^{aa}$, —$C(=S)N(R^{cc})_2$, —$C(=O)SR^{cc}$, —$C(=S)SR^{cc}$, —$P(=O)(R^{aa})_2$, —$P(=O)(OR^{cc})_2$, —$P(=O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from the group consisting of hydrogen, $C_{1-10}$ alkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from the group consisting of halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, and 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents are joined to form =O or =S;

each instance of $R^{ee}$ is, independently, selected from the group consisting of $C_{1-6}$ alkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from the group consisting of hydrogen, $C_{1-6}$ alkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, 3-10 membered heterocyclyl, $C_{6-10}$ aryl, and 5-10 membered heteroaryl, or two e groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, selected from the group consisting of halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$ —C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, C$_{6-10}$ aryl, 3-10 membered heterocyclyl, and 5-10 membered heteroaryl; or two geminal R$^{gg}$ substituents are joined to form =O or =S;

wherein X$^-$ is a counterion.

12. A pharmaceutical composition comprising a compound of claim 1, or a pharmaceutically acceptable salt, stereoisomer, or tautomer thereof, and a pharmaceutically acceptable excipient.

13. A method of treating a disease associated with a bromodomain or bromodomain-containing protein in a subject in need thereof, wherein the disease is selected from the group consisting of testicular cancer, ovarian cancer, NUT midline carcinoma, chronic lymphocytic leukemia, mixed-lineage leukemia, epithelial neoplasia, and squamous cell carcinoma, the method comprising administering to the subject a therapeutically effective amount of a compound of claim 1, or a pharmaceutically acceptable salt, stereoisomer, or tautomer thereof.

14. A method for male contraception, the method comprising administering to a male subject in need thereof an effective amount of a compound of claim 1, or a pharmaceutically acceptable salt, stereoisomer, or tautomer thereof.

15. The compound of claim 11, the compound is of Formula (II-A-1), (II-A-2), (II-C-1), (II-D-1), (II-E-1), or (II-G-1):

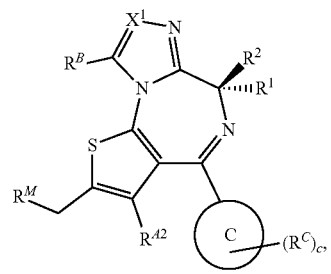

(II-A-1)

-continued (II-A-2)
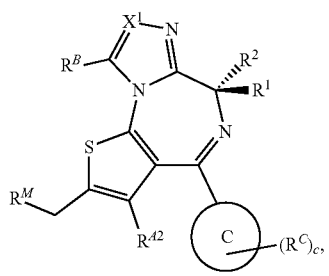

(II-C-1)
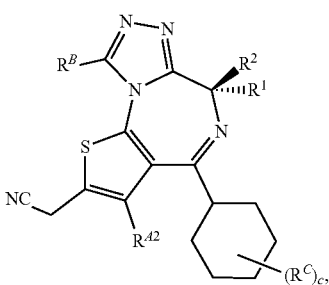

(II-D-1)
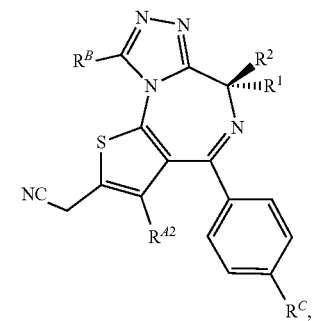

(II-E-1)
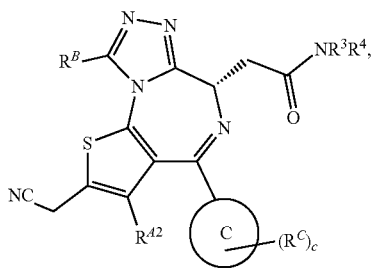

(II-G-1)
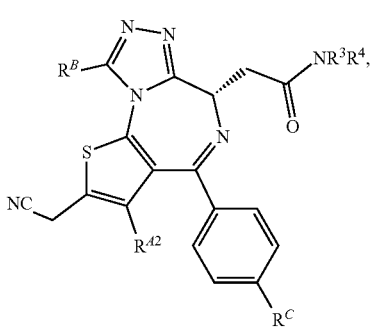

or a pharmaceutically acceptable salt, stereoisomer, or tautomer thereof.

16. The compound of claim 11, or a pharmaceutically acceptable salt, stereoisomer, or tautomer thereof, wherein $R^{A2}$ is hydrogen or optionally substituted $C_{1-6}$ alkyl.

17. The compound of claim 11, or a pharmaceutically acceptable salt, stereoisomer, or tautomer thereof, wherein Ring C is of formula:

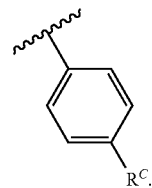

18. The compound of claim 11, or a pharmaceutically acceptable salt, stereoisomer, or tautomer thereof, wherein $R^1$ is —$(CH_2)_nC(=O)OR^3$ or —$(CH_2)_nC(=O)NR^3R^4$.

19. The compound of claim 11, or a pharmaceutically acceptable salt, stereoisomer, or tautomer thereof, wherein $R^1$ is —$(CH_2)_nC(=O)NR^3R^4$, and $R^3$ and $R^4$ are joined to form an optionally substituted heterocyclic or optionally substituted heteroaryl ring.

20. The compound of claim 11, or a pharmaceutically acceptable salt, stereoisomer, or tautomer thereof, wherein $R^3$ is hydrogen, and $R^4$ is optionally substituted $C_{1-6}$ alkyl or optionally substituted aryl.

21. The compound of claim 11, or a pharmaceutically acceptable salt, stereoisomer, or tautomer thereof, wherein $R^1$ is:

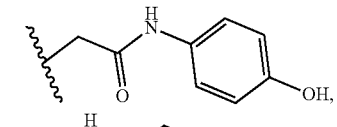
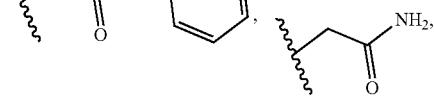
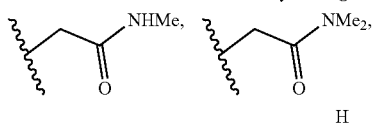
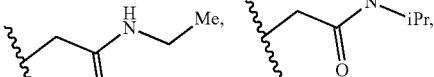
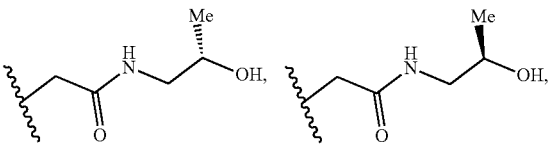

-continued
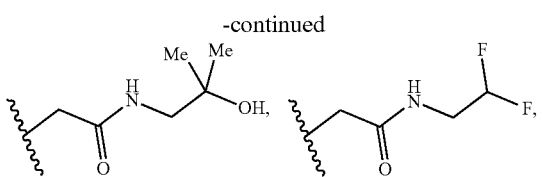
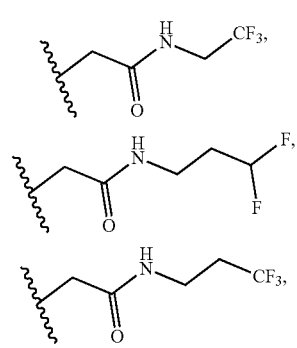
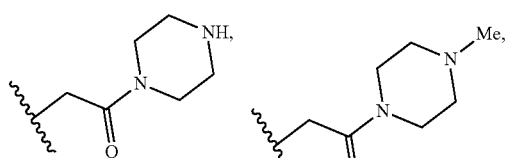
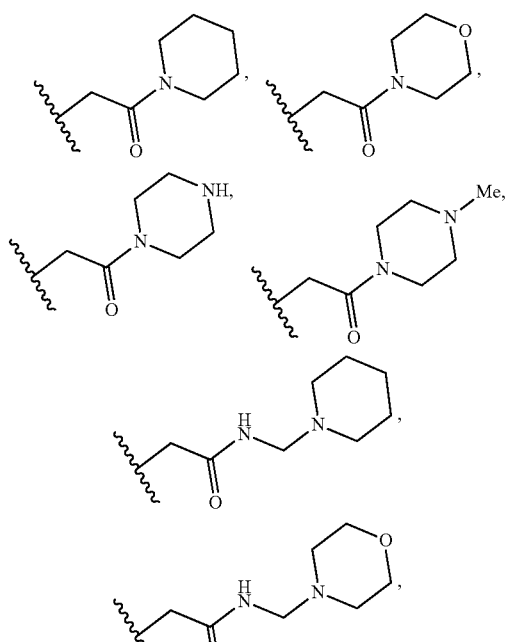
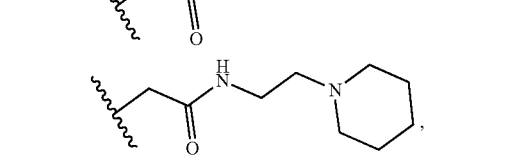
-continued
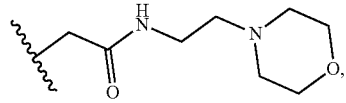
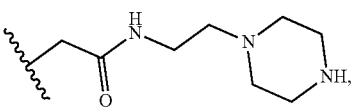
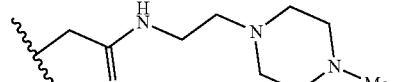
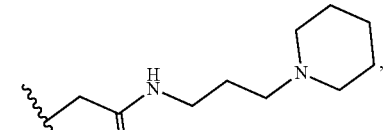
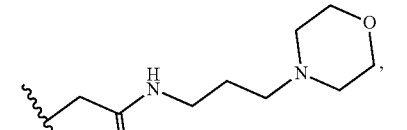
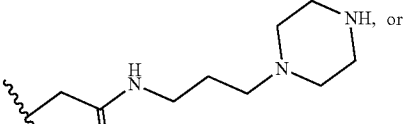
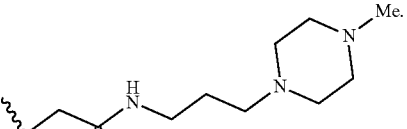
22. The compound of claim 11, or a pharmaceutically acceptable salt, stereoisomer, or tautomer thereof, wherein $R^2$ is hydrogen.
23. The compound of claim 11, wherein the compound is of formula:
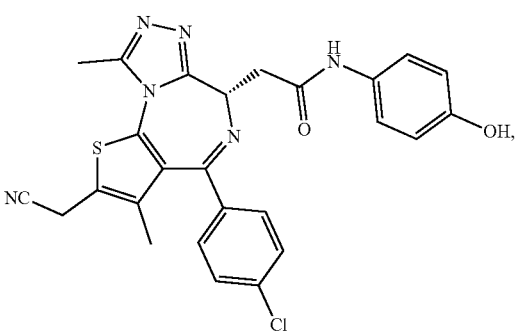

161
-continued
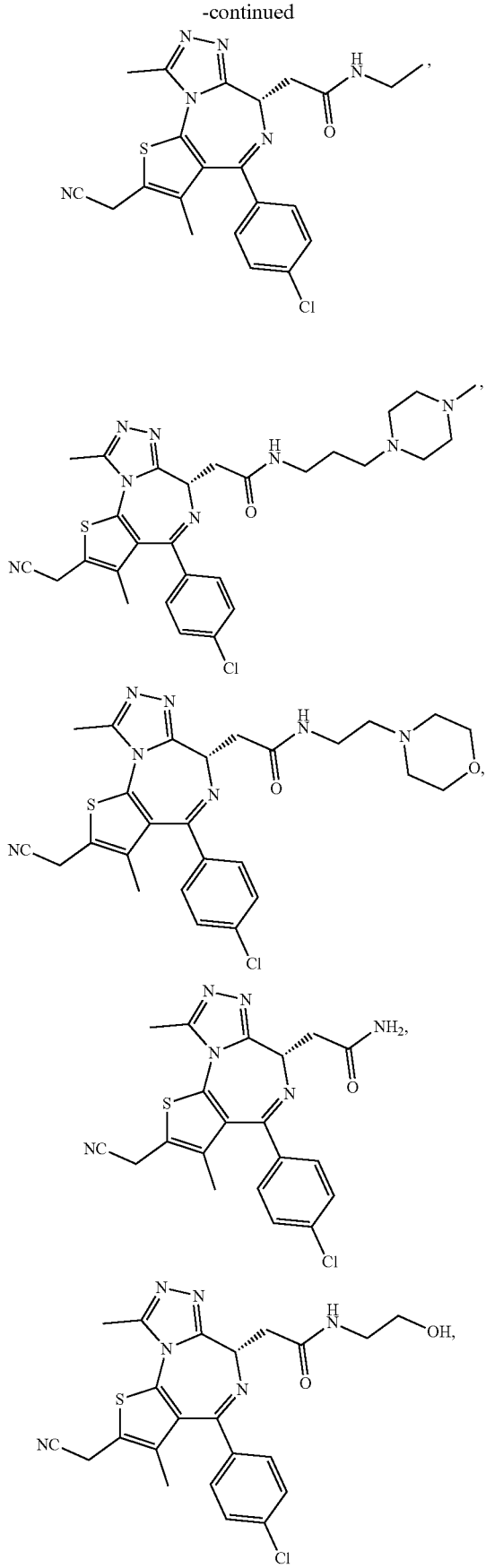
162
-continued
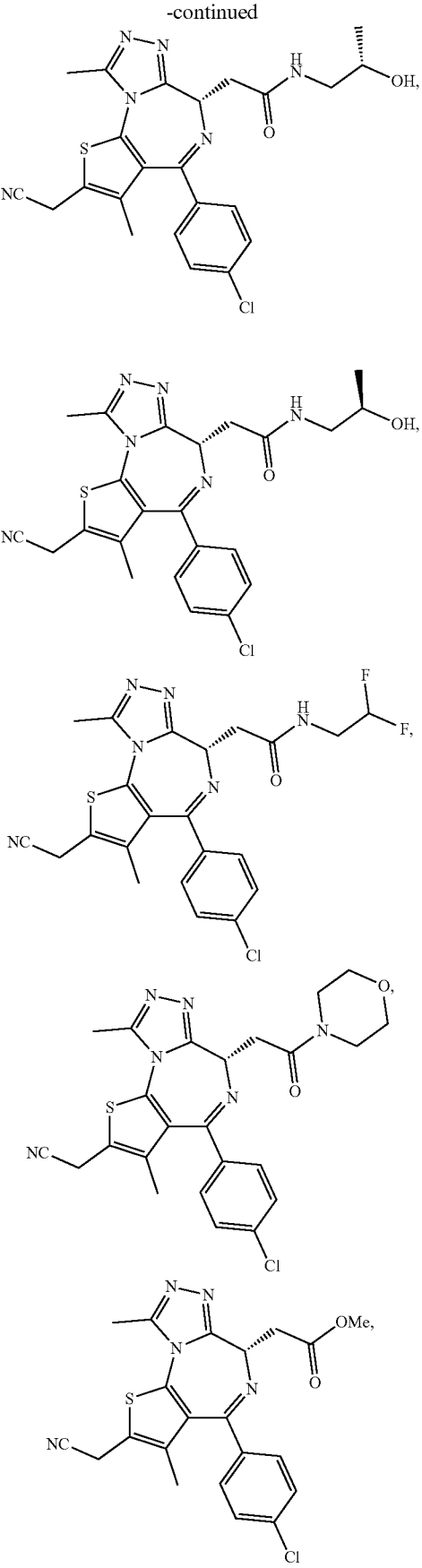

163                                    164
-continued                          -continued
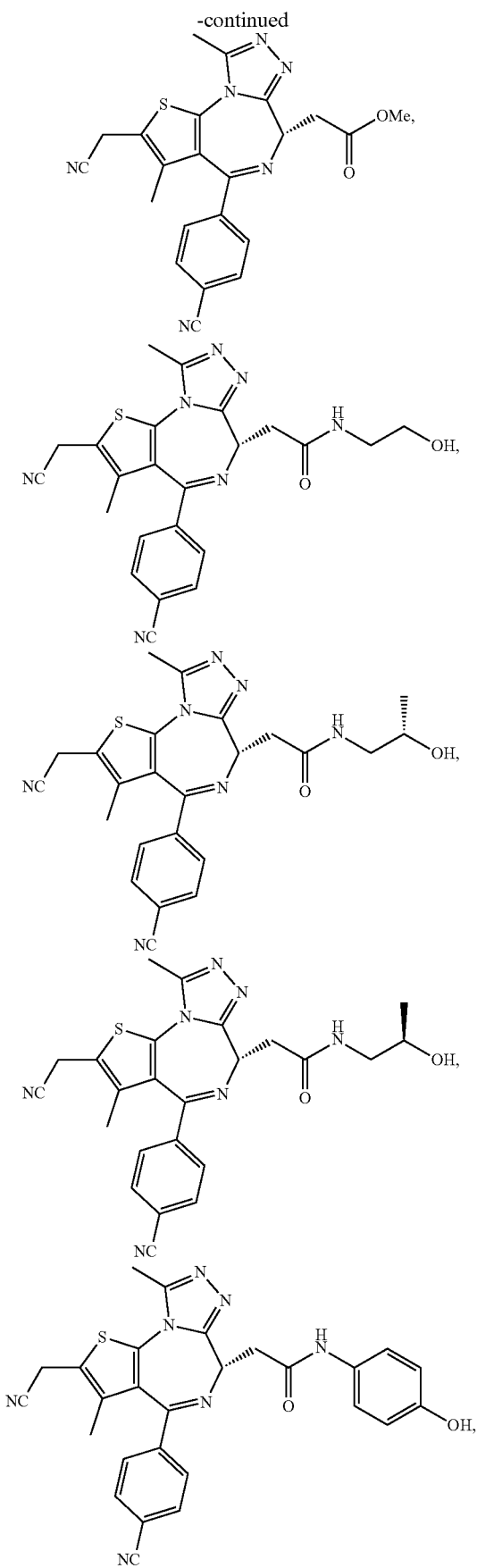
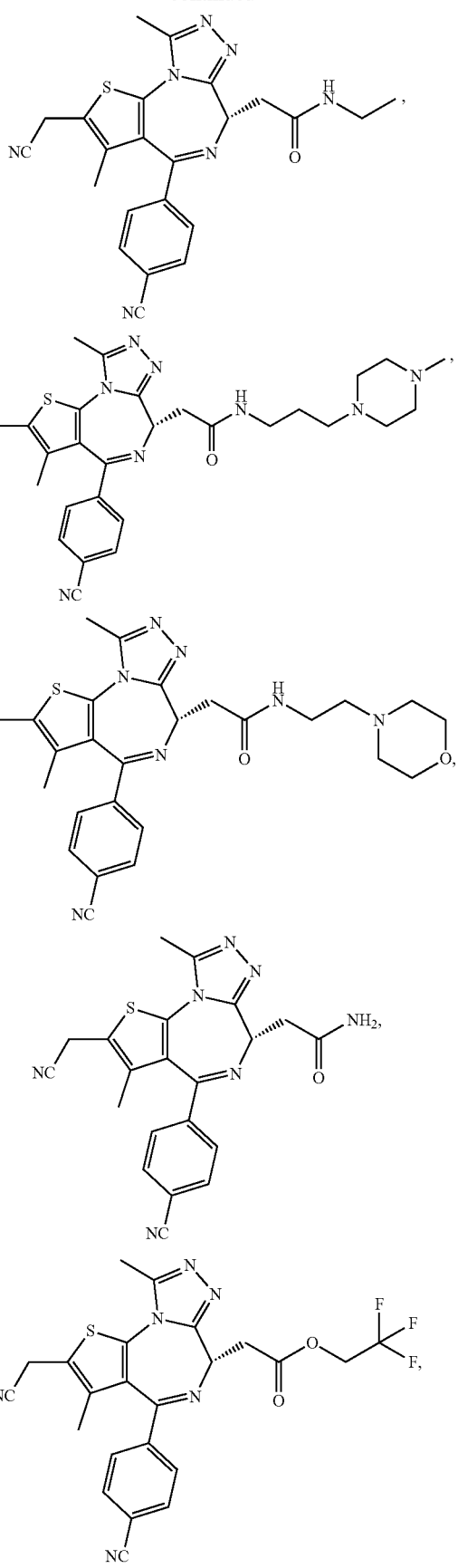

165
-continued

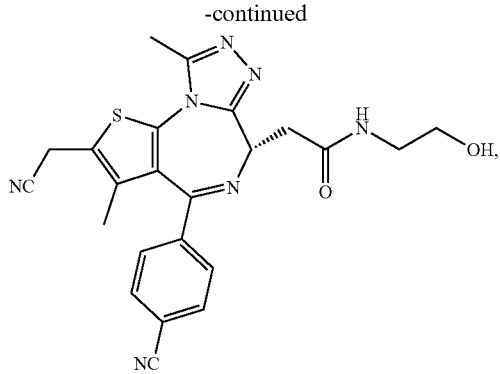

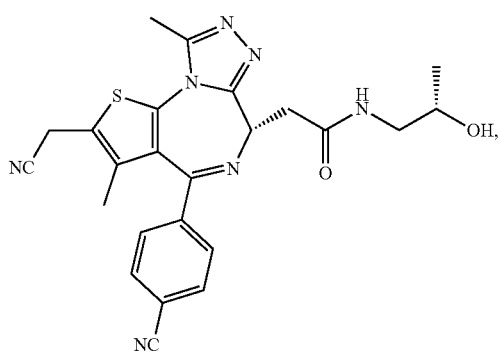

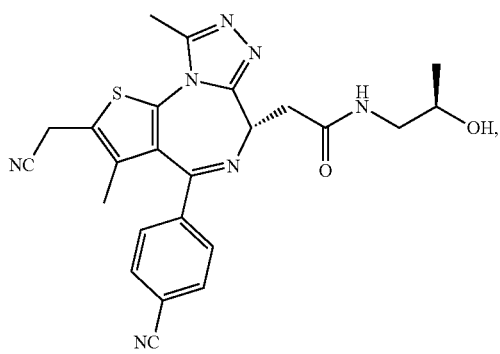

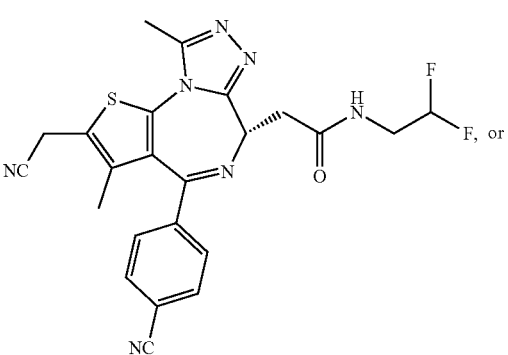

166
-continued

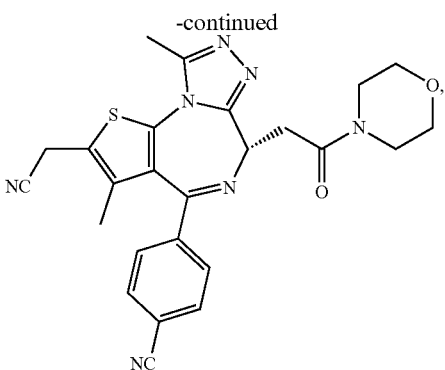

or a pharmaceutically acceptable salt, stereoisomer, or tautomer thereof.

24. The compound of claim 1, wherein the compound is of Formula (I):

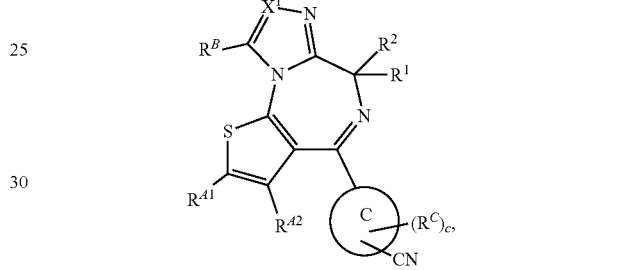

(I)

or a pharmaceutically acceptable salt thereof.

25. The compound of claim 11, wherein the compound is of Formula (II):

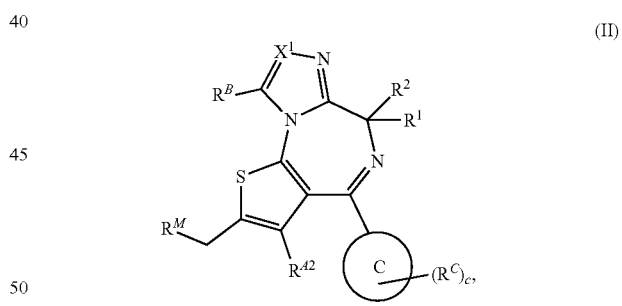

(II)

or a pharmaceutically acceptable salt thereof.

26. A pharmaceutical composition comprising a compound of claim 11, or a pharmaceutically acceptable salt, stereoisomer, or tautomer thereof, and a pharmaceutically acceptable excipient.

27. A method of treating a disease associated with a bromodomain or bromodomain-containing protein in a subject in need thereof, wherein the disease is selected from the group consisting of testicular cancer, ovarian cancer, NUT midline carcinoma, chronic lymphocytic leukemia, mixed-lineage leukemia, epithelial neoplasia, and squamous cell carcinoma, the method comprising administering to the subject a therapeutically effective amount of a compound of claim 11, or a pharmaceutically acceptable salt, stereoisomer, or tautomer thereof.

28. A method for male contraception, the method comprising administering to a male subject in need thereof an effective amount of a compound of claim 11, or a pharmaceutically acceptable salt, stereoisomer, or tautomer thereof.

* * * * *

UNITED STATES PATENT AND TRADEMARK OFFICE
CERTIFICATE OF CORRECTION

PATENT NO.        : 11,306,105 B2
APPLICATION NO.   : 15/758822
DATED             : April 19, 2022
INVENTOR(S)       : James E. Bradner et al.

Page 1 of 1

It is certified that error appears in the above-identified patent and that said Letters Patent is hereby corrected as shown below:

In the Claims

At Column 156, Line 51, "The compound of claim 11, the compound is of Formula (II-A-1), (II-A-2), (II-C-1), (II-D-1), (II-E-1), or (II-G-1):" should read -- The compound of claim 11, wherein the compound is of Formula (II-A-1), (II -A-2), (II-C-1), (II-D-1), (II-E-1), or (II-G-1): --

At Column 157, Line 13, " 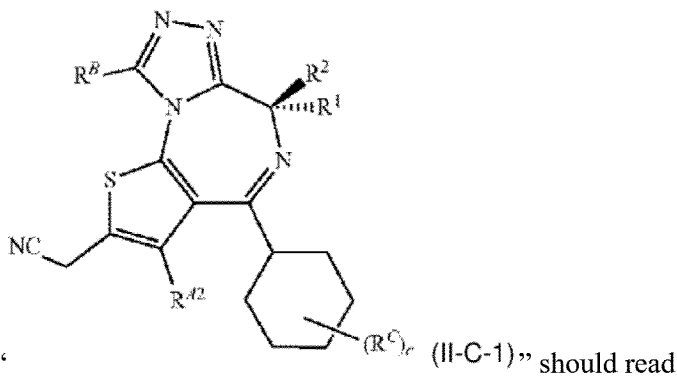 should read 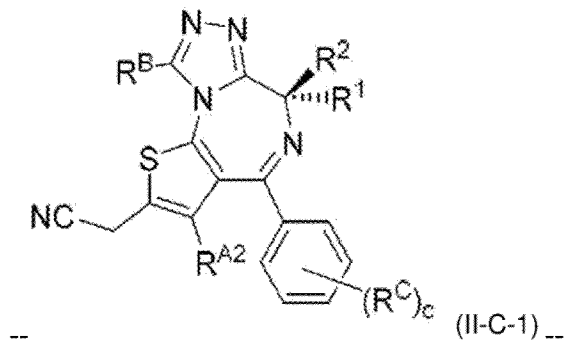 --

Signed and Sealed this
Twenty-third Day of August, 2022

Katherine Kelly Vidal
*Director of the United States Patent and Trademark Office*